(12) United States Patent
Wikström et al.

(10) Patent No.: US 12,202,790 B2
(45) Date of Patent: Jan. 21, 2025

(54) SULFONAMIDE DERIVATIVES HAVING SELECTIVE NOX INHIBITING ACTIVITY

(71) Applicant: GLUCOX BIOTECH AB, Färentuna (SE)

(72) Inventors: Per Wikström, Färentuna (SE); Erik Walum, Stockholm (SE)

(73) Assignee: GLUCOX BIOTECH AB, Färentuna (SE)

( * ) Notice: Subject to any disclaimer, the term of this patent is extended or adjusted under 35 U.S.C. 154(b) by 922 days.

(21) Appl. No.: 17/052,224

(22) PCT Filed: May 9, 2019

(86) PCT No.: PCT/EP2019/061950
§ 371 (c)(1),
(2) Date: Nov. 2, 2020

(87) PCT Pub. No.: WO2019/215291
PCT Pub. Date: Nov. 14, 2019

(65) Prior Publication Data
US 2021/0171456 A1  Jun. 10, 2021

(30) Foreign Application Priority Data
May 9, 2018  (EP) ...................... 18171556

(51) Int. Cl.
*C07C 311/16* (2006.01)
*A61P 9/10* (2006.01)

(52) U.S. Cl.
CPC .............. *C07C 311/16* (2013.01); *A61P 9/10* (2018.01)

(58) Field of Classification Search
CPC .......... C07C 311/16; A61P 9/10; A61K 31/18
See application file for complete search history.

(56) References Cited

U.S. PATENT DOCUMENTS

2008/0090821 A1*  4/2008  Hofmeister .......... C07D 403/12
                                                514/253.05
2009/0176804 A1   7/2009  Yang et al.
(Continued)

FOREIGN PATENT DOCUMENTS

CN   101817767 A    9/2010
WO   2007076055     7/2007
(Continued)

OTHER PUBLICATIONS

CAS Registry No. 1290283-32-7 (Year: 2011).*
(Continued)

*Primary Examiner* — Matthew P Coughlin
*Assistant Examiner* — Ashli Ariana Chicks
(74) *Attorney, Agent, or Firm* — Renner, Otto, Boisselle & Sklar, LLP

(57) ABSTRACT

A compound of formula (I) or a pharmaceutically acceptable salt thereof. The compound is useful in therapy, e.g. for the treatment of a condition or disorder associated with nicotinamide adenine dinucleotide phosphate oxidase 4 or 2 (Nox4 or Nox2) activity. A pharmaceutical composition comprising the compound.

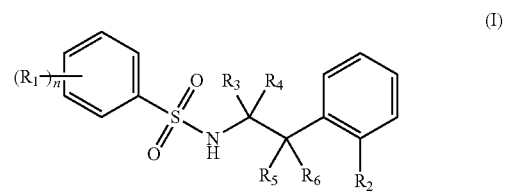

18 Claims, 13 Drawing Sheets
Specification includes a Sequence Listing.

(56) References Cited

U.S. PATENT DOCUMENTS

2009/0163545 A1 9/2009 Goldfarb
2014/0315947 A1 10/2014 Kwon et al.

FOREIGN PATENT DOCUMENTS

WO 2008022286 A2 2/2008
WO 2014047110 A2 3/2014
WO 2016096720 6/2016

OTHER PUBLICATIONS

Abbasi et al., "Sulfonamide derivatives of 2-amino-1-phenylethane as suitable cholinesterase inhibitors", Tropical Journal of Pharmaceutical Research, vol. 13, No. 5, pp. 739-745, May 2014.
Reaven, "Role of insulin resistance in human disease", Diabetes 37(12), Dec. 1988.
Sedeek M., et al.., "Molecular mechanisms of hypertension: role of Nox family NADPH oxidases" Current Opinion in Nephrology and Hypertension, 2009, 18:122-127.
Meng, et al., NADPH oxidase 4 promotes cisplatin-induced acute kidney injury via ROS-mediated programmed cell death and inflammation, Jan. 2018; 98(1):63-78.
Simone, et al., Complement-dependent NADPH oxidase enzyme activation in renal ischemia/reperfusion injury, Free Radic Biol Med, Sep. 2014; 74:263-73.
Wong, et al. "Diabetic retinopathy" Nat Rev Dis Primers, Mar. 2016, 17;2: 16012.
Saika, et al., "Epithelial-mesenchymal transition as a therapeutic target for prevention of ocular tissue fibrosis" Endocr Metab Immune Disord Drug Targets. Mar. 2008; 8(1):69-76.
CAS Registration Nos. 1328662-89-0 (Sep. 6, 2011), 1299152-85-4 (May 24, 2011), 1062293-76-8 (Oct. 16, 2008), 1014441-98-5 (Apr. 14, 2008), 1007680-73-0 (Mar. 13, 2008), 919966-89-5 (Feb. 8, 2007), 321721-87-3 (Feb. 14, 2001).
CAS Reg. Nos. 1327045-59-9 (Sep. 2, 2011), 1328564-25-5 (Sep. 5, 2011).
CAS Reg. Nos. 1327045-59-9 (Sep. 5, 2011), 1328564-25-5 (Sep. 2, 2011).
CAS Reg. Nos. 321712-59-8, 321712-58-7, 321712-57-6, 321712-46-3, 321712-45-2 (Feb. 14, 2001).
CAS Reg. Nos. 1099817-27-2 (Feb. 2, 2009), 1014508-87-2 (Apr. 14, 2008), 900399-83-9 (Aug. 10, 2006), 321712-37-2 (Feb. 14, 2001).
CAS Reg. Nos. 1326663-18-6, 1326663-12-0, 1326663-02-8 (Sep. 1, 2011).
Bjelakovic G. et al., "Antioxidant supplements for preventing gastrointestinal cancers" Cochrane Database Syst Rev. Jul. 16, 2008; (3):CD004183. Epub Jul. 16, 2008.
Wu et al., "Neutralization Escape Variants of Human Immunodeficiency Virus Type 1 are Transmitted from Mother to Infant" Journal of Virology, Jan. 2006, p. 835-844.
Houstis et al., "Insulin resistance and oxidative stress interdependency in non-alcoholic fatty liver disease" Nature 440, 2006.
Katakem et al., "Cerebral blood flow and metabolism of hyperperfusion after cerebral revascularization in patients with moyamoya disease" J cereb blood Flow Metab, Jan. 11, 2012.
Brar et al., "An NAD(P)H oxidase regulates growth and transcription in melanoma cells" Am J Physiol Lung Cell Mol Physiol, 282, 2002.
Grewal et al., "Serotonin 5-HT2A receptor induces TGF-β1 expression in mesangial cells via ERK: proliferative and fibrotic signals" Am J Physiol, 276, 1999.
Sundaresan et al., "Requirement for Generation of H2O2 for Platelet-Derived Growth Factor Signal Transduction" Science, vol. 270, Issue 5234, pp. 296-299.
Lundqvist-Gustafsson et al., "Activation of the granule pool of the NADPH oxidase accelerates apoptosis in human neutrophils" J Leukoc Biol, 65, 1999.
Steinbeck et al., "Involvement of hydrogen peroxide in the differentiation of clonal HD-11EM cells into osteoclast-like cells" J Cell Physiol, 176, 1998.
Wu et al., "Membrane Cofactor Protein Is a Receptor for Adenoviruses Associated with Epidemic Keratoconjunctivitis" J Virol, 78, 2004.
Rueckschloss et al., "NADPH oxidase-derived superoxide impairs calcium transients and contraction in aged murine ventricular myocytes" Experimental Gerontology, Elsevier, 2010, 45 (10), pp. 788.
Lambeth JD, Review Article "Nox enzymes, ROS, and chronic disease: An example of antagonistic pleiotropy", Free Radical Biology & Medicine 43, 2007.
Takac et al., "The Nox Family of NADPH Oxidases: Friend or Foe of the Vascular System", Curr Hypertens Rep. Nov. 10, 2011.
Montezano AC, "Novel Nox homologues in the vasculature: focusing on Nox4 and Nox5", Clin Sci London 2011.
Bedard K et al., "The Nox family of ROS-generating NADPH oxidases: physiology and pathophysiology" Physiol Rev. 2007.
Camici M et al., "Obesity-related glomerulopathy and podocyte injury: a mini review", Front Biosci 2012.
Nabeebaccus A et al., "NADPH oxidases and cardiac remodeling" Heart Fai Rev. 2011.
Kuroda J et al., "NADPH oxidase and cardiac failure" J Cardiovasc Transl Res. 2010.
Kuroda J et al., "NADPH oxidase 4 is a major source of oxidative stress in the failing heart" Proc Natl Acad Sci USA 2010.
Maejima Y et al., "Regulation of myocardial growth and death by NADPH oxidase" J Mol Cell Cardiol. 2011.
Barnes JL et al., "Myofibroblst differentiation during fibrosis: role of NADPH oxidases" Kidney international, 2011.
Alison Cave, "Selective targeting of NADPH oxidase for cardiovascular protection" Current Opinion in Pharmacology 2009.
Lambeth et al, "Nox enzymes, ROS, and chronic disease: An example of antagonistic pleiotropy", Free Radical Biology and Medicine, Elsevier Inc, US,vol. 43, No. 3, Aug. 1, 2007 (Aug. 1, 2007), p. 332-347.
Albert Van Der Vliet, "Nox enzymes in allergic airway inflammation" Biochimica et Biophysica Acta 1810, 2011.
Pendyala S et al., "Redox regulation of Nox proteins" Respiratory Physiology & Neurobiology 174, 2010.
Nair D et al., "Intermittent Hypoxia-Induced Cognitive Deficits are Mediated by NADPH oxidase Activity in a Murine Model of Sleep Apnea" PLoS One, vol. 6, Issue 5, May 2011.
Chia-Hung Hsieh et al., "NADPH oxidase Subunit 4-Mediated Reactive Oxygen species Contribute to Cycling Hypoxia-Promoted Tumor Progression in Glioblastoma Multiforme" PloS One, vol. 6, issue 9, Sep. 2011.
Kim et al., "Generation and Characterization of DNA Vaccines Targeting the Nucleocapsid Protein of Severe Acute Respiratory Syndrome Coronavirus" Journal of Virology, May 2004, p. 4638-4645.
Augusto C Montezano et al., "NADPH Oxidase 5 is a Pro-Contractile Nox Isoform and a Point of Cross-Talk for Calcium and Redox Signaling—Implications in Vascular Function" J Am Heart Assoc. 2018; 7.
Briones AM et al., "Differential regulation of Nox1, Nox2 and Nox4 in vascular smooth muscle cells from WKY and SHR" Journal of the American Society of Hypertension 5:3, 2011.
Kinnula VL et al., "Oxidative Stress in Pulmonary Fibrosis A Possible Role for Redox Modulatory Therapy" Am J Respir Crit Care Med 172:417-422 2005.
John M. Bennett et al, "Synthesis of phthalan and phenethylamine derivatives via addition of alcohols to rhodium(II)-azavinyl carbenoids", Tetrahedron Letters,vol. 58, No. 12, Mar. 1, 2017 (Mar. 1, 2017), p. 1117-1122.
K Kuwano et al., Lambeth et al, "Oxidative stress in lung epithelial cells from patients with idiopathic interstitial pneumonias" Eur Respir J 2003; 232-240.
Thomas Duhamel et al., "Supporting Information for Engineering Molecular Iodine Catalysis for Alkyl-Nitrogen Bond Formation", Mar. 20, 2018 (Mar. 20, 2018).
Serrander et al., "NOX4 activity is determined by mRNA levels and reveals a unique pattern of ROS generation" Biochem. J. (2007) 406, 105-114.

(56) References Cited

OTHER PUBLICATIONS

Ago et al., Nox4 as the Major Catalytic Component of an Endothelial NAD(P)H Oxidase, Circulation, 109, 2004.
Takac et al., "The E-loop is Involved in Hydrogen Peroxide Formation by the NADPH Oxidase Nox4" J. Biol. Chem. 286, 2012.
De Deken et al., "Cloning of Two Human Thyroid cDNAs Encoding New Members of the NADPH Oxidase Family" J.Biol Chem., 275(30), 2000.
Chamseddine et al., "Vascular Signaling by Free Radicalsgp91 phox Contributes to NADPH oxidase activity in aortic fibroblasts but not smooth muscle cells" Am J Physiol Heart Circ Physiol. 285, 2003.
Ellmark et al., "The contribution of Nox4 to NADPH oxidase activity in mouse vascular smooth muscle" Cardiovasc Res. 65, 2005.
Van Buul et al., "Expression and Localization of NOX2 and NOX4 in Primary Human Endothelial Cells" Antioxidants & Redox Signaling, vol. 7, 2005.
Kawahara et al., "Molecular evolution of the reactive oxygen-generating NADPH oxidase (Nox/Duox) family of enzymes" BMC Evol Biol. 7, 2007.
Krause et al., "Tissue Distribution and Putative Physiological Function of NOX Family NADPH Oxidases" Jpn. J. Infect. Dis. 57(5), 2004.
Griendling, "NAPH Oxidases: New Regulators of Old Functions" Antioxid Redox Signal. 8(9), 2006.
Graham et al., "NADPH Oxidase 4 is an oncoprotein localized to mitochondria" Cancer Biology & Therapy 10(3), 2010.
Shanmugasundaram et al., "NOX4 functions as a mitochondrial energetic sensor coupling cancer metabolic reprogramming to drug resistance" Nat Comm. Oct. 19, 2017;8(1):997.
Uhlig, Mechanotransduction in the Lung Ventilation-induced lung injury and mechanotransduction: stretching in too far? Am J Physiol Lung Cell Mol Physiol 282: L892-L896 2002.
Ramli et al., Pharmacological Profile of Quinoxalinone Hindawi Publishing Corporation Journal of Chemistry vol. 2014.
Basuroy et al., "Nox4 NADPH oxidase mediates oxidative stress and apoptosis caused by TNF-α in cerebral vascular endothelial cells" Am J Physiol Cell Physiol vol. 296, 2009.
Sedwick, "NOX4: A Guilty Party in Stroke Damage" PLos Biology, vol. 8 issue 9, 2010.
Kleinschnitz et al., "Post-Stroke Inhibition of Induced NADPH Oxidase Type 4 prevents Oxidative Stress and Neurodegeneration" PLOS Biol. vol. 8 issue 9, 2010.
Datla et al., "Important Role of Nox4 Type NADPH Oxidase in Angiogenic Responses in Human Microvascular Endothelial Cells in Vitro" Arterioscler Throm Vasc Biol. 27(11), 2007.
Zhang et al., "NADPH oxidase-4 mediates protection against chronic load-induced stress in mouse hearts by enhancing angiogenesis" PNAS, 107, 2010.
Garriodo-Urbani et al., "Targeting Vascular NADPH Oxidase 1 Blocks Tumor Angiogenesis through a PPARa Mediated Mechanism" Plos One 2011.
Takac et al., "The Nox Family of NADPH Oxidases: Friend or Foe of the Vascular System?" Curr Hypertens Rep, 14, 2012.
Carnesesecchi et al., "A Key Role for NOX4 in Epithelial Cell Death During Development of Lung Fibrosis" Antiox Redox Signal. 1:15(3), 2011.
Block et al., "Subcellular localization of Nox4 and regulation in diabetes" PNAS vol. 106, No. 34, 2009.
Jiang et al., "Systemic upregulation of NADPH oxidase in diet-induced obesity in rats" Redox rep, 16 (6), 2011.
Anvari et al., "The novel NADPH oxidase 4 inhibitor GLX351322 counteracts glucose intolerance in high-fat diet-treated C57BL/6 mice" Free Radical Res. 2015 49 (11).
Wang et al., P-O (2018) "The novel NADPH oxidase 4 selective inhibitor GLX7013114 counteracts human islet cell death in vitro" PLoS One 13(9); e0204271.
Stephen M. F. Jamieson et al, "3-(3,4-Dihydroisoquinolin-2(1 H )-ylsulfonyl)benzoic Acids: Highly Potent and Selective Inhibitors of the Type 5 17-&bgr;- Hydroxysteroid Dehydrogenase AKR1C3", Journal of Medicinal Chemistry,vol. 55, No. 17, Sep. 13, 2012 (Sep. 13, 2012), p. 7746-7758.
Hongwei Zhang et al., "Supporting Information for: Selective Piperidine Synthesis Exploiting Iodine-Catalyzed C sp3-H Amination under Visible Light", May 10, 2017 (May 10, 2017).
Cheng et al., "Small Molecule Regulators of Protein Arginine Methyltransferases" The Journal of Biological Chemistry vol. 279 No. 23; Jun. 2004 23892-23899.
Testura Ago et al., "The NADPH Oxidase Nox4 and Aging in the Heart" Aging, Dec. 2010, vol. 2 No. 12.
New et al., "IGF-I increases the expression of the fibronectin by Nox4-dependent Akt phosphorylation in renal tubulara epithelial cells" Am J Physiol Cell Physiol. 302, 2012.
Chen et al., "Angiotensin II Induces Epithelial-to-Mesenchymal Transition in Renal Epithelial Cells through Reactive Oxygen Species/Src/Caveolin-Mediated Activation of an Epidermal Growth Factor Receptor-Extracellular Signal-Regulated Kinase Signaling Pathway" Molecular and Cellular Biology, p. 981-991, 2012.
Petrushanko et al., "Oxidation of Ca2+-Binding Domain of NADPH Oxidase 5 (NOX5): Toward Understanding the Mechanism of Inactivation of NOX5 by ROS" PLOS One 11(7): 2016.
Antonetti et al., "Mechanisms of Disease: Diabetic retinopathy" N Engl. J Med 2012; 366 (13):1227-39.
Peng et al., "Diabetic retinopathy: Focus on NADPH oxidase and its potential as therapeutic target" Eur J Pharmacol. Apr. 19, 2019; 853:381-387.
Jiao et al., "Activation of the Notch-Nox4-reactive oxygen species signaling pathway induces cell death in high glucose-treated human retinal endothelial cells". Mol Med Rep. Jan. 2019; 19(1):667.
Poulaki V et al., Acute intensive insulin therapy exacerbates diabetic blood-retinal breakdown via hypoxia-inducible factor-1 alpha and VEGF, J Clin Invest 109: 805-815, 2002.
Meng et al., "NADPH Oxidase 4 mediates Insulin-Stimulated HIF-1 a and VEGF Expression, and Angiogenesis in Vitro", PLoS One, Oct. 2012, vol. 7, issue 10.
Zeisberg M et al., "BMP-7 counteracts TGF-B1-induced epithelial-to-mesenchymal transition and reverses chronic renal injury" Nat Med. 2003; 9:964-968.
Kim KK et al., "Alveolar epithelial cell mesenchymal transition develops in vivo during pulmonary fibrosis and is regulated by the extracellular matrix" Proc Natl Acad Sci USA. 2006;103:13180-13185.
Zeisberg M et al., "Fibroblasts Derive from Hepatocytes in Liver Fibrosis via Epithelial to Mesenchymal Transition" J Biol Chem. 2007; 282:23337-23347.
Krijnen et al., "Increased Nox2 expression in human cardiomyocytes after acute myocardial infarction" J Clin Pathol 2003; 56 194-199.
Ogawa Y et al., "Epithelial mesenchymal transition in human ocular chronic graft-versus-host disease" Am J Pathol. 2009; 175(6):2372-2381.
Jing Y. et al., "Novel NADPH oxidase inhibitor VAS2870 suppresses TGF-B-dependent epithelial-to-mesenchymal transition in retinal pigment epithelial cells" Int J Mol Med. Jul. 2018; 42(1): 123-130.
Hales AM et al., "Cataract Induction in Lenses Cultured With Transforming Growth Factor-B" Investigative ophthalmology & visual science. 1995; 36(8):1709-13.
Liu J et al., "Induction of Cataract-like Changes in Rat Lens Epithelial Explants by Transforming Growth Factor B" Investigative ophthalmology & visual science. 1994; 35(2):388-401.
Das SJ et al., "Nox4 Plays a Role in TGF-B-Dependent Lens Epithelial to Mesenchymal Transition" Investigative ophthalmology & visual science. 2016; 57(8):3665-73.
Ma et al., "NADPH oxidase 2 regulates NLRP3 inflammasome activation in the brain after traumatic brain injury", Oxid Med. Cell Longev. 2017 60576009.
Dohi et al., "Gp91phox(Nox2) in classical activated microglia exacerbates traumatic brain injury", J Neuroinflamm. 7 (2010) 41.
Wang et al., "Regulatory role of NADPH oxidase 2 in the polarization dynamics and neurotoxicity of microglia/macrophages after traumatic brain injury". Free Radic. Biol. Med. 113 (2017) 119-131.

(56) References Cited

OTHER PUBLICATIONS

Kumar et al., "Nox2 drives M1-like microglia/macrophage activation and neurodegeneration following experimental traumatic brain injury", Brain Behav. Immun. 58 (2016) 291-309.
Ma et al., "Deletion of NADPH oxidase 4 reduces severity of traumatic brain injury", Free Radic. Biol. Med. 117 (2018) 66-75.
Lo et al., "NADPH oxidase inhibition improves neurological outcomes in surgical-induced brain injury", Neurosci. Lett. 414 (2007) 228-232.
Chadran et al., "A combination antioxidant therapy to inhibit Nox2 and activate Nrf2 decreases secondary brain damage and improves functional recovery after traumatic brain injury" J. Cereb. Blood Flow. Metab. (2017).
Loffredo et al., "NOX2 up-regulation is associated with artery dysfunction in patients with peripheral artery disease" Int J Cardiol 2013; 165: 184-192.
Loffredo et al., "Dark Chocolate Acutely Improves Waling Autonomy in Patients with Peripheral Artery Disease" J Am Heart Assoc. 2014; 3.
Sorce S. et al., "NOX Enzymes in the Central Nervous System: From Signaling to Disease" Antioxidants & Redox Signaling 2009; 11: 2481-2504.
Rojas M. et al., "Requirement of NOX2 Expression in Both Retina and Bone Marrow for Diabetes-Induced Retinal Vascular Injury" PLOS One. 8 (12): e84357.
Schiavone S et al., "The NADPH oxidase NOX2 as a novel biomarker for suicidality: evidence from human post mortem brain samples" Translational Psychiatry vol. 6, p. e813 (2016).
Fernandez D. et al., "A new type of five-membered heterocyclic inhibitors of basic metallocarboxypeptidases" European Journal of Medicinal Chemistry vol. 44, (2009), 3266-3271.
Aronica L. et al., "Synthesis of N-Heteroaromatic Compounds through Cyclocarbonylative Sonogashira Reactionsin" Eur. J. Org. Chem. 2017, 955-963.
Priebbenow D. et al., "Asymmetric induction in domino Heck-aza-Michael reactions" Tetrahedron 53 (2012), 1468-1471.
Henderson et al., "ChemInform Abstract: An Alternative Strategy to the Pictet-Spengler Method for Tetrahydroisoquinoline Synthesis: A Feasibility Study" Tetrahedron 53 (2012), 4657-4660.
Kang et al., "Synthesis of Ethyl 1,2,3,4-Tetrahydroisoquinoline-1-carboxylates by Pictet-Spengler Condensation Using Phenyliodine(III) Bis(trifluoroacetate)" Heterocycles, Japan Institute of Heterocyclic Chemistry JP,vol. 57, No. 1, Jan. 1, 2002 (Jan. 1, 2002), p. 1-04.
Jiao et al, "Synthesis of Indolines and Tetrahydroisoquinolines from Arylethylamines by Pd II—Catalyzed C?H Activation Reactions", Angewandte Chemie, International Edition,vol. 47, No. 34, Aug. 11, 2008 (Aug. 11, 2008), p. 6452-6455.
Ago et al., "Pathophysiological Roles of NADPH Oxidase/Nox Family Proteins in the Vascular System" Circ J 2011; 75: 1791-1800.
Brandes et al., "Vascular NADPH oxidases: molecular mechanisms of activation" Elsevier Cardiovascular Research 65 (2005) 16-27.
Brar et al., "NOX5 NAD(P)H oxidase regulates growth and apoptosis in DU 145 prostate cancer cells" Am J Physiol Cell Physiol 285: C353-C369 2008.
Datla et al., "Poldip2 Knockdown Inhibits Vascular Smooth Muscle Proliferation and Neointima Formation by Regulating the Express of PCNA and p21" Lab Invest. Mar. 2019; 99(3): 387-398.
Carpineto et al., "Neuroretinal alterations in the early stages of diabetic retinopathy in patients with type 2 diabetes mellitus" Eye (2016) 30, 673-679.
Cave et al., NADPH oxidase-derived reactive oxygen species in cardiac pathophysiology Phil. trans. R. Soc. B (2005) 360, 2327-2334.
Chen et al., From form to function: the role of Nox4 in the cardiovascular system Frontiers in Physiology Nov. 1, 2012.
Jiang et al., "Reductive Carboxylation supports redox homeostasis during achorage-independent growth" Nature Apr. 14, 2016; 532(7598): 255-258.
Konior et al., "NADPH Oxidases in Vascular Pathology" Antioxidants & Redox Signaling vol. 20, No. 17 2014.
CAS Registration No. 461453-88-3; Oct. 15, 2002.
CAS Registration No. 1062196-44-4; Oct. 16, 2008.
CAS Registration No. 1099817-28-3; Feb. 2, 2009.
CAS Registration No. 1147538-39-3; May 19, 2009.
CAS Registration No. 1327100-78-6; Sep. 2, 2011.
CAS Registration No. 1328662-95-8; Sep. 6, 2011.
CAS Registration No. 1502967-87-4; Dec. 25, 2013.
CAS Registration No. 1513228-92-6; Jan. 7, 2014.
CAS Registration No. 2202061-67-2; Mar. 30, 2018.
CAS Registration No. 2202313-44-6; Mar. 30, 2018.
Nathan A. Lack et al.; Targeting the Binding Function 3 (BF3) Site of the Human Androgen Receptor Through Virtual Screening; NIH Public Access; J Med Chem; Dec. 22, 2011; pp. 1-23; 54(24).

* cited by examiner

SULFONAMIDE DERIVATIVES HAVING SELECTIVE NOX INHIBITING ACTIVITY

This application is a national phase of International Application No. PCT/EP2019/061950 filed May 9, 2019 and published in the English language, which claims priority to European Application No. 18171556.6 filed May 9, 2018, both of which are hereby incorporated herein by reference.

FIELD OF THE INVENTION

The present invention relates to novel sulfonamide derivatives and their use in therapy, in particular in the treatment of conditions or disorders associated with nicotinamide adenine dinucleotide phosphate oxidase 4 or 2 (Nox4 or Nox2). More specifically, the present invention relates to sulfonamide derivatives that are inhibitors of Nox4 and/or Nox2 and their use in the treatment of various diseases, in particular diseases that are caused or driven by elevated Nox4 and/or Nox2 activity.

BACKGROUND OF THE INVENTION

The definition of oxidative stress is an in vivo imbalance between the formation and elimination of reactive oxygen. Changes of the normal redox state in the cell or tissues can produce harmful radicals that may damage components of the cellular machinery, including DNA, proteins and lipids. If the cellular components are chemically altered that cause genetic changes, this has generally been considered to promote formation of cancer or other serious diseases.

Sources of oxygen radicals—Numerous in vivo generators of oxygen radicals ($O_2^-$, $H_2O_2$ and $OH^-$) that potentially can cause oxidative stress have been identified: complex I and III in the mitochondria and NADPH oxidase, xanthine oxidase, cytochromes P450, metal ions (cobalt, vanadium, chromium, copper and iron) and some organic compounds that can redox cycle.

General antioxidants—There also are numerous endogenously cellular antioxidants such as superoxide dismutase (SOD), catalase, glutathione peroxidase, peroxiredoxins and sulfiredoxin. Vitamins provided by the food are also considered as an important part of the protection of the organism from harmful oxygen radicals, and recent discovery of important antioxidants present in many sources of food has increased the arsenal of antioxidants.

Antioxidants as therapeutics—It is very clear that some antioxidants can be helpful in preventing diseases and promote health. What is much less clear is what type of antioxidants can be used. Many of the antioxidants present in natural food are redox active. If these types of redox active substances are isolated and provided as complementary pharmaceuticals—this may end up being more harmful than helpful. Clinical trials have shown that untargeted application of antioxidants, which broadly scavenge oxygen radicals, are not only ineffective but may even be harmful. This was illustrated in a study made with sixty-seven randomized trials with 232,550 participants including healthy and patients with various diseases (Bjelakovic G, Nikolova D, Simonetti R G, Gluud C. Cochrane Database Syst Rev. 2008 Jul. 16; (3):CD004183. Epub 2008 Jul. 16). Thus general antioxidants that are redox active may actually be adding to the cellular damage, by mediating a harmful redox cycle. Other general antioxidants will harmfully block normal cellular in vivo activity necessary to maintain bodily function.

Source and role of reactive oxygen—What has become increasingly clear is that what is causing excessive production and accumulation of reactive oxygen, in a number of pathological conditions, such as inflammation, type 2 diabetes, diabetes complications, polycystic ovary syndrome, stroke, detrimental neurological conditions and cancer, is not generally leaking oxygen radicals such as complex I or III in the mitochondria—rather it is up-regulated powerful producers of oxygen radicals—that are part of the normal cellular signal transduction system. Thus the definition of oxidative stress need not be oxygen radicals that will irreversibly alter DNA, protein or lipids, but instead increasingly interfere, if up regulated with "normal" signal transduction creating an imbalance on a cellular level that eventually may alter other tissues and whole bodily function. A typical example of this is the metabolic syndrome, connected to vascular disease, diabetes 2, stroke, nephropathy, neuropathy, heart failure and stroke with insulin resistance as the initiating factor (Reaven, "Role of insulin resistance in human disease", Diabetes 37(12), 1988). Insulin resistance in itself is also part of normal bodily function as a tool to direct storage of energy selectively to a suitable receiving organ. However, when metabolic changes occur, such as in overfeeding, or other disturbances such as acromegaly with excess growth hormone production or malfunctioning leptin as in ob/ob-mice, this will induce a harmful condition with an uncontrolled insulin resistance that may cause organ failure connected to the metabolic syndrome. The common denominator to the uncontrolled insulin resistance is overproduction of local and systemic oxygen radicals (Houstis et al., Nature 440, 2006; Katakam et al., J cereb blood Flow Metab, 2012 Jan. 11).

One of the most interesting candidates for this overproduction is a family of trans-membrane proteins (enzymes), referred to as NADPH oxidase (Nox). There are seven family members of Nox identified (Nox 1-5 and Duox 1-2) that very often are being recognized as a major or key source of reactive oxygen and that also play a major role in a number of cellular events as part of the normal cellular signal transduction system, including proliferation (Brar et al., Am J Physiol Lung Cell Mol Physiol, 282, 2002), growth (Brar et al., Am J Physiol Cell Physiol, 282, 2002), fibrosis (Grewal et al., Am J Physiol, 276, 1999), migration (Sundaresan et al., Science, 270, 1995), apoptosis (Lundqvist-Gustafsson et al., J Leukoc Biol, 65, 1999), differentiation (Steinbeck et al., J Cell Physiol, 176, 1998), cytoskeletal rearrangement (Wu et al., J Virol, 78, 2004) and contraction (Rueckschloss et al., Exp Gerontol, 45, 2010).

NADPH oxidase and disease—Some genetic conditions with decreased NADPH oxidase activity have been identified—defect Nox2 decreases immunologic response to kill and neutralize microbial attacks (Chronic granulomatous disease)—defect Nox3 in inner ear renders defective gravity perception and dual NADPH oxidase Duox2 having deficient enzymatic activity in the thyroid gland gives rise to hypothyroidism.

There is however a much larger list of publications that also seems to grow exponentially, that witness of strong evidence that increased Nox activity is part of or even causative of a number of diseases (Lambeth J D, Review Article "*Nox enzymes, ROS, and chronic disease: An example of antagonistic pleiotropy*", Free Radical Biology & Medicine 43, 2007; Takac I et al., "*The Nox Family of NADPH Oxidases: Friend or Foe of the Vascular System*", Curr Hypertens Rep. 2011 Nov. 10; Montezano A C, "*Novel Nox homologues in the vasculature: focusing on Nox4 and Nox5*", Clin Sci London 2011; Bedard K et al., "*The Nox* family of ROS-generating NADPH oxidases: physiology and pathophysiology" Physiol Rev. 2007; Camici M et al., "Obesity-related glomerulopathy and podocyte injury: a mini review", Front Biosci 2012; Nabeebaccus A et al., "NADPH oxidases and cardiac remodeling" Heart Fai Rev. 2011; Kuroda J et al., "NADPH oxidase and cardiac failure" J Cardiovasc Transl Res. 2010; Kuroda J et al., "NADPH oxidase 4 is a major source of oxidative stress in the failing heart" Proc Natl Acad Sci USA 2010; Maejima Y et al., "Regulation of myocardial growth and death by NADPH oxidase" J Mol Cell Cardiol. 2011; Barnes J L et al., "Myofibroblst differentiation during fibrosis: role of NADPH oxidases" Kidney international, 2011; Alison Cave "Selective targeting of NADPH oxidase for cardiovascular protection" Current Opinion in Pharmacology 2009; Albert van der Vliet "Nox enzymes in allergic airway inflammation" Biochimica et Biophysica Acta 1810, 2011; Pendyala S et al., "Redox regulation of Nox proteins" Respiratory Physiology & Neurobiology 174, 2010; Nair D et al., "Intermittent Hypoxia-Induced Cognitive Deficits Are Mediated by NADPH oxidase Activity in a Murine Model of Sleep Apnea" PLoS ONE, vol. 6, Issue 5, May 2011; Chia-Hung Hsieh et al., "NADPH oxidase Subunit 4-Mediated Reactive Oxygen species Contribute to Cycling Hypoxia-Promoted Tumor Progression in Glioblastoma Multiforme" PLoS ONE, vol 6, issue 9, September 2011; Sedeek M et al., "Molecular mechanisms of hypertension: role of nox family NADPH oxidase" Current Opinion in Nephrology and Hypertension 2009; Augusto C et al., "Novel Nox homologues in the vasculature: focusing on Nox4 and Nox5" Clinical Science 2011; Briones A M et al., "Differential regulation of Nox1, Nox2 and Nox4 in vascular smooth muscle cells from WKY and SHR" Journal of the American Society of Hypertension 5:3, 2011).

It has been recently shown that the Nox enzymes and particularly Nox4 are highly involved in pulmonary fibrosis. The function of oxidative stress in fibrosis are well recognized (Kinnula V L, Fattman C L, Tan R J, Oury T D (2005) Oxidative stress in pulmonary fibrosis: a possible role for redox modulatory therapy. Am J Respir Crit Care Med 172:417-422), as there is a substantial and growing body of evidence indicating that oxidative stress plays an important role in the pathological development of lung fibrosis as well as fibrosis in multiple organ systems (Kuwano K, Nakashima N, Inoshima I, Hagimoto N, Fujita M, Yoshimi M, Maeyama T, Hamada N, Watanabe K, Hara N (2003) Oxidative stress in lung epithelial cells from patients with idiopathic interstitial pneumonias. Eur Respir J 21:232-240). Thus, Nox enzymes and particularly Nox4 appear to be involved also in lung infections, acute lung injury, pulmonary arterial hypertension, obstructive lung disorders, fibrotic lung disease, and lung cancer.

NADPH oxidase isoenzymes, similarities, differences and function—All the seven iso-enzymes of NADPH oxidase (identified) are similar in the way of having NADPH and FAD binding site and six trans-membrane domains and in that they include two heme complexes. All the NADPH oxidase forms use the same basic mechanism to generate reactive oxygen, but the subcellular localizations and the modes of actions differ significantly. The reactive oxygen species produced by the enzymatic Nox-family are either superoxide $O_2^-$ or hydrogen peroxide $H_2O_2$.

Nox1 and 2 are constitutively attached to p22phox and to activate the enzyme complex other components such as Rac, p47phox, p67phox are required for full Nox1 activity. Nox2 needs Rac, p40phox, p47phox and p67phox for full activation. Nox1 and 2 generate $O_2^-$ when activated.

Nox3 also needs to assemble cytosolic proteins to be active (Cheng et al., J Biol Chem, 279(33), 2004).

Nox4 is also associated with p22phox, and is constitutively active in this form. Nox4 activity is, however, regulated through expression—not through assembly or ligand activation, which distinguishes this isoform from other isoforms (Serrander et al., Biochem J. 406, 2007). When induced, Nox4 is generally expressed at higher level than Nox1 and 2 (Ago et al., Circulation, 109, 2004). Nox4 seems to mainly generate $H_2O_2$ instead of $O_2^-$ as the other Nox-variants (Takac et al., J. Biol. Chem. 286, 2011). This makes this isoform unique because $H_2O_2$ has the ability to cross membranes and thus to act at longer distance than $O_2^-$ that has a very short half-life.

Nox5, Doux1 and Doux2 are activated by $Ca^{2+}$ (De Deken, Wang et al., J. Biol Chem., 275(30), 2000).

Nox4 is ubiquitously expressed in many cell-types although at a very low level until induced. It is, however mainly found in kidney, endothelial cells, adventitial fibroblasts, placenta, smooth muscle cells, osteoclasts and is the predominant Nox that is expressed in tumors (Chamseddine et al., Am J Physiol Heart Circ Physiol. 285, 2003; Ellmark et al., Cardiovasc Res. 65, 2005; Van Buul et al., Antioxid Redox Signal. 7, 2005; Kawahara et al., BMC Evol Biol. 7, 2007; Krause et al., Jpn J Infect is. 57(5), 2004; Griendling, Antioxid Redox Signal. 8(9), 2006). It was found that Nox4 was overexpressed in the majority of breast cancer cell-lines and primary breast tumors. Overexpression of Nox4 in already transformed breast tumor cells showed increased tumorigenicity, and Nox4 was here identified in the mitochondria. Nox4 was suggested as a target to treat breast cancer (Graham et al., Cancer Biol Ther 10(3), 2010). Nox4 has been reported being important as a mitochondrial energetic sensor taking part in metabolic reprogramming resulting in drug resistance of cancer and thus a potential therapeutic target (Shanmugasundaram et al., Nat Comm. 2017 Oct. 19; 8(1):997). The detrimental role of Nox4, via ROS-mediated programmed cell death and inflammation, in acute kidney injury induced at cancer treatment with cisplatin, has been reported (Lab Invest. 2018 January; 98(1):63-78).

Ischemia-reperfusion injury is the results of an inflammatory process that follows transient reduction of blood flow and then restored blood-flow (reperfusion). Renal ischemia-reperfusion injury is a major cause of renal failure that leads to acute kidney injury, patient morbidity and mortality. Tubular cell death by necrosis and apoptosis is central feature of renal ischemia-reperfusion injury with Nox4 and Nox2 playing a potential role in the pathogenesis (Simone et al., Free Radic Biol Med 2014 September; 74:263-73).

Nox4 mediates oxidative stress and apoptosis caused by TNF-α in cerebral vascular endothelial cells (Basuroy et al., Am J Physiol Cell Physiol vol. 296, 2009). Its adverse effect following ischemic stroke is well demonstrated in animal models and human tissue. Knockdown experiment, of Nox4, dramatically reduced the area of neuronal damage (Sedwick, PLos Biology, vol. 8 issue 9, 2010; Kleinschnitz et al., vol. 8 issue 9, 2010).

It was demonstrated through knockdown and overexpression studies in both microvascular and umbilical vein endothelial cells that increased Nox4 activity plays an important role in proliferation and migration of endothelial cells (Datla et al., Arterioscler Throm Vasc Biol. 27(11), 2007). Initially it was believed that Nox2 was responsible for the angiogenic defects in diabetes but the focus has shifted more towards Nox4 (Zhang et al., PNAS, 107, 2010; Garriodo-Urbani et al., Plos One 2011; Takac et al., Curr Hypertens Rep, 14, 2012). Nox4 also plays a key role in epithelial cell death during development of lung fibrosis (Camesecchi et al., Antiox Redox Signal. 1:15(3), 2011).

It further was demonstrated that siRNA-mediated knockdown of Nox4 significantly reduces NADPH oxidase activity in purified mitochondria from mesangial cells and kidney cortex. The knockdown blocked glucose-induced mitochondrial superoxide generation. It was suggested that Nox4 acts as a central mediator to oxidative stress that may lead to mitochondrial dysfunction and cell injury in diabetes (Block et al., PNAS vol. 106, no. 34, 2009).

It also was demonstrated that Nox4 was systemically up-regulated at diet-induced obesity in rats (Jiang, redox rep, 16(6), 2011). Further research demonstrated that certain Nox4 inhibitors counteract glucose intolerance in high-fat diet-treated C57BL/6 mice and these inhibitors were also shown to protect human islets cells exposed to high glucose combined with palmitate (Anvari E et al., Free Radical Res. 2015; 49 (11): 1308-18; Wang et al., PLoS One, 2018 Sep. 28; 13(9)).

Nox4 has been strongly connected to the pathology in failing hearts. (Nabeebaccus A et al. "NADPH oxidases and cardiac remodeling" Heart Fai Rev. 2011; Kuroda J et al., "NADPH oxidase and cardiac failure Cardiovasc Transl Res. 2010; Kuroda J et al., "NADPH oxidase 4 is a major source of oxidative stress in the failing heart" Proc Natl Acad Sci USA 2010). A connection between increased mitochondrial Nox4 activity and dysfunction of "the aging heart" has been suggested (Tetsuro Ago et al., AGING, December 2010, vol. 2 No 12).

Extracellular matrix accumulation contributes to the pathology of chronic kidney disease. The growth factor IGF-I activity is a major contributor to this process and Nox4 is a mediator in this process (New et al., Am J Physiol Cell Physiol. 302(1), 2012). The connection between chronic activation of the renin-angiotensin and the progression of kidney damage system is well established with Nox4 and Angiotensin II as collaborators in this process (Chen et al., Mol Cell Biol. 2012).

Diabetic retinopathy (DR) is one of the serious complications of diabetes. DR is the major cause of sight-loss and cause of blindness in the world and has a strong association with prolonged duration of diabetes, hyper-glycaemia and hypertension (Wong et al, Nat Rev Dis Primers, 2016 Mar. 17; 2: 16012). The pathogenesis of DR is not completely clear. Increased micro vascular growth has been considered as the initiating step (Antonetti et al., N Engl. J Med 2012 mar 29; 366(13):1227-39) but evidence has suggested that neurodegeneration may occur before microvascular changes in preclinical (Carpineto et al., Eye (Lond). 2016 May; 30(5): 673-9).

NADPH oxidase is considered as a potential target in treating diabetic retinopathy and specifically the iso form Nox4 has been connected to retinal cell damage (Peng et al., "Diabetic retinopathy: Focus on NADPH oxidase and its potential as therapeutic target" Eur J Pharmacol. 2019 Apr. 19; 853:381-387; Jiao et al., "Activation of the Notch-Nox4-reactive oxygen species signaling pathway induces cell death in high glucose-treated human retinal endothelial cells". Mol Med Rep. 2019 January; 19(1):667).

Acute intensive insulin therapy causes a transient worsening of diabetic retinopathy mediated by Nox4 (Poulaki V et al., "Acute intensive insulin therapy exacerbates diabetic blood-retinal breakdown via hypoxia-inducible factor-1 alpha and VEGF, J Clin Invest 109: 805-815, 2002; Meng et al., "NADPH Oxidase 4 mediates Insulin-Stimulated HIF-1 a and VEGF Expression, and Angiogenesis in Vitro", PLoS One, October 2012, vol 7, issue 10).

Fibrotic diseases are characterized by the appearance of myofibroblasts, and by excess accumulation of extracellular matrix with resultant tissue contraction and impaired function. Myofibroblasts are generated by fibroblast-myofibrobalst conversion, and in certain tissues through epithelial-mesenchymal transition (EMT), a process through which an epithelial cell changes its phenotype to become more like a mesenchymal cell, and for which process transforming growth factor beta (TGFbeta) is believed to play a central role. Recently, several studies have reported that epithelial-mesenchymal transition (EMT) contributes to various fibrotic diseases of the kidney (Zeisberg M, et al., Nat Med. 2003; 9:964-968), lung (Kim K K et al., Proc Natl Acad Sci USA. 2006; 103:13180-13185) and liver (Zeisberg M, et al., J Biol Chem. 2007; 282:23337-23347). Saika S et al. have proposed EMT as a therapeutic target for prevention of ocular tissue fibrosis (in Endocr Metab Immune Disord Drug Targets. 2008 March; 8(1):69-76. EMT has also been implicated in human ocular chronic graft-versus-host disease (Ogawa Y, et al. Epithelial mesenchymal transition in human ocular chronic graft-versus-host disease. Am J Pathol. 2009; 175(6):2372-2381).

Furthermore, proliferative vitreoretinopathy (PVR) is a complication of retinal detachment (RD) and is the primary cause of surgical failure following RD treatment. PVR is characterized by the formation of fibrotic tissue on the detached retina, which hinders retinal reattachment and can potentially cause blindness. Retinal pigment epithelial (RPE) cells are a major component of the fibrotic membrane and transform into fibroblast-like cells through epithelial-to-mesenchymal transition (EMT). It has been shown that RPE cells express Nox (e.g. Nox2 and 4) under normal physiological conditions. Consequently, it has been suggested that Nox inhibitors may have a potential use for the treatment and prevention of PVR (Jing Y. et al., Int J Mol Med. 2018 July; 42(1): 123-130).

Using a well-characterised in vitro model of epithelial to mesenchymal transition (EMT) in rat lens epithelial explants (Hales A M et al., Investigative ophthalmology & visual science. 1995; 36(8):1709-13; Liu J, et al., Investigative ophthalmology & visual science. 1994; 35(2):388-401.), it has been previously shown that TGFβ is capable of upregulating Nox4 expression, and concomitant production of reactive oxygen species (ROS) (Das S J, Investigative ophthalmology & visual science. 2016; 57(8):3665-73). Further, it has been shown that pharmacological inhibition of Nox4 activity with a Nox4 and Nox2 selective inhibitor, retards the progression of EMT and also abrogates the expression of the myofibroblast marker, alpha Smooth-Muscle-Actin (aSMA) (Das S J, et al., vide supra).

Traumatic brain injury (TBI) is a major cause of death and disability worldwide. The need for a neuro-protecting agent is therefore large. The TBI pathology evolves minutes to years following the initial injury. Oxidative stress is the main driving force in a complex cascade of secondary injury mechanisms and strongly contributes to neuro-degeneration and neuro-inflammation. Deletion studies of Nox2 and Nox4 have revealed that these targets can reduce oxidative stress, attenuate neuro-inflammation and protect neurons and preserve function capacity of the object (Ma et al., "NADPH oxidase 2 regulates NLRP3 inflammasome activation in the brain after traumatic brain injury", Oxid Med. Cell Longev. 2017 60576009; Dohi et al., "Gp91phox(Nox2) in classical activated microglia exacerbates traumatic brain injury", J Neuroinflamm. 7 (2010) 41; Wang et al., "Regulatory role of NADPH oxidase 2 in the polarization dynamics and neurotoxicity of microglia/macrophages after traumatic brain injury". Free Radic. Biol. Med. 113 (2017) 119-131; Kumar et al., "Nox2 drives Ml-like microglia/macrophage activation and neurodegeneration following experimental traumatic brain injury", Brain Behav. Immun. 58 (2016) 291-309); Ma et al., "Deletion of NADPH oxidase 4 reduces severity of traumatic brain injury, Free Radic. Biol. Med. 117 (2018) 66-75; Lo et al., "NADPH oxidase inhibition improves neurological outcomes in surgical-induced brain injury", Neurosci. Lett. 414 (2007) 228-232; Chadran et al., "A combination antioxidant therapy to inhibit Nox2 and activate Nrf2 decreases secondary brain damage and improves functional recovery after traumatic brain injury" J. Cereb. Blood Flow. Metab. (2017)).

From the above, it appears that the Nox enzymes, in particular Nox2 and Nox4, have several functions in the living body, and that they may also be involved in various disorders. Examples of such diseases and disorders are cardiovascular disorders, respiratory disorders, metabolism disorders, endocrine disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, such as traumatic head injury, septic, hemorrhagic and anaphylactic shock, diseases or disorders of the gastrointestinal system, angiogenesis, angiogenesis-dependent conditions. It also appears that especially Nox4 has been found to be involved in such disorders. Consequently, it is considered that compounds capable of inhibiting Nox, and in particular compounds capable of selectively inhibiting Nox4, would be of great interest for use in the treatment of diseases and disorders involving Nox enzymes, and in particular Nox2 and Nox4.

As noted herein above, Nox4 is involved in stroke, among other diseases. Stroke is the second leading cause of death worldwide and survivors often are disabled with serious cognitive difficulties affecting social life as well as the ability to perform work. In addition to the suffering of the patients and the close relatives this also is extremely costly to society and the healthcare system. Without new efficient treatment of stroke patients, the cost to care for stroke victims during the next 45 years will exceed $2.2 trillion in the US only.

Stroke is classified into two major categories. Ischemic that causes interruption of blood supply and hemorrhagic that results from rupture of a blood vessel. Both induce rapid loss of brain function caused by disturbances in blood supply. Ischemic stroke is by far the most common form accounting for 87% of the cases, while 9% are due to intracerebral hemorrhage and the remaining 4% are due to subarachnoid hemorrhage.

The pathophysiology of ischemic stroke is complex and the patient recovery is dependent on the length in time that neuronal tissues are deprived of blood supply. Brain tissues deprived of oxygen for more than three hours will be irreversibly damaged. The pathophysiology includes excitotoxicity mechanisms, inflammatory pathways, oxidative damage, ionic imbalances, apoptosis, angiogenesis and endogenous neuron protection. Additionally when white blood cells re-enter a previously hypo perfused region via returning blood, they can occlude small vessels, producing additional ischemia.

Different strategies to manage stroke are to identify risk groups for preventive treatment and by development, implementation and dissemination of evidence-based clinical practice guidelines in order to set a standard for stroke management through the continuum of care with early treatment that is fundamental to improve the outcome following an ischemic stroke attack.

One of two approved treatments today is iv administration of tissue plasminogen activator (tPA) that will induce thrombolysis, which may remove the clot and restore blood supply to the brain tissue. The other method is to mechanically remove the clot, to restore blood supply. Other approaching methods are in early phase research and some in clinical trials. New potential therapies of interest include administration of neuroprotective agents, cooling of the ischemic brain and the use of stents to revasculate occluded arteries.

Thus, a method of treatment an ischemic stroke attack generally comprises removing mechanical hinders (blood clots) from the blood flow, e.g. by intravenous administration of tissue plasminogen activator (tPA). It is thought that combining the removal of mechanical hinders from the blood flow with administration, either before or after, of neuroprotective agents, may help saving ischemic neurons in the brain from irreversible injury, including apoptosis. However, as of today no neuroprotective agent has been provided for successful treatment of stroke. It therefore appears that there still is a need for improved treatment of stroke, in particular improved treatment by administration of neuroprotective agents, preferably in combination with the removal of blood clots in the ischemic brain.

Nox2 has been shown to be involved in various human pathologies such periphery artery disease (Loffredo L. et al., Int J Cardiol 2013; 165: 184-192), acute myocardial infarction (Krijnen P A, et al., J Clin Pathol 2003; 56: 194-199) and neurodegenerative disorders (Sorce S.; Antioxid Redox Signal 2009; 11: 2481-2504), vascular injury during diabetic retinopathy (Rojas, M. et al. PLOS ONE. 8 (12): e84357). Further, Schiavone S et al. in Translational Psychiatry volume 6, page e813 (2016) present evidence that an increase in Nox2-derived oxidative stress in the brain might be involved in the neuropathological pathways leading to suicidal behaviour.

International application No. PCT/EP2015/079586 (WO 2016/096720) discloses certain sulfonamide derivatives that are Nox inhibitors, in particular Nox4 inhibitors. International application No. PCT/US2006/049117 (WO 2007/076055) discloses some sulfonamide derivatives as proteinase activated receptor antagonists, and mentions the two compounds 4-butyl-N-[2-(2-ethoxyphenyl)ethyl]benzene-1-sulfonamide and 3,4-dichloro-N-[2-(2-ethoxyphenyl)ethyl]benzene-1-sulfonamide. Fernandez D., et al. in European Journal of Medicinal Chemistry vol. 44, (2009), 3266-3271, disclose five-membered heterocyclic compounds tested as inhibitors of basic metallocarboxypeptidases, and mention the compound 3-methyl-N-(2-methylphenethyl)-4-(1H-tetrazol-1-yl)benzenesulfonamide.

Sulfonamides also have been disclosed as synthetic intermediates. Thus, for this purpose U.S. patent application Ser. No. 12/357,725 (publication No. 2009/0176804) discloses 5-bromo-2-chloro-N-[2-(2-methoxy-phenyl)-ethyl]-benzenesulfonamide and 5-bromo-2-chloro-N-[2-(2-trifluoromethoxy-phenyl)-ethyl]-benzenesulfonamide; U.S. patent application Ser. No. 11/862,818 (publication No. 2008/0090821) discloses N-[2-(2-methoxyphenyl)-ethyl]-4-methylbenzenesulfonamide and N-[2-(2-hydroxyphenyl)ethyl]-4-methylbenzenesulfonamide; N-(2-iodophenethyl)-4-methylbenzenesulfonamide is disclosed by Aronica L., et al. in Eur. J. Org. Chem. 2017, 955-963; N-(2-bromophenethyl)-4-methylbenzenesulfonamide is disclosed by Priebbenow D. et al., in Tetrahedron 53 (2012), 1468-1471; and Henderson L. et al., in Tetrahedron 53 (2012), 4657-

4660, disclose 4-methyl-N-(2-(2',3',4',5'-tetrahydro-[1,1'-biphenyl]-2-yl)ethyl)benzenesulfonamide.

SUMMARY OF THE INVENTION

As mentioned herein above, some sulfonamide derivatives have been previously described for use as Nox4 inhibitors. However, there is still a need for compounds having an improved Nox4 inhibiting activity preferably in combination with high selectivity for Nox4 over one or more other enzymes of the Nox family. The present inventors now have identified novel sulfonamide derivatives having surprisingly high Nox4 inhibiting activity, advantageously coupled with very high selectivity for Nox4. Such characteristics may allow for the use of the inventive compounds in the treatment of disorders involving Nox4 activity, e.g. any of the disorders as mentioned herein above.

The present inventors also surprisingly have found that some of the sulfonamide derivatives provided herein have a high Nox2 inhibiting activity advantageously coupled with a high selectivity for Nox2. Such activity may allow for the use of the inventive compounds in the treatment of disorders involving Nox2 activity, e.g. any of the disorders as mentioned herein above.

In some embodiments, compounds are provided having both Nox2 and Nox4 activity, advantageously coupled with high selectivity for Nox2 and Nox4 over other members of the Nox family. Thus, in some embodiments, compounds are provided capable of inhibiting at least one of Nox2 and Nox4 and having a high selectivity for at least one of Nox2 and Nox4 over other Nox enzymes, e.g. one or more of Nox1, Nox3 and Nox5. In some advantageous embodiments, compounds are provided capable of inhibiting both Nox2 and Nox4 and having a high selectivity for both Nox2 and Nox4 over other Nox enzymes.

Advantageously, the selective Nox2 and/or Nox4 inhibiting activity of compounds of the invention also may preferably be accompanied by lack of inner redox activity as well as a lack of inhibition of xanthine oxidase or glucose oxidase.

A first aspect therefore is a compound according to formula (I)

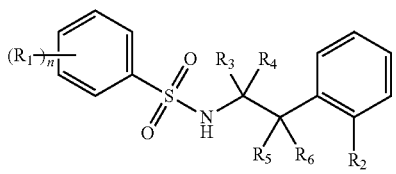

(I)

or a pharmaceutically acceptable salt thereof, wherein
n is an integer of from 1 to 5;
each $R_1$ is independently selected from C1-C6 alkyl, C3-C6 carbocyclyl, C3-C6 carbocyclyl-C1-C3 alkyl, C1-C6 alkoxy, C1-C6 alkoxy-C1-C3 alkyl, C3-C6 carbocyclyloxy, C3-C6 carbocyclyloxy-C1-C3 alkyl, 4- to 6-membered heterocyclyl, 4- to 6-membered heterocyclyl-C1-C3 alkyl, hydroxy, hydroxy-C1-C3 alkyl, carboxy, carboxy-C1-C3 alkyl, C1-C6 alkoxycarbonyl, C1-C6 alkoxycarbonyl-C1-C3 alkyl, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties independently selected from C1-C3 alkyl and halogen;
$R_2$ is selected from C1-C6 alkyl, C3-C6 carbocyclyl, C3-C6 carbocyclyl-C1-C3 alkyl, C1-C6 alkoxy, C1-C6 alkoxy-C1-C3 alkyl, C3-C6 carbocyclyloxy, C3-C6 carbocyclyloxy-C1-C3 alkyl, halogen, hydroxy, and hydroxy-C1-C3 alkyl;
$R_3$, $R_4$, $R_5$, and $R_6$ are independently selected from H and F;
any alkyl is optionally substituted with one or more halogens; and
any carbocyclyl or heterocyclyl is optionally substituted with one or more moieties independently selected from halogen and C1-C3 alkyl;
provided that the compound is not
4-butyl-N-[2-(2-ethoxyphenyl)ethyl]benzene-1-sulfonamide,
3,4-dichloro-N-[2-(2-ethoxyphenyl)ethyl]benzene-1-sulfonamide,
5-bromo-2-chloro-N-[2-(2-methoxy-phenyl)-ethyl]-benzenesulfonamide,
5-bromo-2-chloro-N-[2-(2-trifluoromethoxy-phenyl)-ethyl]-benzenesulfonamide,
N-[2-(2-methoxyphenyl)-ethyl]-4-methylbenzenesulfonamide,
N-[2-(2-hydroxyphenyl)ethyl]-4-methylbenzenesulfonamide,
N-(2-iodophenethyl)-4-methylbenzenesulfonamide,
N-(2-bromophenethyl)-4-methylbenzenesulfonamide,
4-methyl-N-(2-(2',3',4',5'-tetrahydro-[1,1'-biphenyl]-2-yl)ethyl)benzenesulfonamide, or
3-methyl-N-(2-methylphenethyl)-4-(1H-tetrazol-1-yl)benzenesulfonamide.

A further aspect relates to a compound of formula (I), as defined herein, for use in therapy. In some embodiments, the therapy is directed to treatment of a human patient, i.e. the compound of formula (I) is for human (pharmaceutical) use. In some other embodiments, the therapy is directed to the treatment of a non-human mammal, such as a pet animal, i.e. the pharmaceutical use is of veterinary type.

In another aspect, a pharmaceutical composition is provided, comprising a compound of formula (I) or a pharmaceutically acceptable salt of said compound, and optionally a pharmaceutically acceptable excipient. In some embodiments, the pharmaceutical composition is for human use, i.e. for the treatment of a human subject. In some other embodiments, the pharmaceutical composition is a veterinary composition, suitable for the treatment of an animal, such as e.g. a dog or a cat.

According to one aspect, the compound of formula (I), or a pharmaceutically acceptable salt thereof, is provided for use in the treatment of diseases associated with, e.g. caused or driven by, elevated activity of at least one of (i.e. one or both of) Nox2 and Nox4.

According to another aspect, the compound of formula (I), or a pharmaceutically acceptable salt thereof, is provided for use in the treatment of diseases associated with, e.g. caused or driven by, elevated Nox4 activity. Examples of such conditions and disorders related to Nox4 activity are those mentioned herein above as related to or mediated by Nox4, for example conditions and disorders selected from endocrine disorders, cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, diseases or disorders of the gastrointestinal system, abnormal angiogenesis and angiogenesis-dependent conditions, lung infections, acute lung injury, pulmonary arterial hypertension, obstructive lung disorders, and fibrotic lung disease.

According to another aspect, the compound of formula (I), or a pharmaceutically acceptable salt thereof, is provided for use in the treatment of diseases associated with, e.g. caused or driven by, elevated Nox2 activity. Examples of such conditions and disorders related to Nox2 activity are those mentioned herein above as related to or mediated by Nox2, for example conditions and disorders selected from periphery artery disease, acute myocardial infarction, and neurodegenerative disorders, vascular injury during diabetic retinopathy, and psychiatric diseases, in particular associated with suicide.

According to one aspect, there is provided a method for the treatment of a disorder as mentioned herein above, comprising administering a therapeutically effective amount of a compound of formula (I) to a mammal patient in need of such treatment. In some embodiments, the disorder is selected from endocrine disorders, cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, diseases or disorders of the gastrointestinal system, abnormal angiogenesis and angiogenesis-dependent conditions, lung infections, acute lung injury, pulmonary arterial hypertension, obstructive lung disorders, and fibrotic lung disease.

According to one aspect, there is provided a method of inhibiting the activity of Nox4, in a mammal in need thereof, by administering to said mammal a compound of formula (I), or a pharmaceutically acceptable salt of said compound.

According to one aspect, a compound of formula (I) is provided for use in the treatment of stroke, e.g. ischemic stroke.

According to a further aspect, a compound of formula (I) is provided for use as a neuroprotective agent in the treatment of stroke, e.g. ischemic stroke.

According to one aspect, there is provided a method of inhibiting the activity of Nox2, in a mammal in need thereof, by administering to said mammal a compound of formula (I), or a pharmaceutically acceptable salt of said compound.

According to a further aspect, there is provided a method of inhibiting the activity of at least one of Nox2 and Nox4, in a mammal in need thereof, by administering to said mammal a compound of formula (I), or a pharmaceutically acceptable salt of said compound.

According to one aspect, the use of a compound of formula (I) is provided, for the manufacturing of a medicament for the treatment of any of the disorders mentioned herein.

DETAILED DESCRIPTION OF THE INVENTION

Figure 1:
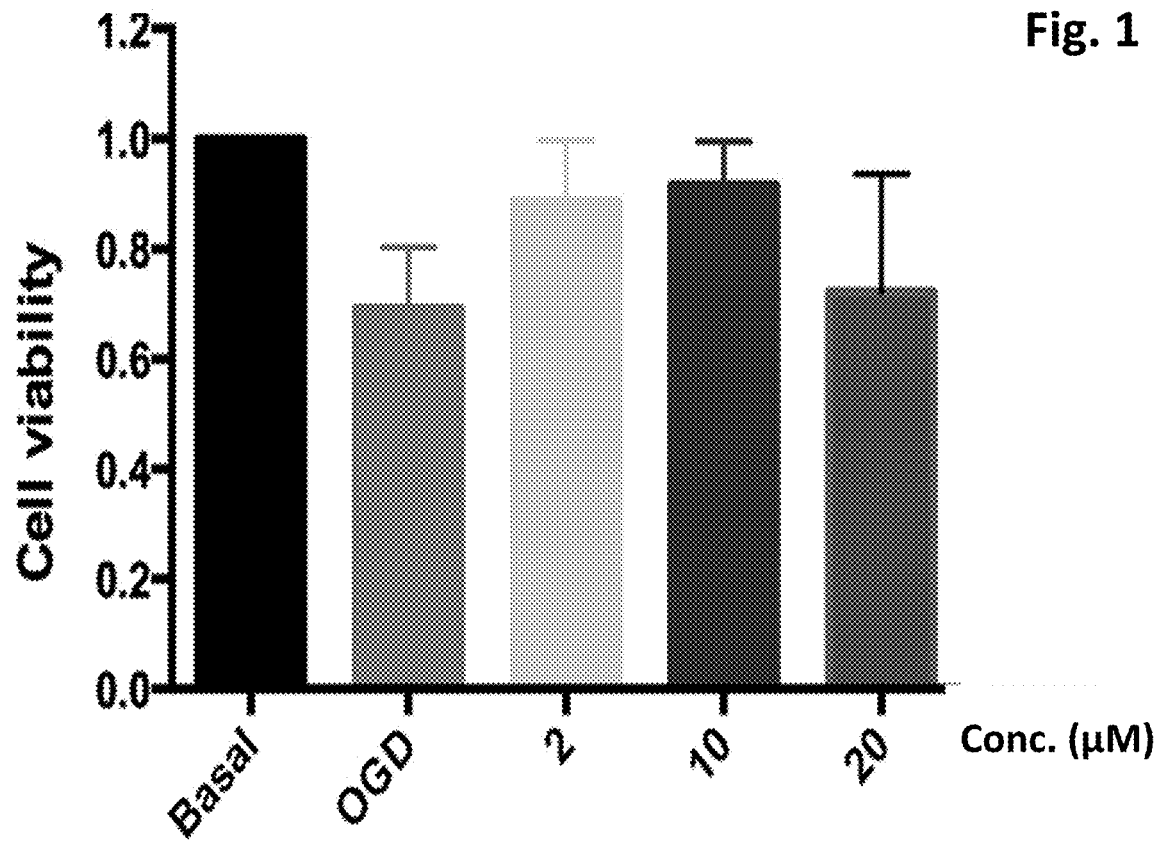
FIG. 1 is a bar chart showing cell viability as a ratio of basal cell viability of human brain microvascular endothelial cells subjected to hypoxia and starvation (OGD: oxygen and glucose deprivation) for 5 h and then cultured for 24 h in the absence or presence of Example 11 at a concentration of 2, 10 or 20 µM. Basal=no hypoxia or starvation, cells cultured in the presence of culture medium only. OGD=5 h of hypoxia or starvation, cells cultured in the presence of culture medium only.
Figure 2:
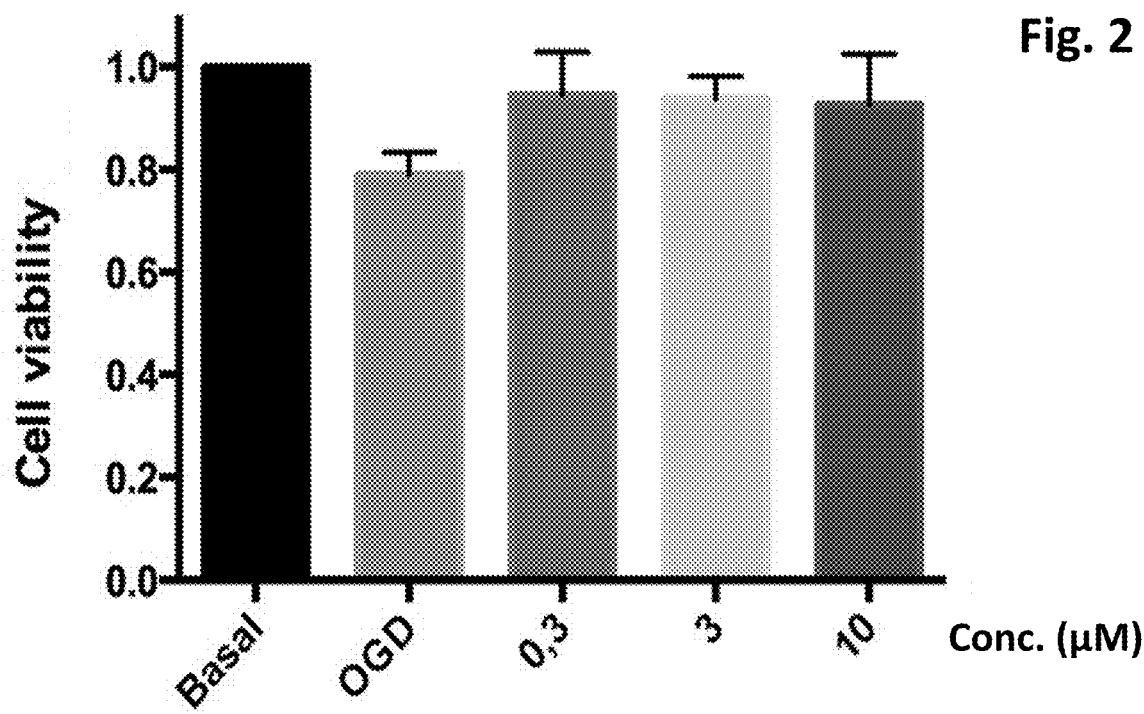
FIG. 2 is a bar chart showing cell viability as a ratio of basal cell viability of human brain microvascular endothelial cells subjected to hypoxia and starvation (OGD) for 5 h and then cultured for 24 h in the absence or presence of Example 17 at a concentration of 0.3, 3 or 10 µM. Basal=no hypoxia or starvation, cells cultured in the presence of culture medium only. OGD=5 h of hypoxia or starvation, cells cultured in the presence of culture medium only.
Figure 3:
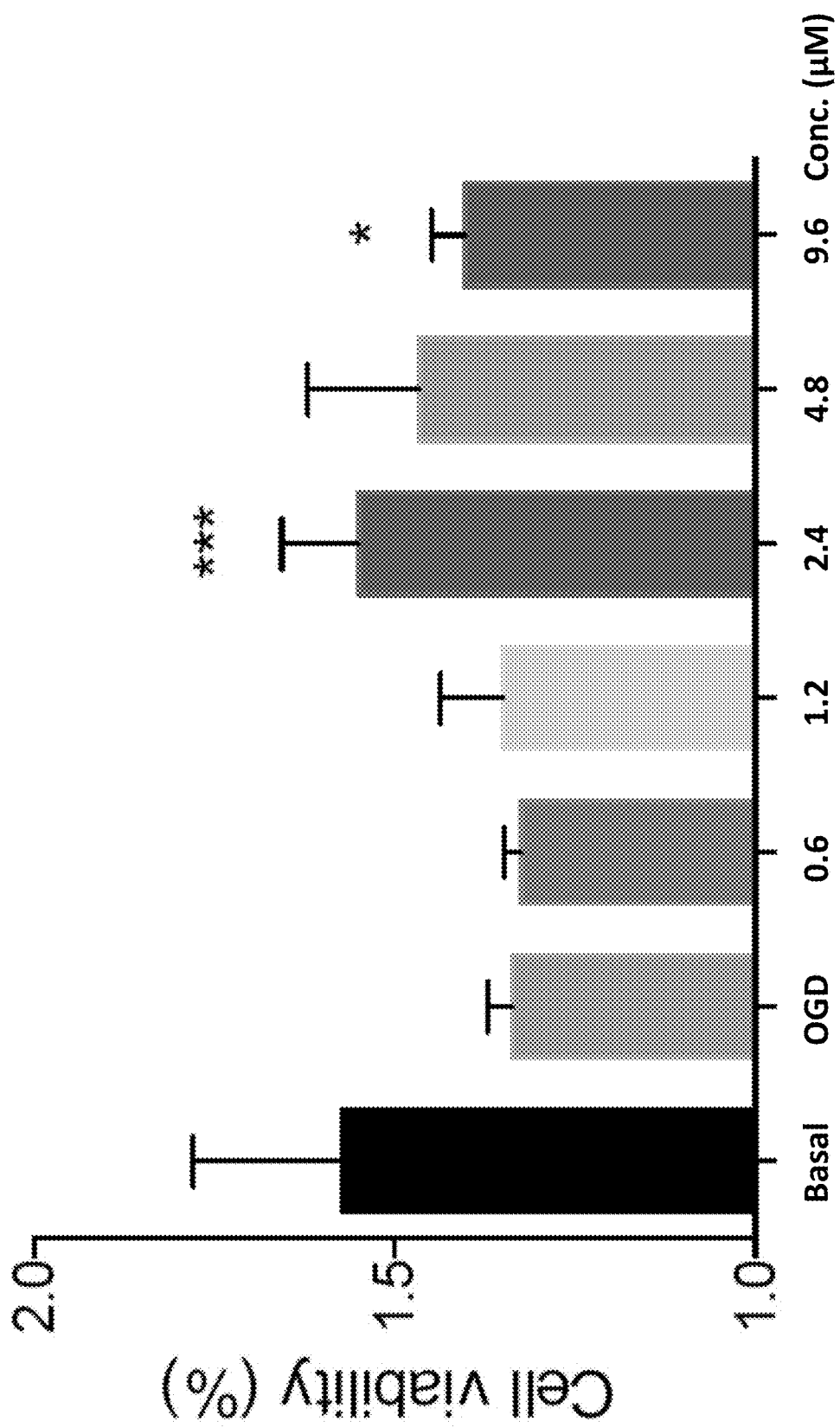
FIG. 3 is a bar chart showing cell viability as a ratio of basal cell viability of human brain microvascular endothelial cells subjected to hypoxia and starvation (OGD: oxygen and glucose deprivation) for 6 h and then cultured for 24 h in the absence or presence of Example 44 at a concentration of from 0.6 to 9.6 µM. Basal=no hypoxia or starvation, cells cultured in the presence of culture medium only. OGD=6 h of hypoxia or starvation, cells cultured in the presence of culture medium only ($*p<0.05$, $***p<0.001$).
Figure 4:
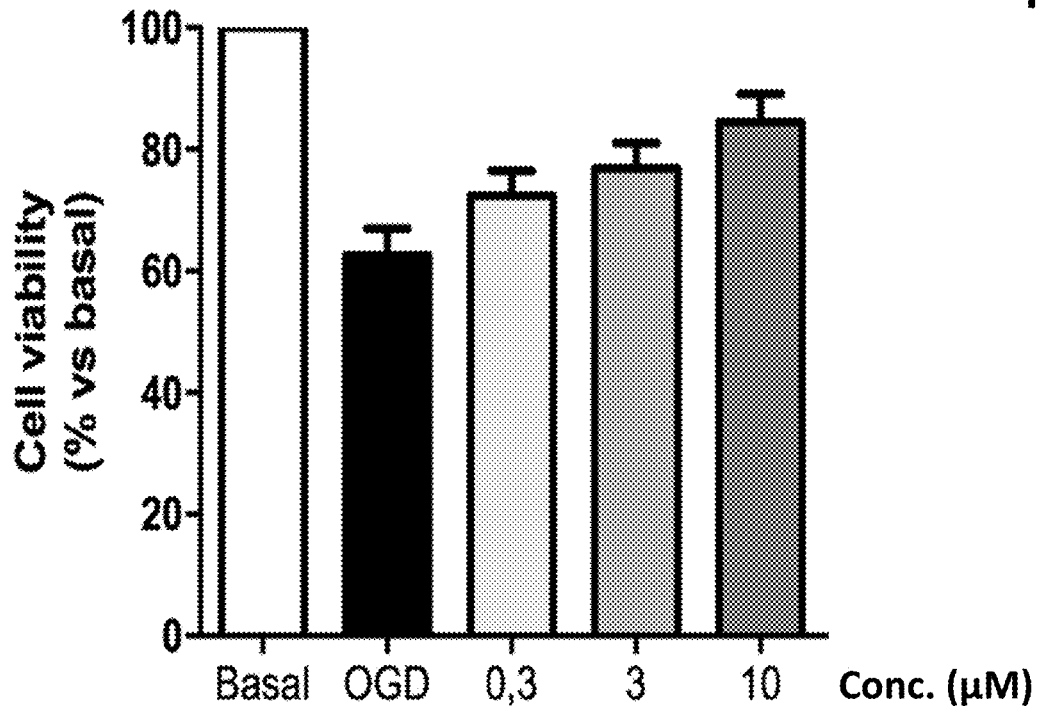
FIG. 4 is a bar chart showing cell viability (in % of basal cell viability) of hippocampal brain slices subjected to hypoxia and starvation for 5 h and then cultured for 24 h in the absence (OGD) or presence of Example 11 at a concentration of 0.3 µM, 3 µM, or 10 µM. Basal=no hypoxia or starvation, cells cultured in the presence of culture medium only. OGD=5 h of hypoxia or starvation, cells cultured in the presence of culture medium only.
Figure 5:
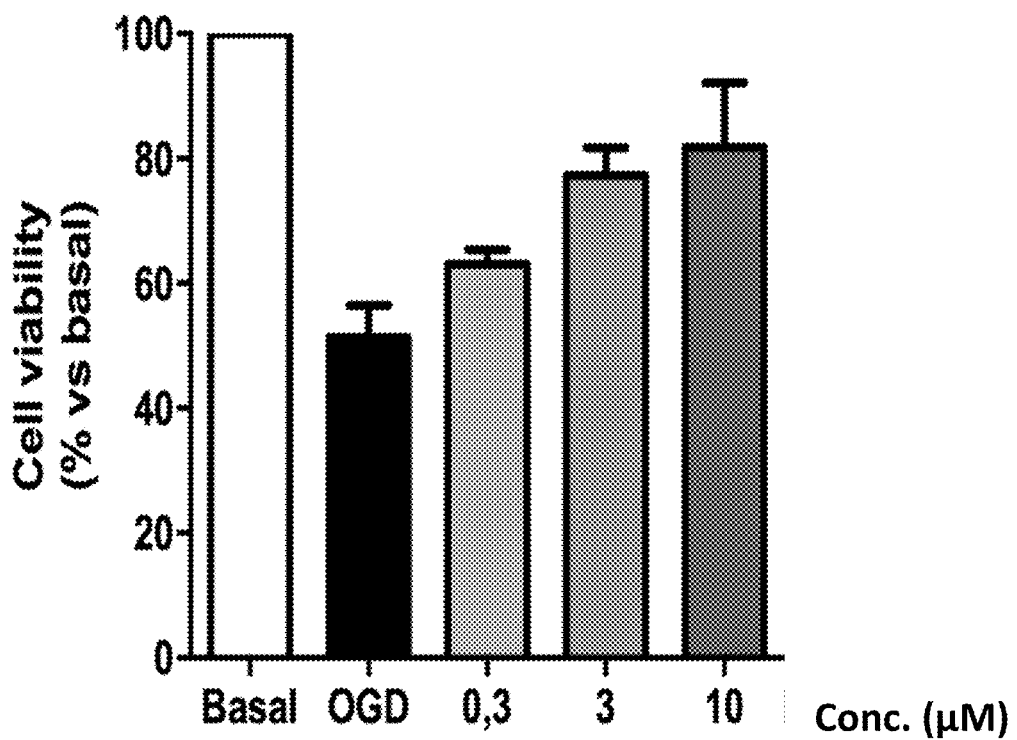
FIG. 5 is a bar chart showing cell viability (in % of basal cell viability) of hippocampal brain slices subjected to hypoxia and starvation for 5 h and then cultured for 24 h in the absence (OGD) or presence of Example 17 at a concentration of 0.3, 3 or 10 µM. Basal=no hypoxia or starvation, cells cultured in the presence of culture medium only. OGD=5 h of hypoxia or starvation, cells cultured in the presence of culture medium only.

In general any term used herein shall be given its normal meaning as accepted within the field to which the present invention belongs. For the sake of clarity, however, some definitions will be given herein below, and shall apply throughout the specification and the appended claims, unless otherwise specified or apparent from the context.

The term "endocrine disorder" refers to disorders of the endocrine system and may be as well endocrine gland hyposecretion as hypersecretion, or tumors of endocrine glands. Diabetes and polycystic ovarian syndrome are examples of endocrine disorders.

The term "cardiovascular disorder or disease" comprises atherosclerosis, especially diseases or disorders associated with endothelial dysfunction including but not limited to hypertension, cardiovascular complications of Type I or Type II diabetes, intimal hyperplasia, coronary heart disease, cerebral, coronary or arterial vasospasm, endothelial dysfunction, heart failure including congestive heart failure, peripheral artery disease, restenosis, trauma caused by a stent, stroke, ischemic attack, vascular complications such as after organ transplantation, myocardial infarction, hypertension, formation of atherosclerotic plaques, platelet aggregation, angina pectoris, aneurysm, aortic dissection, ischemic heart disease, cardiac hypertrophy, pulmonary embolus, thrombotic events including deep vein thrombosis, injury caused after ischemia by restoration of blood flow or oxygen delivery as in organ transplantation, open heart surgery, angioplasty, hemorrhagic shock, angioplasty of ischemic organs including heart, brain, liver, kidney, retina and bowel.

The term "respiratory disorder or disease" comprises bronchial asthma, bronchitis, allergic rhinitis, adult respiratory syndrome, cystic fibrosis, lung viral infection (influenza), pulmonary hypertension, idiopathic pulmonary fibrosis and chronic obstructive pulmonary diseases (COPD).

The term "allergic disorder" includes hay fever and asthma.

The term "traumatism" includes polytraumatism.

The term "disease or disorder affecting the metabolism" includes obesity, metabolic syndrome and Type II diabetes.

The term "skin disease or disorder" includes psoriasis, eczema, dermatitis, wound healing and scar formation.

The term "bone disorder" includes osteoporosis, osteoporosis, osteosclerosis, periodontitis, and hyperparathyroidism.

The term "neurodegenerative disease or disorder" comprises a disease or a state characterized by a central nervous system (CNS) degeneration or alteration, especially at the level of the neurons such as Alzheimer's disease, Parkinson's disease, Huntington's disease, amyotrophic lateral sclerosis, epilepsy and muscular dystrophy. It further comprises neuroinflammatory and demyelinating states or diseases such as leukoencephalopathies, and leukodystrophies.

The term "demyelinating" is referring to a state or a disease of the CNS comprising the degradation of the myelin around the axons. In the context of the invention, the term demyelinating disease is intended to comprise conditions which comprise a process that demyelinate cells such as multiple sclerosis, progressive multifocal leukoencephalopathy (PML), myelopathies, any neuroinflammatory condition involving autoreactive leukocyte within the CNS, congenital metabolic disorder, a neuropathy with abnormal myelination, drug induced demyelination, radiation induced demyelination, a hereditary demyelinating condition, a prion induced demyelinating condition, encephalitis induced demyelination or a spinal cord injury. Preferably, the condition is multiple sclerosis.

The term "kidney disease or disorder" includes diabetic nephropathy, renal failure, glomerulonephritis, nephrotoxicity of aminoglycosides and platinum compounds and hyperactive bladder. In a particular embodiment, the term according to the invention includes chronic kidney diseases or disorders.

The term "reproduction disorder or disease" includes erectile dysfunction, fertility disorders, prostatic hypertrophy and benign prostatic hypertrophy.

The term "disease or disorder affecting the eye and/or the lens" includes cataract including diabetic cataract, re-opacification of the lens post cataract surgery, diabetic and other forms of retinopathy.

The term "conditions affecting the inner ear" includes presbyacusis, tinnitus, Meniere's disease and other balance problems, utriculolithiasis, vestibular migraine, and noise induced hearing loss and drug induced hearing loss (ototoxicity).

The term "inflammatory disorder or disease" means inflammatory bowel disease, sepsis, septic shock, adult respiratory distress syndrome, pancreatitis, shock induced by trauma, bronchial asthma, allergic rhinitis, rheumatoid arthritis, chronic rheumatoid arthritis, arteriosclerosis, intracerebral hemorrhage, cerebral infarction, heart failure, myocardial infarction, psoriasis, cystic fibrosis, stroke, acute bronchitis, chronic bronchitis, acute bronchiolitis, chronic bronchiolitis, osteoarthritis, gout, myelitis, ankylosing spondylitis, Reuter syndrome, psoriatic arthritis, spondylarthritis, juvenile arthritis or juvenile ankylosing spondylitis, reactive arthritis, infectious arthritis or arthritis after infection, gonococcal arthritis, syphilitic arthritis, Lyme disease, arthritis induced by "angiitis syndrome," polyarteritis nodosa, anaphylactic angiitis, Luegenec granulomatosis, rheumatoid polymyalgia, articular cell rheumatism, calcium crystal deposition arthritis, pseudogout, non-arthritic rheumatism, bursitis, tendosynovitis, epicondyle inflammation (tennis elbow), carpal tunnel syndrome, disorders by repetitive use (typing), mixed form of arthritis, neuropathic arthropathy, hemorrhagic arthritis, vascular peliosis, hypertrophic osteoarthropathy, multicentric reticulohistiocytosis, arthritis induced by specific diseases, blood pigmentation, sickle cell disease and other hemoglobin abnormality, hyperlipoproteinemia, dysgammaglobulinemia, hyperparathyroidism, acromegaly, familial Mediterranean fever, Bechet's disease, systemic autoimmune disease erythematosus, multiple sclerosis and Crohn's disease or diseases like relapsing polychondritis, chronic inflammatory bowel diseases (IBD) or the related diseases which require the administration to a mammal in a therapeutically effective dose of a compound expressed by Formula (I) in a sufficient dose to inhibit NADPH oxidase.

The term "liver diseases or disorders" include liver fibrosis, alcohol induced fibrosis, steatosis and non-alcoholic steatohepatitis.

The term "arthritis" means acute rheumatic arthritis, chronic rheumatoid arthritis, chlamydial arthritis, chronic absorptive arthritis, anchylous arthritis, arthritis based on bowel disease, filarial arthritis, gonorrheal arthritis, gouty arthritis, hemophilic arthritis, hypertrophic arthritis, juvenile chronic arthritis, Lyme arthritis, neonatal foal arthritis, nodular arthritis, ochronotic arthritis, psoriatic arthritis or suppurative arthritis, or the related diseases which require the administration to a mammal in a therapeutically effective dose of a compound expressed by Formula (I) in a sufficient dose to inhibit NADPH oxidase.

The term "pain" includes hyperalgesia associated with inflammatory pain.

The term "cancer" means carcinoma (e.g., fibrosarcoma, myxosarcoma, liposarcoma, chondrosarcoma, osteogenic sarcoma, chordoma, angiosarcoma, endothelium sarcoma, lymphangiosarcoma, lymphangioendothelioma, periosteoma, mesothelioma, Ewing's tumor, leiomyosarcoma, rhabdomyo sarcoma, colon carcinoma, pancreatic cancer, breast cancer, ovarian cancer, renal cancer, prostatic carcinoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatocellular carcinoma, cholangiocarcinoma, choriocarcinoma, seminoma, embryonal carcinoma, Wilms' tumor, cervical cancer, orchioncus, lung cancer, small-cell lung cancer, lung adenocarcinoma, bladder cancer or epithelial cancer) or the related diseases which require the administration to a mammal in a therapeutically effective dose of a compound expressed by the Formula (I) in a sufficient dose to inhibit NADPH oxidase.

The term "disease or disorders of the gastrointestinal system", includes gastric mucosa disorders ischemic bowel disease management, enteritis/colitis, cancer chemotherapy, or neutropenia.

The term "angiogenesis" includes sprouting angio genesis, intussusceptive angiogenesis, vasculogenesis, arteriogenesis and lymphangiogenesis. Angiogenesis is the formation of new blood vessels from pre-existing capillaries or post-capillary venules and occurs in pathological conditions such as cancers, arthritis and inflammation. A large variety of tissues, or organs comprised of organized tissues, can support angiogenesis in disease conditions including skin, muscle, gut, connective tissue, joints, bones and the like tissue in which blood vessels can invade upon angiogenic stimuli. As used herein, the term "angiogenesis-dependent condition" is intended to mean a condition where the process of angiogenesis or vasculogenesis sustains or augments a pathological condition. Vasculogenesis results from the formation of new blood vessels arising from angioblasts which are endothelial cell precursors.

Both processes result in new blood vessel formation and are included in the meaning of the term angiogenesis-dependent conditions. Similarly, the term "angiogenesis" as used herein is intended to include de novo formation of vessels such as those arising from vasculogenesis as well as those arising from branching and sprouting of existing vessels, capillaries and venules.

The term "angiogenesis inhibitory", means which is effective in the decrease in the extent, amount, or rate of neovascularization. Effecting a decrease in the extent, amount, or rate of endothelial cell proliferation or migration in the tissue is a specific example of inhibiting angiogenesis. Angiogenesis inhibitory activity is particularly useful in the treatment of any cancers as it targets tumor growth process and in the absence of neovascularization of tumor tissue, the tumor tissue does not obtain the required nutrients, slows in growth, ceases additional growth, regresses and ultimately becomes necrotic resulting in killing of the tumor. Further, an angiogenesis inhibitory activity is particularly useful in the treatment of any cancers as it is particularly effective against the formation of metastases because their formation also requires vascularization of a primary tumor so that the metastatic cancer cells can exit the primary tumor and their establishment in a secondary site requires neovascularization to support growth of the metastases.

As used herein, "treatment" and "treating" includes prophylaxis of a named disorder or condition, or amelioration or elimination of the disorder once it has been established. Thus, treatment generally means obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease.

The term "subject" as used herein refers to mammals. Mammals contemplated by the present invention include humans and non-human mammals, such as primates, domesticated animals such as farm animals, e.g. cattle, sheep, pigs, horses and the like, as well as pet animals, such as dogs and cats, and the like.

"An effective amount" (or "therapeutically effective amount", etc) refers to an amount of a compound that confers a therapeutic effect on the treated subject. The therapeutic effect may be objective (i.e., measurable by some test or marker) or subjective (i.e., subject gives an indication of or feels an effect).

The term "inhibitor" used in the context of the invention is defined as a molecule that inhibits completely or partially the activity of another molecule, e.g. an enzyme.

"Pharmaceutically acceptable" means being useful in preparing a pharmaceutical composition that is generally safe, non-toxic and neither biologically nor otherwise undesirable and includes being useful for veterinary use as well as human pharmaceutical use.

The term "alkyl" either alone or as part of a radical, refers to straight or branched chain alkyl of the general formula $C_nH_{2n+1}$.

The expression "Cm-Cn" in connection with a moiety such as, for example, an alkyl or carbocyclyl, indicates that the moiety contains a number of carbon atoms ranging from m to n (where n is higher than m).

The term "Cm-Cn alkyl" refers to an alkyl containing from m to n carbon atoms, wherein n is an integer higher than m, and m is at least 1. For example, methyl is a C1 alkyl.

The term "Cm-Cn alkoxycarbonyl" refers to a moiety of formula

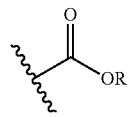

wherein R is a Cm-Cn alkyl group.

The term "Cm-Cn alkoxycarbonyl-Cp-Cq" alkyl refers to refers to a Cp-Cq alkyl group having one hydrogen atom replaced by a Cm-Cn alkoxycarbonyl group, i.e. a a Cp-Cq alkyl group substituted by a Cm-Cn alkoxycarbonyl group.

The term "carbocyclyl" or "carbocyclic ring" refers to a saturated or unsaturated (e.g. monounsaturated or diunsaturated), non-aromatic or aromatic cyclic moiety containing only carbon atoms in the ring. A saturated carbocyclyl is referred to as a cycloalkyl, while phenyl is an aromatic carbocyclyl.

The term "Cm-Cn carbocyclyl" refers to a carbocyclyl containing from m to n carbon atoms in the ring, wherein m is an integer higher than or equal to 3.

The term "Cm-Cn carbocyclyl-Cp-Cq alkyl" refers to a Cp-Cq alkyl substituted with Cm-Cn carbocyclyl. For example, cyclopropylmethyl is a C3 carbocyclyl-C1 alkyl radical of formula

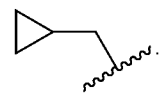

The term "Cm-Cn alkoxy" refers to a moiety of formula

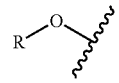

wherein R is Cm-Cn alkyl. For example, methoxy is C1 alkoxy.

The term "Cm-Cn alkoxy-Cp-Cq alkyl" refers to a Cp-Cq alkyl substituted with Cm-Cn alkoxy. For example methoxymethyl is C1 alkoxy-C1 alkyl.

The term "Cm-Cn carbocyclyloxy" refers to a moiety of formula

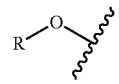

wherein R is Cm-Cn carbocyclyl; and m is an integer of at least 3.

The term "Cm-Cn carbocyclyloxy-Cp-Cq alkyl" refers to a Cp-Cq alkyl substituted with Cm-Cn carbocyclyloxy.

The term "carboxy" refers to a moiety of formula —COOH, which may also be represented as

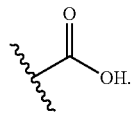

The term "carboxy-Cm-Cn alkyl" refers to a Cm-Cn alkyl group having one hydrogen atom replaced by a carboxy function (i.e. substituted by a carboxy group). One example is carboxymethyl.

The term "m- to n-membered heterocyclyl" refers to a cyclic moiety containing from m to n ring atoms, of which at least one is a heteroatom, e.g. a cyclic moiety containing from 1 to k-1 heteroatoms, wherein k is the total number of ring atoms (i.e. k is an integer of from m to n); e.g. 1-4 heteroatoms, or 1-3 heteroatoms, or 1 or 2 heteroatoms, e.g. 1 heteroatom. The heterocyclyl may be saturated or unsaturated and, when unsaturated, may be non-aromatic or aromatic (i.e. heteroaromatic). An aromatic heterocyclyl may also be referred to as a "heteroaryl".

The term "m- to n-membered heterocyclyl-Cp-Cq alkyl" refers to a Cp-Cq alkyl (wherein p represents an integer of at least 1) substituted with an m- to n-membered heterocyclyl.

The term "halogen" refers to F, Cl, Br or I; preferably F, Cl or Br.

The term "heteroatom" refers to an atom selected from nitrogen (N), oxygen (O), and sulphur (S).

The term "non-aromatic", as used herein, also includes "non-heteroaromatic" unless otherwise specified.

The term "hydroxy" refers to the moiety HO—.

The term "hydroxy-Cm-Cn alkyl" refers to an alkyl group containing from m to n carbon atoms and having one hydrogen atom replaced by a hydroxy function, i.e. a Cm-Cn alkyl substituted by a hydroxy function. One example is hydroxymethyl.

The expression "adjacent phenyl ring atoms" (as in the expression "two $R_1$ attached to adjacent phenyl ring atoms") refers to two adjacent carbon atoms of a phenyl ring.

In the context of the present disclosure, the expression "two $R_1$ attached to adjacent phenyl ring atoms" or "two $R_1$ attached to adjacent atoms of the phenyl ring" refers to two moieties $R_1$ that, in a compound of formula (I), are adjacently situated on the phenyl ring substituted by n moieties $R_1$, wherein n is at least 2.

In a compound of formula (I), n is an integer ranging from 1 to 5. In some embodiments, n is an integer ranging from 1 to 4. In some embodiments, n is an integer ranging from 1 to 3. In some embodiments, n is 1 or 2. In some embodiments, n is 1. In some further embodiments, n is an integer ranging from 2 to 5, e.g. from 3 to 5, or from 4 to 5. In still other embodiments, n is an integer ranging from 2 to 4. In still other embodiments, n is 2 or 3. In still other embodiments, n is 3 or 4. In some embodiments, n is 2. In some embodiments, n is 3. In some embodiments, n is 4. In some embodiments, n is 5.

In a compound of formula (I), each $R_1$ is independently selected from C1-C6 alkyl, C3-C6 carbocyclyl, C3-C6 carbocyclyl-C1-C3 alkyl, C1-C6 alkoxy, C1-C6 alkoxy-C1-C3 alkyl, C3-C6 carbocyclyloxy, C3-C6 carbocyclyloxy-C1-C3 alkyl, 4- to 6-membered heterocyclyl, 4- to 6-membered heterocyclyl-C1-C3 alkyl, hydroxy, hydroxy-C1-C3 alkyl, carboxy, carboxy-C1-C3 alkyl, C1-C6 alkoxycarbonyl, C1-C6 alkoxycarbonyl-C1-C3 alkyl, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties independently selected from C1-C3 alkyl and halogen.

In some embodiments, each $R_1$ is independently selected from C1-C6 alkyl, C3-C6 carbocyclyl, C3-C6 carbocyclyl-C1-C3 alkyl, C1-C6 alkoxy, C1-C6 alkoxy-C1-C3 alkyl, C3-C6 carbocyclyloxy, C3-C6 carbocyclyloxy-C1-C3 alkyl, 4- to 6-membered heterocyclyl, 4- to 6-membered heterocyclyl-C1-C3 alkyl, hydroxy, hydroxy-C1-C3 alkyl, carboxy, carboxy-C1-C3 alkyl, C1-C6 alkoxycarbonyl, C1-C6 alkoxycarbonyl-C1-C3 alkyl, and halogen.

In some embodiments, each $R_1$ is independently selected from C1-C6 alkyl, C3-C6 carbocyclyl, C3-C6 carbocyclyl-C1-C3 alkyl, C1-C6 alkoxy, C1-C6 alkoxy-C1-C3 alkyl, C3-C6 carbocyclyloxy, C3-C6 carbocyclyloxy-C1-C3 alkyl, 4- to 6-membered heterocyclyl, 4- to 6-membered heterocyclyl-C1-C3 alkyl, hydroxy, hydroxy-C1-C3 alkyl, carboxy, carboxy-C1-C3 alkyl, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties independently selected from C1-C3 alkyl and halogen.

In some embodiments, each $R_1$ is independently selected from C1-C6 alkyl, C3-C6 carbocyclyl, C1-C6 alkoxy, 4- to 6-membered heterocyclyl, hydroxy, carboxy, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties independently selected from C1-C3 alkyl and halogen.

In some embodiments, each $R_1$ is independently selected from C1-C6 alkyl, C3-C6 carbocyclyl, C3-C6 carbocyclyl-C1-C3 alkyl, C1-C6 alkoxy, C1-C6 alkoxy-C1-C3 alkyl, C3-C6 carbocyclyloxy, C3-C6 carbocyclyloxy-C1-C3 alkyl, 4- to 6-membered heterocyclyl, 4- to 6-membered heterocyclyl-C1-C3 alkyl, hydroxy, hydroxy-C1-C3 alkyl, and halogen; and when n is at least 2, two $R_1$ attached to adjacent phenyl ring atoms, together with the atoms to which they are attached, may form a 4- to 6-membered non-aromatic ring optionally containing one or more heteroatoms and optionally substituted with one or more moieties selected from C1-C3 alkyl and halogen.

In some embodiments, each $R_1$ is independently selected from C1-C6 alkyl, C3-C6 carbocyclyl, C3-C6 carbocyclyl-C1-C3 alkyl, C1-C6 alkoxy, C1-C6 alkoxy-C1-C3 alkyl, C3-C6 carbocyclyloxy, C3-C6 carbocyclyloxy-C1-C3 alkyl, 4- to 6-membered heterocyclyl, 4- to 6-membered heterocyclyl-C1-C3 alkyl, and halogen.

In some embodiments, each $R_1$ is independently selected from C1-C6 alkyl, C3-C6 carbocyclyl, C3-C6 carbocyclyl-C1-C3 alkyl, 4- to 6-membered heterocyclyl, 4- to 6-membered heterocyclyl-C1-C3 alkyl, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties selected from C1-C3 alkyl and halogen.

In some other embodiments, each $R_1$ is independently selected from C1-C6 alkyl, C3-C6 carbocyclyl, C1-C6 alkoxy, C3-C6 carbocyclyloxy, 4- to 6-membered heterocyclyl, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties selected from C1-C3 alkyl and halogen.

In some embodiments, each $R_1$ is independently selected from C1-C6 alkyl, C1-C6 alkoxy, C1-C6 alkoxy-C1-C3 alkyl, 4- to 6-membered heterocyclyl, 4- to 6-membered heterocyclyl-C1-C3 alkyl, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties selected from C1-C3 alkyl and halogen.

In some embodiments, each $R_1$ is independently selected from C1-C6 alkyl, C3-C6 carbocyclyl, C3-C6 carbocyclyl-C1-C3 alkyl, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties selected from C1-C3 alkyl and halogen.

In some other embodiments, each $R_1$ is independently selected from C1-C6 alkyl, C3-C6 carbocyclyl, 4- to 6-membered heterocyclyl, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties selected from C1-C3 alkyl and halogen.

In some embodiments, each $R_1$ is independently selected from C1-C6 alkyl, C3-C6 carbocyclyl, C3-C6 carbocyclyl-C1-C3 alkyl, C1-C6 alkoxy, C1-C6 alkoxy-C1-C3 alkyl, C3-C6 carbocyclyloxy, C3-C6 carbocyclyloxy-C1-C3 alkyl, and halogen.

In some embodiments, each $R_1$ is independently selected from C1-C6 alkyl, 4- to 6-membered heterocyclyl, 4- to 6-membered heterocyclyl-C1-C3 alkyl, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties selected from C1-C3 alkyl and halogen.

In some embodiments, each $R_1$ is independently selected from C1-C6 alkyl, C3-C6 carbocyclyl, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties selected from C1-C3 alkyl and halogen.

In some other embodiments, each $R_1$ is independently selected from C1-C6 alkyl, C3-C6 carbocyclyl, 4- to 6-membered heterocyclyl, and halogen.

In some embodiments, each $R_1$ is independently selected from C1-C6 alkyl, C3-C6 carbocyclyl, C3-C6 carbocyclyl-C1-C3 alkyl, and halogen.

In some embodiments, each $R_1$ is independently selected from C1-C6 alkyl, 4- to 6-membered heterocyclyl, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties selected from C1-C3 alkyl and halogen.

In some embodiments, each $R_1$ is independently selected from C1-C6 alkyl, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties selected from C1-C3 alkyl and halogen.

In some embodiments, each $R_1$ is independently selected from C1-C6 alkyl, 4- to 6-membered heterocyclyl, and halogen. In some embodiments, each $R_1$ is independently selected from C1-C6 alkyl, C3-C6 carbocyclyl, and halogen. In some embodiments, each $R_1$ is independently selected from C1-C6 alkyl, and halogen. In some embodiments, each $R_1$ is independently selected from C1-C6 alkyl and C3-C6 carbocyclyl. In some embodiments, each $R_1$ is independently selected from halogen.

In some further embodiments, each $R_1$ is independently selected from C1-C6 alkyl, C3-C6 carbocyclyl, C3-C6 carbocyclyl-C1-C3 alkyl, C1-C6 alkoxy, C1-C6 alkoxy-C1-C3 alkyl, hydroxy, hydroxy-C1-C3 alkyl, carboxy, carboxy-C1-C3 alkyl, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties independently selected from C1-C3 alkyl and halogen.

In some further embodiments, each $R_1$ is independently selected from C1-C6 alkyl, C3-C6 carbocyclyl, C3-C6 carbocyclyl-C1-C3 alkyl, C1-C6 alkoxy, C1-C6 alkoxy-C1-C3 alkyl, hydroxy, hydroxy-C1-C3 alkyl, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties independently selected from C1-C3 alkyl and halogen.

In some further embodiments, each $R_1$ is independently selected from C1-C6 alkyl, C3-C6 carbocyclyl, C1-C6 alkoxy, hydroxy, carboxy, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties independently selected from C1-C3 alkyl and halogen.

In some further embodiments, each $R_1$ is independently selected from C1-C6 alkyl, C3-C6 carbocyclyl, C1-C6 alkoxy, hydroxy, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties independently selected from C1-C3 alkyl and halogen.

In some further embodiments, each $R_1$ is independently selected from C1-C6 alkyl, C3-C6 carbocyclyl, C3-C6 carbocyclyl-C1-C3 alkyl, hydroxy, hydroxy-C1-C3 alkyl, carboxy, carboxy-C1-C3 alkyl, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties independently selected from C1-C3 alkyl and halogen.

In some further embodiments, each $R_1$ is independently selected from C1-C6 alkyl, C3-C6 carbocyclyl, hydroxy, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties independently selected from C1-C3 alkyl and halogen.

In some further embodiments, each $R_1$ is independently selected from C1-C6 alkyl, C3-C6 carbocyclyl, C3-C6 carbocyclyl-C1-C3 alkyl, C1-C6 alkoxy, C1-C6 alkoxy-C1-C3 alkyl, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties independently selected from C1-C3 alkyl and halogen.

In some further embodiments, each $R_1$ is independently selected from C1-C6 alkyl, C3-C6 carbocyclyl, C1-C6 alkoxy, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties independently selected from C1-C3 alkyl and halogen.

In some further embodiments, each $R_1$ is independently selected from C1-C6 alkyl, C3-C6 carbocyclyl, C3-C6 carbocyclyl-C1-C3 alkyl, C1-C6 alkoxy, C1-C6 alkoxy-C1-C3 alkyl, hydroxy, hydroxy-C1-C3 alkyl, carboxy, carboxy-C1-C3 alkyl, and halogen; e.g. from C1-C6 alkyl, C3-C6 carbocyclyl, C3-C6 carbocyclyl-C1-C3 alkyl, C1-C6 alkoxy, C1-C6 alkoxy-C1-C3 alkyl, hydroxy, hydroxy-C1-C3 alkyl, and halogen.

In some further embodiments, each $R_1$ is independently selected from C1-C6 alkyl, C3-C6 carbocyclyl, C1-C6 alkoxy, hydroxy, carboxy, and halogen; e.g. from C1-C6 alkyl, C3-C6 carbocyclyl, C1-C6 alkoxy, hydroxy, and halogen.

In some further embodiments, each $R_1$ is independently selected from C1-C6 alkyl, C3-C6 carbocyclyl, C3-C6 carbocyclyl-C1-C3 alkyl, hydroxy, hydroxy-C1-C3 alkyl, carboxy, carboxy-C1-C3 alkyl, and halogen.

In some further embodiments, each $R_1$ is independently selected from C1-C6 alkyl, C3-C6 carbocyclyl, hydroxy, and halogen.

In some further embodiments, each $R_1$ is independently selected from C1-C6 alkyl, C3-C6 carbocyclyl, C3-C6 carbocyclyl-C1-C3 alkyl, C1-C6 alkoxy, C1-C6 alkoxy-C1-C3 alkyl, and halogen.

In some further embodiments, each $R_1$ is independently selected from C1-C6 alkyl, C3-C6 carbocyclyl, C1-C6 alkoxy, and halogen.

In some embodiments, each $R_1$ is independently selected from halogen and hydroxy.

In some further embodiments, at least one $R_1$ is selected from halogen.

When $R_1$ is C1-C6 alkyl, $R_1$ more particularly may be C1-C4 alkyl, or C1-C3 alkyl. In some embodiments, when $R_1$ is C1-C6 alkyl, $R_1$ more particularly is methyl or isopropyl. In some embodiments, when $R_1$ is C1-C6 alkyl, $R_1$ more particularly is methyl.

When $R_1$ is C3-C6 carbocyclyl, $R_1$ more particularly may be C3-C5 carbocyclyl. In some embodiments, when $R_1$ is C3-C6 carbocyclyl, $R_1$ more particularly is cyclopropyl.

When $R_1$ is C3-C6 carbocyclyl-C1-C3 alkyl, $R_1$ more particularly may be C3-C5 carbocyclyl-C1-C3 alkyl, e.g. cyclopropyl-C1-C3 alkyl, or cyclopropyl-C1-C2 alkyl, such as cyclopropylmethyl. In some embodiments, when $R_1$ is C3-C6 carbocyclyl-C1-C3 alkyl, $R_1$ more particularly is C3-C6 carbocyclyl-C1-C2 alkyl, e.g. $R_1$ is C3-C6 carbocyclylmethyl, or C3-C5 carbocyclylmethyl.

In some embodiments, when any $R_1$ is a carbocyclyl or comprises a carbocyclyl (as in C3-C6 carbocyclyl-C1-C3 alkyl), the carbocyclyl is non-aromatic. In some embodiments, when any $R_1$ is a carbocyclyl or comprises a carbocyclyl, the carbocyclyl is non-aromatic and saturated.

When $R_1$ is C1-C6 alkoxy, $R_1$ more particularly may be C1-C4 alkoxy, or C1-C3 alkoxy. In some embodiments, when $R_1$ is C1-C6 alkoxy, $R_1$ more particularly is methoxy.

When $R_1$ is C1-C6 alkoxy-C1-C3 alkyl, $R_1$ more particularly may be C1-C3 alkoxy-C1-C3 alkyl, e.g. methoxy-C1-C3 alkyl, or methoxy-C1-C2 alkyl, such as methoxymethyl. In some embodiments, when $R_1$ is C1-C6 alkoxy-C1-C3 alkyl, $R_1$ more particularly is C1-C3 alkoxymethyl.

When $R_1$ is C3-C6 carbocyclyloxy, $R_1$ more particularly may be C3-C5 carbocyclyloxy, e.g. cyclopropyloxy.

When $R_1$ is C3-C6 carbocyclyloxy-C1-C3 alkyl, $R_1$ more particularly may be C3-C5 carbocyclyloxy-C1-C3 alkyl, e.g. cyclopropyloxy-C1-C3 alkyl, or cyclopropyloxy-C1-C2 alkyl, such as cyclopropyloxymethyl. In some embodiments, when $R_1$ is C3-C6 carbocyclyloxy-C1-C3 alkyl, $R_1$ more particularly is C3-C6 carbocyclyloxy-C1-C2 alkyl, e.g. $R_1$ is C3-C6 carbocyclyloxymethyl, or C3-C5 carbocyclyloxymethyl.

In some embodiments, when $R_1$ is a carbocyclyl or comprises a carbocyclyl moiety, such carbocyclyl is not phenyl.

When $R_1$ is 4- to 6-membered heterocyclyl or 4- to 6-membered heterocyclyl-C1-C3 alkyl, the 4-6 membered heterocylyl e.g. may be a 5- or 6-membered heterocyclyl. Any such heterocyclyl may contain one or more heteroatoms, e.g. 1, 2, 3 or 4 heteroatoms, or 1-3 heteroatoms, e.g. 1 or 2 heteroatoms, or 1 heteroatom, selected from N, O and S.

In some embodiments, when $R_1$ is 4- to 6-membered heterocyclyl or 4- to 6-membered heterocyclyl-C1-C3 alkyl, such heterocyclyl is non-aromatic. In some embodiments, when $R_1$ is 5- or 6-membered heterocyclyl or 5- or 6-membered heterocyclyl-C1-C3 alkyl, such heterocyclyl is (hetero)aromatic, i.e. 5- or 6-membered heteroaryl. In some embodiments, when $R_1$ is 4- to 6-membered heterocyclyl or 4- to 6-membered heterocyclyl-C1-C3 alkyl, the heterocyclyl is 5- or 6-membered, in particular 5- or 6-membered heteroaryl, and contains one or more heteroatoms, e.g. 1, 2 or 3 heteroatoms, or 1 or 2 heteroatoms, e.g. 1 heteroaom. In some of these embodiments, any such heteroatom is nitrogen (N). In some embodiments, when $R_1$ is 4- to 6-membered heterocyclyl or 4- to 6-membered heterocyclyl-C1-C3 alkyl, the heterocyclyl is pyridinyl, e.g. 3-pyridinyl.

In some other embodiments, any 4-6-membered heterocyclyl may be selected from azetidinyl, pyrrolidinyl, tetrahydrofuryl, tetrahydrothienyl, pyrrolyl, furyl, thienyl, imidazolidinyl, pyrazolidinyl, oxazolidinyl, isoxazolidinyl, thiazolidinyl, isothiazolidinyl, dioxolyl, dithiolyl, imidazolyl, pyrazolyl, oxazolyl, isoxazolyl, thiazolyl, isothiazolyl, triazolyl, furazolyl, oxadiazolyl, thiadiazolyl, dithiazolyl, tetrazolyl, piperidinyl, tetrahydropyranyl, thianyl, pyridinyl, piperazinyl, morpholinyl, thiomorpholinyl, dioxanyl, diazinyl, oxazinyl, thiazinyl, and triazinyl.

When $R_1$ is halogen, such halogen e.g. may be selected from F, Cl and Br. In some embodiments, any such halogen is selected from Cl and Br.

When $R_1$ is hydroxy-C1-C3 alkyl, $R_1$ more particularly may be hydroxy-C1-C2 alkyl, such as hydroxymethyl.

When $R_1$ is carboxy-C1-C3 alkyl, $R_1$ more particularly may be carboxy-C1-C2 alkyl, such as carboxyymethyl.

When $R_1$ is C1-C6 alkoxycarbonyl, $R_1$ more particularly may be C1-C3 alkoxycarbonyl, e.g.

C1-C2 alkoxycarbonyl, such as methoxycarbonyl.

When $R_1$ is C1-C6 alkoxycarbonyl-C1-C3 alkyl, $R_1$ more particularly may be C1-C3 alkoxycarbonyl-C1-C3 alkyl, e.g. C1-C2 alkoxycarbonyl-C1-C3 alkyl, such as methoxycarbonyl-C1-C3 alkyl. Even more particularly, $R_1$ more particularly may be C1-C3 alkoxycarbonyl-C1-C2 alkyl, e.g. C1-C2 alkoxycarbonyl-C1-C2 alkyl, such as methoxycarbonyl-C1-C2 alkyl; in particular $R_1$ more may be C1-C3 alkoxycarbonylmethyl, e.g. C1-C2 alkoxycarbonylmethyl, such as methoxycarbonylmethyl.

When the compound of formula (I) comprises two $R_1$ attached to adjacent atoms of the phenyl ring, such $R_1$, together with the phenyl ring atoms to which they are attached, may form a 4- to 6-membered non-aromatic ring optionally containing one or more heteroatoms and optionally substituted with one or more moieties independently selected from C1-C3 alkyl and halogen. In some embodiments, the ring is 5- or 6-membered. In some embodiments, the ring is 5-membered. In some embodiments, the ring is 5- or 6-membered and optionally contains one or more heteroatoms selected from N, O and S. When such ring contains one or more heteroatoms, it e.g. may contain 1-3 heteroatoms, e.g. 1 or 2 heteroatoms, or 1 heteroatom.

When two $R_1$ attached to adjacent atoms of the phenyl ring, together with the atoms to which they are attached, form a 4- to 6-membered non-aromatic ring optionally containing one or more heteroatoms, such ring is optionally substituted with one or more moieties independently selected from C1-C3 alkyl and halogen, e.g. 1-4 moieties, or 1-3 moieties, e.g. 1 or 2 moieties, independently selected from C1-C3 alkyl and halogen. In some embodiments, any such moiety is independently selected from methyl, ethyl, isopropyl, F, Cl, and Br, e.g. from methyl, F, Cl, and Br, or from methyl, F and Cl. In some embodiments, any such moiety is selected from C1-C3 alkyl, e.g. methyl.

In some other particular embodiments, each $R_1$ is independently selected from methyl, isopropyl, trifluoromethyl, cyclopropyl, Cl, Br, pyridinyl, hydroxy and carboxy. In some further particular embodiments, each $R_1$ is independently selected from methyl, isopropyl, trifluoromethyl, cyclopropyl, Cl, Br, hydroxy and carboxy; e.g. from methyl, isopropyl, trifluoromethyl, cyclopropyl, Br, hydroxy and carboxy; in particular from methyl, isopropyl, cyclopropyl, Br, hydroxy and carboxy, e.g. from isopropyl, cyclopropyl, Br, hydroxy and carboxy.

In some other particular embodiments, each $R_1$ is independently selected from methyl, isopropyl, trifluoromethyl, cyclopropyl, Cl, Br, pyridinyl, and hydroxy. In some further particular embodiments, each $R_1$ is independently selected from methyl, isopropyl, trifluoromethyl, cyclopropyl, Cl, Br, hydroxy and carboxy; e.g. from methyl, isopropyl, trifluoromethyl, cyclopropyl, Br, and hydroxy; in particular from methyl, isopropyl, cyclopropyl, Br, and hydroxy, e.g. from isopropyl, cyclopropyl, Br, and hydroxy.

In some other particular embodiments, each $R_1$ is independently selected from methyl, isopropyl, trifluoromethyl, cyclopropyl, Cl, Br, and pyridinyl. In some further particular embodiments, each $R_1$ is independently selected from methyl, isopropyl, trifluoromethyl, cyclopropyl, Cl and Br; e.g. from methyl, isopropyl, trifluoromethyl, cyclopropyl, and Br; in particular from methyl, isopropyl, cyclopropyl, and Br, e.g. from isopropyl, cyclopropyl, and Br.

In a compound of formula (I), $R_2$ is selected from C1-C6 alkyl, C3-C6 carbocyclyl, C3-C6 carbocyclyl-C1-C3 alkyl, C1-C6 alkoxy, C1-C6 alkoxy-C1-C3 alkyl, C3-C6 carbocyclyloxy, C3-C6 carbocyclyloxy-C1-C3 alkyl, halogen, hydroxy, and hydroxy-C1-C3 alkyl. In some embodiments, $R_2$ is selected from C1-C6 alkyl, C3-C6 carbocyclyl, C1-C6 alkoxy, C3-C6 carbocyclyloxy, halogen, and hydroxy.

In some embodiments, $R_2$ is selected from C1-C6 alkyl, C1-C6 alkoxy, C1-C6 alkoxy-C1-C3 alkyl, halogen, hydroxy, and hydroxy-C1-C3 alkyl.

In some embodiments, $R_2$ is selected from C1-C6 alkyl, C3-C6 carbocyclyl, C3-C6 carbocyclyl-C1-C3 alkyl, halogen, hydroxy, and hydroxy-C1-C3 alkyl.

In some embodiments, $R_2$ is selected from C1-C6 alkyl, C1-C6 alkoxy, halogen, and hydroxy.

In some embodiments, $R_2$ is selected from C1-C6 alkyl, halogen, and hydroxy. In some embodiments, $R_2$ is selected from C1-C6 alkyl, and hydroxy. In still further embodiments, $R_2$ is selected from C1-C6 alkyl, and halogen. In some embodiments, $R_2$ is selected from C1-C6 alkyl.

In some embodiments, $R_2$ is selected from C1-C6 alkyl, halogen, hydroxy, and hydroxy-C1-C3 alkyl. In some embodiments, $R_2$ is selected from halogen, hydroxy, and hydroxy-C1-C3 alkyl. In some embodiments, $R_2$ is selected from halogen and hydroxy. In some embodiments, $R_2$ is selected from halogen. In some embodiments, $R_2$ is selected from hydroxy and hydroxy-C1-C3 alkyl, e.g. $R_2$ is hydroxy.

When $R_2$ is C1-C6 alkyl, $R_2$ more particularly may be C1-C4 alkyl, in particular C1-C3 alkyl. In some embodiments, when $R_2$ is C1-C6 alkyl, $R_2$ more particularly is methyl.

When $R_2$ is C3-C6 carbocyclyl, $R_2$ more particularly may be C3-C5 carbocyclyl. In some embodiments, when $R_2$ is C3-C6 carbocyclyl, $R_2$ more particularly is cyclopropyl.

When $R_2$ is C3-C6 carbocyclyl-C1-C3 alkyl, $R_2$ more particularly may be C3-C5 carbocyclyl-C1-C3 alkyl, e.g. cyclopropyl-C1-C3 alkyl, or cyclopropyl-C1-C2 alkyl, such as cyclopropylmethyl. In some embodiments, when $R_2$ is C3-C6 carbocyclyl-C1-C3 alkyl, $R_2$ more particularly is C3-C6 carbocyclyl-C1-C2 alkyl, e.g. $R_2$ is C3-C6 carbocyclylmethyl, or C3-C5 carbocyclylmethyl.

In some embodiments, when any $R_2$ is a carbocyclyl or comprises a carbocyclyl (as in C3-C6 carbocyclyl-C1-C3 alkyl), the carbocyclyl is non-aromatic. In some embodiments, when any $R_2$ is a carbocyclyl or comprises a carbocyclyl, the carbocyclyl is non-aromatic and saturated, i.e. cycloalkyl. In some embodiments, when $R_2$ is a carbocyclyl or comprises a carbocyclyl moiety, such carbocyclyl is not phenyl.

When $R_2$ is C1-C6 alkoxy, $R_2$ more particularly may be C1-C4 alkoxy, or C1-C3 alkoxy. In some embodiments, when $R_2$ is C1-C6 alkoxy, $R_2$ more particularly is methoxy.

When $R_2$ is C1-C6 alkoxy-C1-C3 alkyl, $R_2$ more particularly may be C1-C3 alkoxy-C1-C3 alkyl, e.g. methoxy-C1-C3 alkyl, or methoxy-C1-C2 alkyl, such as methoxymethyl. In some embodiments, when $R_2$ is C1-C6 alkoxy-C1-C3 alkyl, $R_2$ more particularly is C1-C3 alkoxymethyl.

When $R_2$ is C3-C6 carbocyclyloxy, $R_2$ more particularly may be C3-C5 carbocyclyloxy, e.g. cyclopropyloxy.

When $R_2$ is C3-C6 carbocyclyloxy-C1-C3 alkyl, $R_2$ more particularly may be C3-C5 carbocyclyloxy-C1-C3 alkyl, e.g. cyclopropyloxy-C1-C3 alkyl, or cyclopropyloxy-C1-C2 alkyl, such as cyclopropyloxymethyl. In some embodiments, when $R_2$ is C3-C6 carbocyclyloxy-C1-C3 alkyl, $R_2$ more particularly is C3-C6 carbocyclyloxy-C1-C2 alkyl, e.g. $R_2$ is C3-C6 carbocyclyloxymethyl, or C3-C5 carbocyclyloxymethyl.

When $R_2$ is halogen, such halogen e.g. may be selected from F, Cl and Br. In some embodiments, any such halogen is selected from Cl and Br. In some other embodiments, any such halogen is selected from F and Cl. In still other embodiments, when $R_2$ is halogen, it more particularly is F. In still other embodiments, when $R_2$ is halogen, it more particularly is Cl. In still other embodiments, when $R_2$ is halogen, it more particularly is Br.

When $R_2$ is hydroxy-C1-C3 alkyl, $R_2$ in particular may be hydroxy-C1-C2 alkyl, e.g. $R_2$ may be hydroxymethyl.

For the avoidance of doubt, it is pointed out that in any of the above mentioned embodiments, any alkyl (whether in $R_1$ or $R_2$) is optionally substituted with one or more, e.g. 1-3, halogens, e.g. selected one or more halogens independently selected from F, Cl and Br, or from F and Cl, in particular from F, unless otherwise specified. In some embodiments, no such halogen is present as optional substituent.

Furthermore, in any of the above mentioned embodiments, any carbocyclyl or heterocyclyl is optionally substituted with one or more, e.g. 1-3, moieties selected from halogen and C1-C3 alkyl. In some embodiments, any such moiety is selected from halogen and methyl, e.g. from F, Cl, Br and methyl, or from F, Cl and methyl, or from F and methyl. In some embodiments, any such moiety is selected from C1-C3 alkyl, e.g. methyl. In other embodiments, any such moiety is selected from halogen, e.g. from F, Cl and Br, or from F and Cl, in particular from F. In some embodiments, no such optional substituent is present on any carbocyclyl or heterocyclyl.

In a compound of formula (I) each one of $R_3$, $R_4$, $R_5$, and $R_6$ is independently selected from H and F. In some embodiments, at least two of $R_3$, $R_4$, $R_5$, and $R_6$ are H. In some embodiments, at least three of $R_3$, $R_4$, $R_5$, and $R_6$ are H. In some embodiments, $R_3$ and $R_4$ are H. In some embodiments, $R_3$, $R_4$, and $R_5$ are H. In some embodiments, $R_3$, $R_4$, $R_5$, and $R_6$ are all H. In some particular embodiments, $R_3$ and $R_4$ are H, and $R_5$ and $R_6$ are F. In some other particular embodiments, $R_3$, $R_4$, and $R_5$ are H, and $R_6$ is F. In still other embodiments, at least one of $R_3$, $R_4$, $R_5$, and $R_6$ is F; e.g. at least one of $R_5$ and $R_6$ is F. In still further embodiments, $R_3$ and $R_4$ are H; and $R_5$ and $R_6$ are selected from H and F.

In some embodiments, the compound of formula (I) more particularly is a compound of formula (Ia)

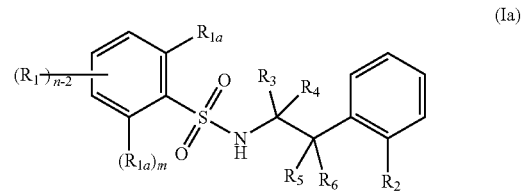

wherein m is 0 or 1;

n is an integer of from 2 to 5; e.g. n is 2, 3 or 4; or n is 2 or 3;

each $R_1$, $R_2$, $R_3$, $R_4$, $R_5$, and $R_6$ are as defined herein; and each $R_{1a}$ is independently selected from C1-C6 alkyl, C1-C6 alkoxy, C1-C6 alkoxy-C1-C3 alkyl, halogen, hydroxy, hydroxy-C1-C3 alkyl, carboxy, and carboxy-C1-C3 alkyl, wherein any alkyl is optionally substituted by one or more halogens, e.g. one or more F.

In some embodiments of a compound of formula (Ia), m is 0. In some other embodiments of a compound of formula (Ia), m is 1.

In some embodiments of a compound of formula (Ia), n is 2. In some other embodiments of a compound of formula (Ia), n is 3.

In some embodiments, the compound of formula (Ia) more particularly is a compound of formula (Ib)

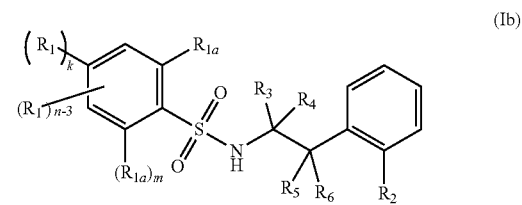

wherein k is 0 or 1; m is 0 or 1; n is an integer of from 3 to 5; and each $R_{1a}$, $R_1$, $R_2$, $R_3$, $R_4$, $R_5$, and $R_6$ are as defined herein.

In some embodiments of a compound of formula (Ib), n is 3 or 4.

In some embodiments of a compound of formula (Ib), n is 4. In some of the embodiments where n is 4, k is 1 and m is 1. In some other embodiments of a compound of formula (Ib), n is 3, i.e. the compound may be represented by formula (Ic)

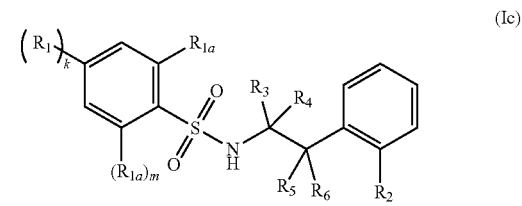

wherein k, m, each $R_{1a}$, $R_1$, $R_2$, $R_3$, $R_4$, $R_5$, and $R_6$ are as defined herein.

In some other particular embodiments, k is 0 and m is 1, i.e. the compound of formula (Ic) is as represented by formula (Id)

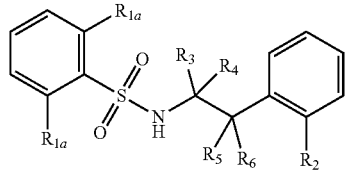

(Id)

wherein each $R_{1a}$, $R_2$, $R_3$, $R_4$, $R_5$, and $R_6$ are as defined herein.

In some further particular embodiments of a compound of formula (Ic), k and m are both 0, i.e. the compound of formula (Ic) is as represented by formula (Ie)

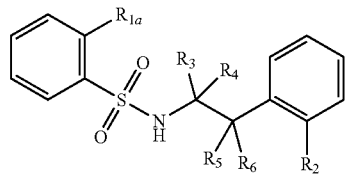

(Ie)

wherein $R_{1a}$, $R_2$, $R_3$, $R_4$, $R_5$, and $R_6$ are as defined herein.

In some further particular embodiments of a compound of formula (Ic), k and m are both 1, i.e. the compound of formula (Ic) is as represented by formula (If),

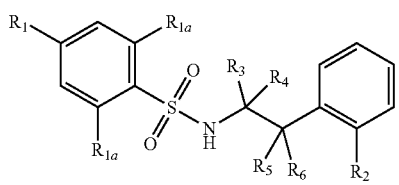

(If)

wherein each $R_{1a}$, $R_1$, $R_2$, $R_3$, $R_4$, $R_5$, and $R_6$ are as defined herein.

In some further particular embodiments of a compound of formula (Ic), k is 1 and m is 0, i.e. the compound of formula (Ic) is as represented by formula (Ig),

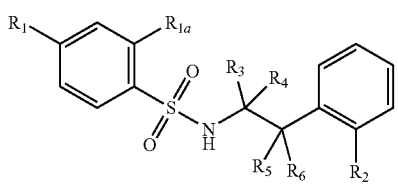

(Ig)

wherein each $R_1$, $R_{1a}$, $R_2$, $R_3$, $R_4$, $R_5$, and $R_6$ are as defined herein.

In some embodiments of a compound of formula (Ig), $R_{1a}$ and $R_1$ are both halogen. In some of these embodiments, $R_{1a}$ is Cl; e.g. $R_{1a}$ is Cl, and $R_1$ is Br or Cl.

Some further embodiments of a compound of formula (I), more particularly may be represented by formula (Ih)

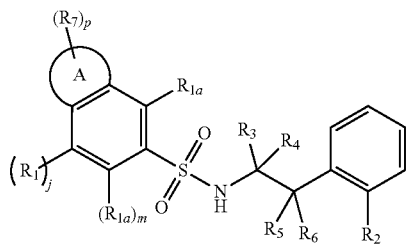

(Ih)

wherein
j is 0 or 1;
m is 0 and 1;
p is an integer of from 0 to 4, e.g. from 0 to 3, or from 0 to 2;
each $R_{1a}$, $R_1$, $R_2$, $R_3$, $R_4$, $R_5$, and $R_6$ are as defined herein;
each $R_7$ is independently selected from C1-C3 alkyl and halogen; and
ring A is a 4- to 6-membered non-aromatic ring optionally containing one or more heteroatoms, e.g. 1 or 2 heteroatoms; e.g. a 5- or 6-membered non-aromatic ring optionally containing one or more heteroatoms, e.g. 1 or 2 heteroatoms.

In some embodiments of a compound of formula (Ih), p is an integer of from 1 to 4, or from 1 to 3, e.g. p is 2.

In some embodiments of a compound of formula (Ih), each $R_7$ is independently selected from C1-C3 alkyl, e.g. each $R_7$ is methyl.

In some embodiments, of a compound of formula (Ih) ring A is non-aromatic, e.g. non-aromatic and 5-membered. For example, in some embodiments, a compound of formula (Ih) more particularly may be represented by formula (Ii)

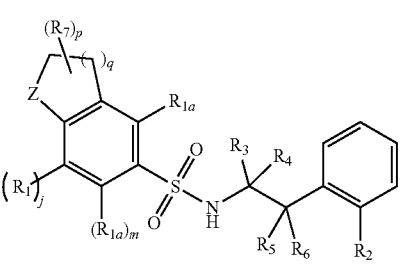

(Ii)

wherein
j is 0 or 1; e.g. j is 1;
M is 0 or 1; e.g. m is 1;
p is an integer of from 0 to 4, e.g. from 0 to 3, or from 0 to 2; e.g. p is an integer of from 1 to 4 or from 1 to 3;
q is 0, 1 or 2; e.g. q is 1 or 2;
Z is $C(R_8)_2$, $NR_8$, O or S; e.g. Z is $C(R_8)_2$ or O; or Z is O;
each $R_{1a}$, $R_1$, $R_2$, $R_3$, $R_4$, $R_5$, and $R_6$ are as defined herein;
each $R_7$ is independently selected from C1-C3 alkyl and halogen;
each $R_8$ is independently selected from H and C1-C3 alkyl; e.g. H and methyl; and
and any alkyl is optionally substituted by one or more halogens, e.g. one or more F.

In some embodiments of a compound of formula (Ii), q is 1; e.g. q is 1 and Z is O.

In some embodiments, the compound of formula (Ii) more particularly may be represented by formula (Ij)

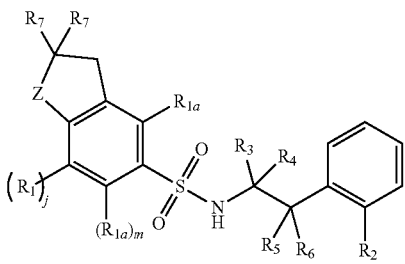

(Ij)

wherein j, m, Z, each $R_{1a}$, $R_1$, $R_2$, $R_3$, $R_4$, $R_5$, $R_6$ and each $R_7$ are as defined herein. In some embodiments of a compound of formula (Ij), each $R_{1a}$, $R_1$ and $R_7$ is C1-C3 alkyl, e.g. each is methyl.

In some embodiments of a compound of formula (Ii) or (Ij), m is 1. In some embodiments of a compound of formula (Ii) or (Ij), j is 1. In some embodiments of a compound of formula (Ii) or (Ij), Z is O. In some particular embodiments, m is 1 and j is 1. In some embodiments of a compound of formula (Ii) or (Ij), m is 1, j is 1, and Z is O.

In a compound of any one of the formulas (Ia), (Ib), (Ic), (Id), (Ie), (If), (Ig), (Ih), (Ii) or (Ij), each $R_{1a}$ is independently selected from C1-C6 alkyl, C1-C6 alkoxy, C1-C6 alkoxy-C1-C3 alkyl, halogen, hydroxy, hydroxy-C1-C3 alkyl, carboxy, and carboxy-C1-C3 alkyl, wherein any alkyl is optionally substituted by one or more halogens, e.g. one or more F.

In some embodiments, each $R_{1a}$ is independently selected from C1-C6 alkyl, C1-C6 alkoxy, halogen, hydroxy, and carboxy, wherein any alkyl is optionally substituted by one or more halogens, e.g. one or more F.

In some embodiments, each $R_{1a}$ is independently selected from C1-C6 alkyl, C1-C6 alkoxy, C1-C6 alkoxy-C1-C3 alkyl, and halogen, wherein any alkyl is optionally substituted by one or more halogens, e.g. one or more F.

In some embodiments, each $R_{1a}$ is independently selected from C1-C6 alkyl, C1-C6 alkoxy, and halogen, wherein any alkyl is optionally substituted by one or more halogens, e.g. one or more F.

In some embodiments, each $R_{1a}$ is independently selected from C1-C6 alkyl, C1-C6 alkoxy, hydroxy, carboxy, and halogen, wherein any alkyl is optionally substituted by one or more halogens, e.g. one or more F.

In some embodiments, each $R_{1a}$ is independently selected from C1-C6 alkyl, C1-C6 alkoxy, hydroxy, and halogen, wherein any alkyl is optionally substituted by one or more halogens, e.g. one or more F.

In some further embodiments, each $R_{1a}$ is selected from C1-C6 alkyl, hydroxy, carboxy and halogen e.g. from C1-C3 alkyl, hydroxy, carboxy and halogen, in particular from methyl, hydroxy, carboxy and Cl. In some embodiments each $R_{1a}$ is independently selected from C1-C3 alkyl, hydroxy and halogen; e.g. from methyl, hydroxy and halogen; in particular from methyl, hydroxy and Cl.

In some embodiments each $R_{1a}$ is independently selected from C1-C3 alkyl and halogen; e.g. from methyl and halogen; in particular from methyl and Cl.

In some of embodiments, one $R_{1a}$ is hydroxy, e.g. one $R_{1a}$ is hydroxy and, if present, the other $R_{1a}$ is as indicated herein, e.g. selected from C1-C3 alkyl, optionally substituted by one or more halogen, and halogen, in particular methyl and Cl. In some embodiments, one $R_{1a}$ is hydroxy and, if present, the other $R_{1a}$ is halogen, e.g. Cl.

In some further embodiments, one $R_{1a}$ is halogen, in particular Cl. In some embodiments, when k in formula (Ic) is 1, i.e. in some embodiments of a compound of formula (Id) or (If), one $R_{1a}$ is Cl, and the other one is Cl, hydroxy, carboxy or methyl; e.g. Cl, hydroxy or methyl; or Cl or methyl; or Cl or hydroxy. In some embodiments, both $R_{1a}$ are Cl. In some other embodiments, one $R_{1a}$ is methyl, and the other one is Cl, hydroxy, carboxy or methyl, e.g. Cl, hydroxy, or methyl; or Cl or methyl. In some embodiments, one $R_{1a}$ is C1-C3 alkyl, e.g. methyl. In some embodiments, when k in formula (Ic) is 1, i.e. in some embodiments of a compound of formula (Id) or (If), both $R_{1a}$ are methyl.

In some embodiments, each $R_{1a}$ is independently selected from C1-C3 alkyl, C1-C3 alkoxy, C1-C3 alkoxy-C1-C3 alkyl, hydroxy, hydroxy-C1-C3 alkyl, carboxy, carboxy-C1-C3 alkyl, and halogen; or from C1-C3 alkyl, C1-C3 alkoxy, hydroxy, carboxy, and halogen; or from C1-C3 alkyl, C1-C3 alkoxy, hydroxy, and halogen; wherein any alkyl may optionally be substituted by one or more halogen, e.g. one or more F.

In some embodiments, each $R_{1a}$ is independently selected from C1-C3 alkyl, C1-C3 alkoxy, C1-C3 alkoxy-C1-C3 alkyl, and halogen; or from C1-C3 alkyl, C1-C3 alkoxy, and halogen; wherein any alkyl may optionally be substituted by one or more halogen, e.g. one or more F.

In some embodiments, each $R_{1a}$ is independently from C1-C6 alkyl, and halogen. In some embodiments, e.g. in some embodiments of a compound of formula (Id), each $R_{1a}$ is independently selected from C1-C3 alkyl and halogen, e.g. from methyl and halogen, such as from methyl, F, Cl, or Br; or from methyl, Cl or Br; in particular from methyl and Cl.

In some other embodiments, each $R_{1a}$ is independently selected from C1-C6 alkyl, e.g. from C1-C3 alkyl. In some embodiments each $R_{1a}$ is methyl. In still other embodiments, each $R_{1a}$ is independently selected from halogen, e.g. from F, Cl, and Br; or from Cl and Br. In some embodiments, each $R_{1a}$ is Cl.

In some further embodiments, at least one $R_{1a}$ is selected from hydroxy, hydroxy-C1-C3 alkyl, carboxy, carboxy-C1-C3 alkyl, and halogen; e.g. from hydroxy, carboxy and halogen; or from hydroxy and carboxy, in particular hydroxy.

In some other particular embodiments, e.g. of a compound of formula (Ia), (Ib) or (Ic), each $R_1$ and each $R_{1a}$ are independently selected from C1-C3 alkyl, e.g. each $R_1$ is methyl or isopropyl, and each $R_{1a}$ methyl.

In some other embodiments, e.g. of a compound of formula (Ia), (Ib) or (Ic), each $R_1$ and each $R_{1a}$ are halogen, e.g. each is independently selected from Cl and Br.

In some embodiments, e.g. of a compound of formula (Ic), $R_1$ is Br or cyclopropyl; and each $R_{1a}$ is Cl. In some other particular embodiments, e.g. of a compound of formula (Ic), $R_1$ is Br and each $R_{1a}$ is Cl.

In some further particular embodiments of a compound of formula (I), each $R_1$ is independently selected from methyl, trifluoromethyl, isopropyl, cyclopropyl, pyridinyl, Cl, Br, hydroxy, and carboxy; and when n is at least 2, two $R_1$ attached to adjacent carbon atoms on the phenyl ring may form a dihydrobenzofuran ring, optionally substituted with one or more, e.g. 1 or 2, C1-C3 alkyl groups, e.g. methyl groups; and $R_2$ is selected from methyl, trifluoromethyl, methoxy, F, Cl, Br, and hydroxy.

In some further particular embodiments of a compound of formula (I), each $R_1$ is independently selected from methyl, trifluoromethyl, isopropyl, cyclopropyl, Cl, Br, hydroxy, and carboxy; and when n is at least 2, two $R_1$ attached to adjacent carbon atoms on the phenyl ring may form a dihydrobenzofuran ring, optionally substituted with one or more, e.g. 1 or 2, C1-C3 alkyl groups, e.g. methyl groups; and $R_2$ is selected from methyl, trifluoromethyl, F, Cl, Br, and hydroxy.

In some further particular embodiments of a compound of formula (I), each $R_1$ is independently selected from methyl, isopropyl, cyclopropyl, Cl, Br, hydroxy and carboxy; and $R_2$ is selected from methyl, Cl, Br, and hydroxy.

In some further particular embodiments of a compound of formula (I), each $R_1$ is independently selected from methyl, isopropyl, cyclopropyl, Cl, Br, and hydroxy; and $R_2$ is selected from methyl, Cl, Br, and hydroxy.

In some further particular embodiments of a compound of formula (I), each $R_1$ is independently selected from methyl, trifluoromethyl, isopropyl, cyclopropyl, pyridinyl, Cl, and Br; and when n is at least 2, two $R_1$ attached to adjacent carbon atoms on the phenyl ring may form a dihydrobenzofuran ring, optionally substituted with one or more, e.g. 1 or 2, C1-C3 alkyl groups, e.g. methyl groups; and $R_2$ is selected from methyl, trifluoromethyl, methoxy, F, Cl, Br, and hydroxy.

In some further particular embodiments of a compound of formula (I), each $R_1$ is independently selected from methyl, trifluoromethyl, isopropyl, cyclopropyl, Cl, and Br; and when n is at least 2, two $R_1$ attached to adjacent carbon atoms on the phenyl ring may form a dihydrobenzofuran ring, optionally substituted with one or more, e.g. 1 or 2, C1-C3 alkyl groups, e.g. methyl groups; and $R_2$ is selected from methyl, trifluoromethyl, F, Cl, Br, and hydroxy.

In some further particular embodiments of a compound of formula (I), each $R_1$ is independently selected from methyl, isopropyl, cyclopropyl, Cl, and Br; and $R_2$ is selected from methyl, Cl, Br, and hydroxy.

Some preferred embodiments of the invention are illustrated in formulas (Ik) to (Io):

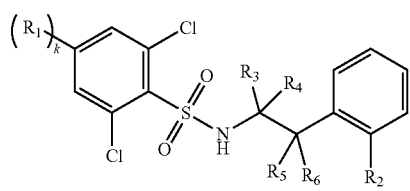

(Ik)

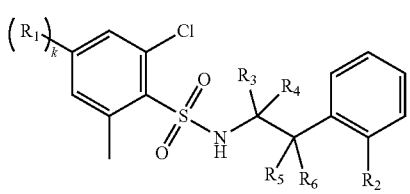

(Im)

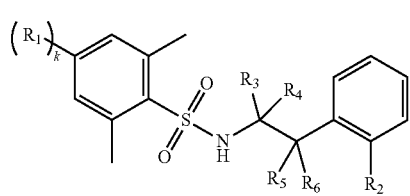

(In)

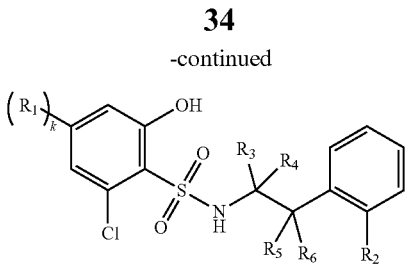

(Io)

wherein k is 0 or 1; preferably k is 1; and $R_1$, $R_2$, $R_3$, $R_4$, $R_5$, and $R_6$ are as defined herein.

In some further preferred embodiments of a compound of formula (I), said compound comprises at least one hydroxy or hydroxy-C1-C3 alkyl, e.g. at least one hydroxy. For example, a particularly preferred embodiment is as represented by formula (Ip)

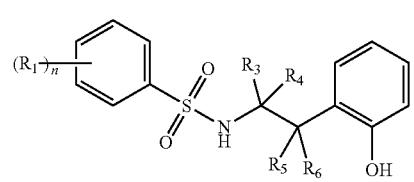

(Ip)

wherein n, $R_1$, $R_3$, $R_4$, $R_5$, and $R_6$ are as defined herein.

In some further embodiments, at least one $R_1$ is hydroxy, i.e. the compound may be represented by formula (Iq)

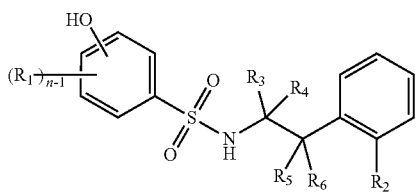

(Iq)

wherein $R_1$, $R_2$, $R_3$, $R_4$, $R_5$, and $R_6$ are as defined herein, and n is an integer of from 1 to 5, e.g. from 2 to 4. In some of embodiments of a compound of formula (Iq), only one $R_1$ is hydroxy, i.e. any further $R_1$ is as defined herein, but is different from hydroxy.

In some particular embodiments, $R_2$ and one $R_1$ only are hydroxy, i.e. the compound may be represented by formula (Ir)

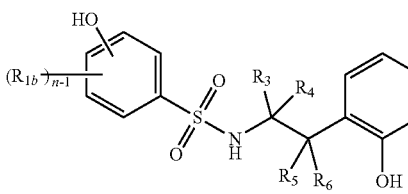

(Ir)

wherein $R_3$, $R_4$, $R_5$, and $R_6$ are as defined herein, n is an integer of from 1 to 5, e.g. from 2 to 4, and $R_{1b}$ is a moiety $R_1$ as defined herein, but different from hydroxy.

In some embodiments of a compound of formula (Iq), e.g. of formula (Ir), the $R_1$ group that is hydroxy is in ortho position on the phenyl ring to which it is attached.

In some embodiments of a compound of formula (Iq), the $R_1$ group that is hydroxy is in meta position on the phenyl ring to which it is attached. In some of these embodiments, the compound is a compound of formula (Ir).

In some embodiments of a compound of formula (Iq), the $R_1$ group that is hydroxy is in para position on the phenyl ring to which it is attached. For example, in some embodiments of a compound of formula (If), $R_1$ is hydroxy; e.g. $R_1$ is hydroxy and $R_{1a}$ is as defined herein, but different from hydroxy. In some of these embodiments, $R_2$ is hydroxy.

For the avoidance of doubt, it is pointed out that any reference to a compound of formula (I) also should be construed as a reference to a compound of any one of formulas (Ia), (Ib), (Ic), (Id), (Ie), (If), (Ig), (Ih), (Ii), or (Ij), (Ik), (Im), (In), (Io), (Ip), (Iq) and (Ir) unless otherwise indicated or apparent from the context.

In some further embodiments of a compound of formula (I), each $R_1$ is independently selected from C1-C6 alkyl, C3-C6 cycloalkyl, C1-C6 alkoxy, 5- or 6-membered heteroaryl, hydroxy, carboxy, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties independently selected from C1-C3 alkyl;

$R_2$ is selected from C1-C6 alkyl, C1-C6 alkoxy, halogen, and hydroxy;

$R_3$, $R_4$, $R_5$, and $R_6$ are independently selected from H and F; and any alkyl is optionally substituted with one or more halogens, e.g. one or more F.

In some embodiments of a compound of formula (I), each $R_1$ is independently selected from C1-C3 alkyl, cyclopropyl, C1-C3 alkoxy, 5- or 6-membered heteroaryl, hydroxy, carboxy, and halogen; and when n is at least 2, two $R_1$ attached to adjacent atoms of the phenyl ring, together with the atoms to which they are attached, may form a 5- or 6-membered non-aromatic ring optionally containing one or more heteroatoms and optionally substituted with one or more moieties independently selected from C1-C3 alkyl;

$R_2$ is selected from C1-C3 alkyl, C1-C3 alkoxy, halogen, and hydroxy;

$R_3$, $R_4$, $R_5$, and $R_6$ are independently selected from H and F; and any alkyl is optionally substituted with one or more halogens.

In some embodiments of a compound of formula (I), each $R_1$ is independently selected from methyl, trifluoromethyl, isopropyl, cyclopropyl, methoxy, pyridyl, hydroxy, carboxy, and halogen; and when n is at least 2, two $R_1$ attached to adjacent atoms of the phenyl ring, together with the atoms to which they are attached, may form a 5-membered non-aromatic ring optionally containing one or more heteroatoms and optionally substituted with one or more methyl;

$R_2$ is selected from methyl, trifluoromethyl, methoxy, halogen, and hydroxy; and $R_3$, $R_4$, $R_5$, and $R_6$ are independently selected from H and F.

In some embodiments of a compound of formula (I), each $R_1$ is independently selected from methyl, trifluoromethyl, isopropyl, cyclopropyl, methoxy, pyridyl, hydroxy, carboxy, and halogen (e.g. Cl and Br);

$R_2$ is selected from methyl, trifluoromethyl, methoxy, halogen (e.g. F, Cl and Br), and hydroxy; and $R_3$, $R_4$, $R_5$, and $R_6$ are independently selected from H and F.

In some embodiments of a compound of formula (I), each $R_1$ is independently selected from methyl, trifluoromethyl, isopropyl, cyclopropyl, methoxy, hydroxy, carboxy, and halogen;

$R_2$ is selected from methyl, trifluoromethyl, methoxy, halogen, and hydroxy; and $R_3$, $R_4$, $R_5$, and $R_6$ are independently selected from H and F.

In some embodiments of a compound of formula (I), each $R_1$ is independently selected from methyl, trifluoromethyl, isopropyl, cyclopropyl, methoxy, hydroxy, carboxy, Cl and Br;

$R_2$ is selected from methyl, trifluoromethyl, methoxy, F, Cl, Br, and hydroxy; and $R_3$, $R_4$, $R_5$, and $R_6$ are independently selected from H and F.

In some further embodiments of a compound of formula (I), each $R_1$ is independently selected from C1-C6 alkyl, C3-C6 cycloalkyl, 5- or 6-membered heteroaryl, hydroxy, carboxy, and halogen; and when n is at least 2, two $R_1$ attached to adjacent atoms of the phenyl ring, together with the atoms to which they are attached, may form a 4- to 6-membered non-aromatic ring optionally containing one or more heteroatoms and optionally substituted with one or more moieties independently selected from C1-C3 alkyl;

$R_2$ is selected from C1-C6 alkyl, C1-C6 alkoxy, halogen, and hydroxy;

$R_3$, $R_4$, $R_5$, and $R_6$ are independently selected from H and F; and any alkyl is optionally substituted with one or more halogens.

In some embodiments of a compound of formula (I), each $R_1$ is independently selected from C1-C3 alkyl, cyclopropyl, 5- or 6-membered heteroaryl, hydroxy, carboxy, and halogen; and when n is at least 2, two $R_1$ attached to adjacent atoms of the phenyl ring, together with the atoms to which they are attached, may form a 5- or 6-membered non-aromatic ring optionally containing one or more heteroatoms and optionally substituted with one or more moieties independently selected from C1-C3 alkyl;

$R_2$ is selected from C1-C3 alkyl, C1-C3 alkoxy, halogen, and hydroxy;

$R_3$, $R_4$, $R_5$, and $R_6$ are independently selected from H and F; and any alkyl is optionally substituted with one or more halogens.

In some embodiments of a compound of formula (I), each $R_1$ is independently selected from C1-C3 alkyl, cyclopropyl, 5- or 6-membered heteroaryl, hydroxy, carboxy, and halogen; and when n is at least 2, two $R_1$ attached to adjacent atoms of the phenyl ring, together with the atoms to which they are attached, may form a 5- or 6-membered non-aromatic ring optionally containing one or more heteroatoms and optionally substituted with one or more moieties independently selected from C1-C3 alkyl;

$R_2$ is selected from C1-C3 alkyl, C1-C3 alkoxy, halogen, and hydroxy;

$R_3$, $R_4$, $R_5$, and $R_6$ are independently selected from H and F; and any alkyl is optionally substituted with one or more halogens.

In some embodiments of a compound of formula (I), each $R_1$ is independently selected from methyl, trifluoromethyl, isopropyl, cyclopropyl, pyridyl, hydroxy, carboxy, and halogen; and when n is at least 2, two $R_1$ attached to adjacent atoms of the phenyl ring, together with the atoms to which they are attached, may form a 5-membered non-aromatic ring optionally containing one or more heteroatoms and optionally substituted with one or more methyl;

$R_2$ is selected from methyl, trifluoromethyl, methoxy, halogen, and hydroxy; and $R_3$, $R_4$, $R_5$, and $R_6$ are independently selected from H and F.

In some embodiments of a compound of formula (I), each $R_1$ is independently selected from methyl, trifluoromethyl, isopropyl, cyclopropyl, pyridyl, hydroxy, carboxy, and halogen (e.g. Cl and Br);

$R_2$ is selected from methyl, trifluoromethyl, methoxy, halogen (e.g. F, Cl and Br), and hydroxy; and $R_3$, $R_4$, $R_5$, and $R_6$ are independently selected from H and F.

In some embodiments of a compound of formula (I), each $R_1$ is independently selected from methyl, trifluoromethyl, isopropyl, cyclopropyl, hydroxy, carboxy, and halogen;

$R_2$ is selected from methyl, trifluoromethyl, methoxy, halogen, and hydroxy; and $R_3$, $R_4$, $R_5$, and $R_6$ are independently selected from H and F.

In some embodiments of a compound of formula (I), each $R_1$ is independently selected from methyl, trifluoromethyl, isopropyl, cyclopropyl, hydroxy, carboxy, Cl and Br;

$R_2$ is selected from methyl, trifluoromethyl, methoxy, F, Cl, Br, and hydroxy; and $R_3$, $R_4$, $R_5$, and $R_6$ are independently selected from H and F.

In some further embodiments of a compound of formula (I), each $R_1$ is independently selected from C1-C6 alkyl, C3-C6 cycloalkyl, 5- or 6-membered heteroaryl, hydroxy, and halogen; and when n is at least 2, two $R_1$ attached to adjacent atoms of the phenyl ring, together with the atoms to which they are attached, may form a 4- to 6-membered (preferably non-aromatic) ring optionally containing one or more heteroatoms and optionally substituted with one or more moieties independently selected from C1-C3 alkyl;

$R_2$ is selected from C1-C6 alkyl, C1-C6 alkoxy, halogen, and hydroxy;

$R_3$, $R_4$, $R_5$, and $R_6$ are independently selected from H and F; and any alkyl is optionally substituted with one or more halogens.

In some embodiments of a compound of formula (I), each $R_1$ is independently selected from C1-C3 alkyl, cyclopropyl, 5- or 6-membered heteroaryl, hydroxy, and halogen; and when n is at least 2, two $R_1$ attached to adjacent atoms of the phenyl ring, together with the atoms to which they are attached, may form a 5- or 6-membered non-aromatic ring optionally containing one or more heteroatoms and optionally substituted with one or more moieties independently selected from C1-C3 alkyl;

$R_2$ is selected from C1-C3 alkyl, C1-C3 alkoxy, halogen, and hydroxy;

$R_3$, $R_4$, $R_5$, and $R_6$ are independently selected from H and F; and any alkyl is optionally substituted with one or more halogens.

In some embodiments of a compound of formula (I), each $R_1$ is independently selected from C1-C3 alkyl, cyclopropyl, 5- or 6-membered heteroaryl, hydroxy, and halogen; and when n is at least 2, two $R_1$ attached to adjacent atoms of the phenyl ring, together with the atoms to which they are attached, may form a 5- or 6-membered non-aromatic ring optionally containing one or more heteroatoms and optionally substituted with one or more moieties independently selected from C1-C3 alkyl;

$R_2$ is selected from C1-C3 alkyl, C1-C3 alkoxy, halogen, and hydroxy;

$R_3$, $R_4$, $R_5$, and $R_6$ are independently selected from H and F; and any alkyl is optionally substituted with one or more halogens.

In some embodiments of a compound of formula (I), each $R_1$ is independently selected from methyl, trifluoromethyl, isopropyl, cyclopropyl, pyridyl, hydroxy, and halogen; and when n is at least 2, two $R_1$ attached to adjacent atoms of the phenyl ring, together with the atoms to which they are attached, may form a 5-membered non-aromatic ring optionally containing one or more heteroatoms and optionally substituted with one or more methyl;

$R_2$ is selected from methyl, trifluoromethyl, methoxy, halogen, and hydroxy; and $R_3$, $R_4$, $R_5$, and $R_6$ are independently selected from H and F.

In some embodiments of a compound of formula (I), each $R_1$ is independently selected from methyl, trifluoromethyl, isopropyl, cyclopropyl, pyridyl, hydroxy, and halogen (e.g. Cl and Br);

$R_2$ is selected from methyl, trifluoromethyl, methoxy, halogen (e.g. F, Cl and Br), and hydroxy; and $R_3$, $R_4$, $R_5$, and $R_6$ are independently selected from H and F.

In some embodiments of a compound of formula (I), each $R_1$ is independently selected from methyl, trifluoromethyl, isopropyl, cyclopropyl, hydroxy, and halogen;

$R_2$ is selected from methyl, trifluoromethyl, methoxy, halogen, and hydroxy; and $R_3$, $R_4$, $R_5$, and $R_6$ are independently selected from H and F.

In some embodiments of a compound of formula (I), each $R_1$ is independently selected from methyl, trifluoromethyl, isopropyl, cyclopropyl, hydroxy, Cl and Br;

$R_2$ is selected from methyl, trifluoromethyl, methoxy, F, Cl, Br, and hydroxy; and $R_3$, $R_4$, $R_5$, and $R_6$ are independently selected from H and F.

In some further embodiments of a compound of formula (I), each $R_1$ is independently selected from C1-C6 alkyl, C3-C6 cycloalkyl, 5- or 6-membered heteroaryl, and halogen; and when n is at least 2, two $R_1$ attached to adjacent atoms of the phenyl ring, together with the atoms to which they are attached, may form a 4- to 6-membered (preferably non-aromatic) ring optionally containing one or more heteroatoms and optionally substituted with one or more moieties independently selected from C1-C3 alkyl;

$R_2$ is selected from C1-C6 alkyl, C1-C6 alkoxy, halogen, and hydroxy;

$R_3$, $R_4$, $R_5$, and $R_6$ are independently selected from H and F; and any alkyl is optionally substituted with one or more halogens.

In some embodiments of a compound of formula (I), each $R_1$ is independently selected from C1-C3 alkyl, cyclopropyl, 5- or 6-membered heteroaryl, and halogen; and when n is at least 2, two $R_1$ attached to adjacent atoms of the phenyl ring, together with the atoms to which they are attached, may form a 5- or 6-membered non-aromatic ring optionally containing one or more heteroatoms and optionally substituted with one or more moieties independently selected from C1-C3 alkyl;

$R_2$ is selected from C1-C3 alkyl, C1-C3 alkoxy, halogen, and hydroxy;

$R_3$, $R_4$, $R_5$, and $R_6$ are independently selected from H and F; and any alkyl is optionally substituted with one or more halogens.

In some embodiments of a compound of formula (I), each $R_1$ is independently selected from C1-C3 alkyl, cyclopropyl, 5- or 6-membered heteroaryl, and halogen; and when n is at least 2, two $R_1$ attached to adjacent atoms of the phenyl ring, together with the atoms to which they are attached, may form a 5- or 6-membered non-aromatic ring optionally containing one or more heteroatoms and optionally substituted with one or more moieties independently selected from C1-C3 alkyl;

$R_2$ is selected from C1-C3 alkyl, C1-C3 alkoxy, halogen, and hydroxy;

$R_3$, $R_4$, $R_5$, and $R_6$ are independently selected from H and F; and any alkyl is optionally substituted with one or more halogens.

In some embodiments of a compound of formula (I), each $R_1$ is independently selected from methyl, trifluoromethyl, isopropyl, cyclopropyl, pyridyl, and halogen; and when n is at least 2, two $R_1$ attached to adjacent atoms of the phenyl ring, together with the atoms to which they are attached, may form a 5-membered non-aromatic ring optionally containing one or more heteroatoms and optionally substituted with one or more methyl;

$R_2$ is selected from methyl, trifluoromethyl, methoxy, halogen, and hydroxy; and $R_3$, $R_4$, $R_5$, and $R_6$ are independently selected from H and F.

In some embodiments of a compound of formula (I), each $R_1$ is independently selected from methyl, trifluoromethyl, isopropyl, cyclopropyl, pyridyl, and halogen (e.g. Cl and Br);

$R_2$ is selected from methyl, trifluoromethyl, methoxy, halogen (e.g. F, Cl and Br), and hydroxy; and $R_3$, $R_4$, $R_5$, and $R_6$ are independently selected from H and F.

In some embodiments of a compound of formula (I), each $R_1$ is independently selected from methyl, trifluoromethyl, isopropyl, cyclopropyl, and halogen;

$R_2$ is selected from methyl, trifluoromethyl, methoxy, halogen, and hydroxy; and $R_3$, $R_4$, $R_5$, and $R_6$ are independently selected from H and F.

In some embodiments of a compound of formula (I), each $R_1$ is independently selected from methyl, trifluoromethyl, isopropyl, cyclopropyl, Cl and Br;

$R_2$ is selected from methyl, trifluoromethyl, methoxy, F, Cl, Br, and hydroxy; and $R_3$, $R_4$, $R_5$, and $R_6$ are independently selected from H and F.

In some of the above embodiments, $R_2$ is selected from C1-C3 alkyl (optionally substituted by one or more halogen), halogen, and hydroxy, e.g. methyl, trifluoromethyl, chloro and hydroxy, in particular methyl, chloro and hydroxy. In some of the above embodiments, $R_2$ is hydroxy. In some others of the above embodiments, $R_2$ is methyl or trifluoromethyl, in particular methyl. In still some others of the above embodiments, $R_2$ is halogen, e.g. chloro.

In still some further embodiments, each $R_1$ (including, when present, $R_{1a}$) and $R_2$ are independently selected from C1-C3 alkyl, hydroxy, and halogen (e.g. methyl, hydroxy, F, Cl, and Br), wherein any alkyl is optionally substituted by one or more halogen; e.g. $R_1$ is selected from C1-C3 alkyl, hydroxy, and halogen, and $R_2$ is hydroxy.

Compounds of formula (I) may be prepared by following methods generally well-known to the person of ordinary skill in the art of chemical synthesis, in light of the below described illustrating examples. For example, the compounds of the invention may be prepared by reacting a suitably substituted benzenesulfonyl chloride 1 with amine 2, as illustrated in Reaction Scheme 1.

Reaction Scheme 1

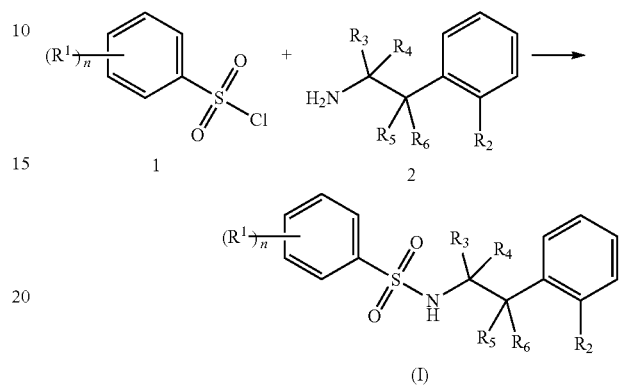

The reaction as illustrated in Reaction Scheme 1 may be performed at any suitable temperature, preferably room temperature, in a suitable solvent for the reactants, such as dichloromethane, and preferably in the presence of a suitable base, e.g. triethylamine.

The compounds of the present invention are Nox4 inhibitors and/or Nox2 inhibitors. Some of the compounds have a high selectivity for Nox4 and therefore may be used in diseases involving (associated with activity of) Nox4. Some of the compounds are capable of inhibiting both Nox2 and Nox4, and therefore may be used in diseases involving (associated with activity of) either Nox2 or Nox4, or—advantageously—both Nox2 and Nox4. Some of the compounds have a high selectivity for Nox2 and therefore may be used in diseases involving (associated with activity of) Nox2.

For example, in some embodiments, a compound of formula (I), e.g. a compound wherein $R_2$ is hydroxy or hydroxy-C1-C3 alkyl (in particular hydroxy), is useful as a Nox2 and Nox4 inhibitor, in particular as a Nox2 inhibitor.

In some advantageous embodiments, the compound of formula (I) is an inhibitor of both Nox2 and Nox4.

In some further embodiments, a compound of formula (I), e.g. a compound of formula (I) wherein $R_2$ is not selected from hydroxy and hydroxy-C1-C3 alkyl (e.g. $R_2$ is selected from C1-C6 alkyl and halogen, such as C1-C6 alkyl) is useful in particular as a Nox4 inhibitor.

Depending on the process conditions a compound of the invention may be obtained in neutral, but also as a salt form. Acid addition salts of the inventive compound may in a manner known per se be transformed into the free base using basic agents such as alkali or by ion exchange.

The free base obtained may also form salts with organic or inorganic acids. Alkali addition salts of the inventive compound may in a manner known per se be transformed into the free acid by using acidic agents such as acid or by ion exchange. The free acid obtained may also form salts with organic or inorganic bases.

In the preparation of acid or base addition salts, preferably such acids or bases are used which form suitably therapeutically acceptable salts. Examples of such acids are hydrohalogen acids, sulfuric acid, phosphoric acid, nitric acid, aliphatic, alicyclic, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, methanesulfonic acid, ethanesulfonic acid, hydroxyethanesulfonic acid, halogenbenzenesulfonic acid, toluenesulfonic acid or naphthalenesulfonic acid. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Examples of bases useful in preparing salts of the present invention include sodium hydroxide, potassium hydroxide, ammonium hydroxide, potassium carbonate, and the like.

Pharmaceutical formulations are usually prepared by mixing the active substance, i.e. a compound of formula (I), or a pharmaceutically acceptable salt thereof, with conventional pharmaceutical excipients. The formulations can be further processed by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner.

For clinical use, a compound of formula (I) is formulated into pharmaceutical formulations for oral, rectal, parenteral or other mode of administration. These pharmaceutical preparations are a further object of the invention.

Usually the effective amount of active compound is between 0.1-95% by weight of the preparation, preferably between 0.2-20% by weight in preparations for parenteral use and preferably between 1 and 50% by weight in preparations for oral administration.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

In the preparation of pharmaceutical formulations containing the compound of the present invention in the form of dosage units for oral administration the compound may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatine capsules may be prepared with capsules containing a mixture of the active compound of the invention, vegetable oil, fat, or other suitable vehicle for soft gelatine capsules. Hard gelatine capsules may contain granules of the active compound. Hard gelatine capsules may also contain the inventive compound in combination with solid powdered ingredients such as lactose, saccharose, sorbitol, mannitol, potato starch, corn starch, amylopectin, cellulose derivatives or gelatine.

Dosage units for rectal administration may be prepared (i) in the form of suppositories which contain the active substance mixed with a neutral fat base; (ii) in the form of a gelatine rectal capsule which contains the active substance in a mixture with a vegetable oil, paraffin oil or other suitable vehicle for gelatine rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral, e.g. intravenous administration, or for administration e.g. to the eye, may be prepared as a solution of a compound of the invention in a pharmaceutically acceptable solvent, preferably in a concentration from 0.01 to 10% by weight, or from 0.1% to 10% by weight. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

The compounds of formula (I) may also be used or administered in combination with one or more additional therapeutically active agents. The components may be in the same formulation or in separate formulations for administration simultaneously or sequentially.

Accordingly, in a further aspect of the invention, there is provided a combination product comprising:

(A) a compound of formula (I) as defined herein; and (B) another therapeutic agent; whereby (A) and (B) is formulated in admixture with a pharmaceutically acceptable excipient.

Such combination products provide for the administration of the compound of formula (I) in conjunction with the other therapeutic agent, and may thus be presented either as separate formulations, wherein at least one of those formulations comprises the compound of formula (I), and at least one comprises the other therapeutic agent, or may be presented (i.e. formulated) as a combined preparation (i.e. presented as a single formulation including a compound of formula (I) and the other therapeutic agent).

Thus, there is further provided:

(1) a pharmaceutical formulation including a compound of formula (I), another therapeutic agent, and a pharmaceutically acceptable excipient, e.g. an adjuvant, diluent or carrier; or (2) a kit of parts comprising, as components:

(a) a pharmaceutical formulation including a compound of formula (I), as defined herein, in admixture with a pharmaceutically acceptable excipient, e.g. an adjuvant, diluent or carrier; and (b) a pharmaceutical formulation including another therapeutic agent in admixture with a pharmaceutically acceptable excipient, e.g. an adjuvant, diluent or carrier, which components (a) and (b) are each provided in a form that is suitable for administration in conjunction with the other.

In some embodiments, the compound of formula (I) (or a pharmaceutically acceptable salt thereof) is for use in the treatment of an endocrine disorder. In some embodiments, the compound of formula (I) is for use in the treatment of a cardiovascular disorder or disease. In some embodiments, the compound of formula (I) is for use in the treatment of a respiratory disorder or disease. In some embodiments, the compound of formula (I) is for use in the treatment of an allergic disorder. In some embodiments, the compound of formula (I) is for use in the treatment of a traumatism. In some embodiments, the compound of formula (I) is for use in the treatment of a disease or disorder affecting the metabolism. In some embodiments, the compound of formula (I) is for use in the treatment of a skin disease or disorder. In some embodiments, the compound of formula (I) is for use in the treatment of a bone disorder. In some embodiments, the compound of formula (I) is for use in the treatment of a neurodegenerative disease or disorder, e.g. Alzheimer's disease. In some embodiments, the compound of formula (I) is for use in the treatment of a kidney disease or disorder. In some embodiments, the compound of formula (I) is for use in the treatment of a reproduction disorder or disease. In some embodiments, the compound of formula (I) is for use in the treatment of a disease or disorder affecting the eye and/or the lens. In some embodiments, the compound of formula (I) is for use in the treatment of a conditions affecting the inner ear. In some embodiments, the compound of formula (I) is for use in the treatment of an inflammatory disorder. In some embodiments, the compound of formula (I) is for use in the treatment of liver disease or disorders. In some embodiments, the compound of formula (I) is for use in the treatment of arthritis. In some embodiments, the compound of formula (I) is for use in the treatment of pain, e.g. hyperalgesia associated with inflammatory pain. In some embodiments, the compound of formula (I) is for use in the treatment of cancer, e.g. breast cancer. In some embodiments, the compound of formula (I) is for use in the treatment of a disease or disorder of the gastrointestinal system. In some embodiments, the compound of formula (I) is for use in the treatment of abnormal angiogenesis.

In still further embodiments, the compound of formula (I) is for use in the treatment of fibrosis. In some of these embodiments, the fibrosis is pulmonary fibrosis. In some other of these embodiments, the fibrosis is cystic fibrosis. In still of these embodiments, the fibrosis is liver fibrosis, e.g. alcohol induced liver fibrosis. In still further embodiments, the compound of formula (I) is for use in the treatment of diabetes, e.g. type 2 diabetes. In still further embodiments, the compound of formula (I) is for use in the treatment of chronic kidney disease (also referred to as chronic kidney failure). In some embodiments, the compound of formula (I) is for use in the manufacturing of a medicament for the treatment of any of the aforementioned diseases or disorders.

In some particular embodiments, the compounds disclosed herein are useful in the treatment of ischemic retinopathies, such as diabetic retinopathy. Thus, in some embodiments, a compound according to the invention is provided for use in the treatment of retinopathy, e.g. an ischemic retinopathy, such as diabetic retinopathy. The compound may be provided in formulation suitable for administration to the eye, e.g. an eye drop formulation, optionally containing one or more further active ingredients, e.g. an anti-inflammatory agent.

In some further embodiments, a compound of formula (I) is used in a combination with an antitumor agent in the treatment of a malignant hyperproliferative disease. Such combination therapy may be particularly useful in cancer chemotherapy, to counteract an anti-apoptotic effect of Nox4 that may lead to tumor resistance to the antitumor agent. Thus, there is further provided:

(1) a pharmaceutical formulation including a compound of formula (I), as hereinbefore defined, an antitumor agent, and a pharmaceutically acceptable excipient, e.g. an adjuvant, diluent or carrier; or (2) a kit of parts comprising, as components:

(a) a pharmaceutical formulation including a compound of formula (I), as defined herein, in admixture with a pharmaceutically acceptable excipient, e.g. an adjuvant, diluent or carrier; and (b) a pharmaceutical formulation including an antitumor agent in admixture with a pharmaceutically acceptable excipient, e.g. an adjuvant, diluent or carrier, which components (a) and (b) are each provided in a form that is suitable for administration in conjunction with the other.

The components (a) and (b) in any of the above kit of parts may be administered at the same time, in sequence, or separately from each other. The compound of the present invention may also be used or administered in combination with other modes of treatment, such as irradiation for the treatment of cancer.

According to one aspect, there is provided a method of inhibiting the activity of Nox4, in a patient in need thereof, by administering to said patient a therapeutically effective amount of a compound of formula (I), as defined herein. The patient may be any mammal, but preferably is a human. The patient to be treated may be one suffering from a condition or disorder associated with an elevated activity of Nox4, or a patient at risk of developing such a condition or disorder. Examples of such conditions and disorders are cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, diseases or disorders of the gastrointestinal system, angiogenesis, angiogenesis-dependent conditions, lung infections, acute lung injury, pulmonary arterial hypertension, obstructive lung disorders, fibrotic lung disease, and lung cancer.

In one embodiment, the compound of the present invention is for use in the treatment of stroke. In one particular embodiment, the stroke is ischemic. The compound of the present invention is considered to have neuroprotective activity in the treatment of stroke. Therefore, the compound of the present invention suitably is used in combination with removal of blood clots in the treatment of ischemic stroke. In one particular embodiment, the compound of the present invention is used in combination with tPA (tissue plasminogen activator) in the treatment of ischemic stroke.

A compound of formula (I) is useful for the treatment of any mammal subject, e.g. a human or an animal (a non-human mammal). In some embodiments, the treated subject is a human. In some other embodiments, the treated subject is a non-human mammal, e.g. a farm animal, a pet animal, or a laboratory animal. In some embodiments, the treated non-human mammal is a pet animal. In some embodiments, the pet animal is a dog. In some other embodiments, the pet animal is a cat. In other embodiments, the treated subject is a farm animal, e.g. a cow, or a pig, or a sheep. In other embodiments, the treated subject is a horse.

The invention will be illustrated by the following, non-limiting Examples.

EXAMPLES

In the Examples, flash column chromatography was performed on a Teledyne ISCO, Combi Flash Rf+Lumen using a RediSep Rf silica column. Preparative HPLC was performed on a Gilson system equipped with a UV detector using an XBridge Prep C-18 5 µm OBD, 50×19 mm column. Analytical HPLC-MS was performed using an Agilent 1100 series Liquid Chromatograph/Mass Selective Detector (MSD) (Single Quadrupole) equipped with an electrospray interface and a UV diode array detector. Analyses were performed by two methods using either an ACE 3 C8 (3.0×50 mm) column with a gradient of acetonitrile in 0.1% aqueous TFA over 3 min and a flow of 1 mL/min, or an Xbridge C18 (3.0×50 mm) column with a gradient of acetonitrile in 10 mM ammonium bicarbonate over 3 min and a flow of 1 mL/min. $^1$H-NMR spectra were recorded on a Varian 400 MHz instrument at 25° C.

The compounds have been named using the software MarvinSketch 16.2.29.0. In addition, the commercial names or trivial names are used for the commercial starting materials and reagents.

Example 1

N-[2-(2-methoxyphenyl)ethyl]-2,4,6-trimethylbenzene-1-sulfonamide 2,4,6-Trimethylbenzenesulfonyl chloride (38 mg, 0.17 mmol) was dissolved in DCM (2 mL) and 2-(2-methoxyphenyl)ethanamine (45 mg, 0.30 mmol) was added followed by triethylamine (50 µL, 0.35 mmol). The reaction mixture was stirred for 2 hours at room temperature. Water (1 mL) was added. The layers were separated and the organic phase was concentrated. Purification by preparative HPLC (XBridge C18 19×50 mm; 0.1% TFA(aq)/MeCN; 80:20 to 30:70) afforded the title compound as a white solid (8.7 mg, 15%). MS ESI+ m/z 334 [M+H]$^+$.

Example 2

N-[2-(2-fluorophenyl)ethyl]-2,4,6-trimethylbenzene-1-sulfonamide 2,4,6-Trimethylbenzenesulfonyl chloride (38 mg, 0.17 mmol) was dissolved in DCM (2 mL) and 2-(2-fluorophenyl)ethanamine (41.1 mg, 0.30 mmol) was added followed by triethylamine (50 µL, 0.35 mmol). The reaction mixture was stirred for 2 hours at room temperature. Water (1 mL) was added. The layers were separated and the organic phase was concentrated. Purification by preparative HPLC (XBridge C18 19×50 mm; 0.1% TFA(aq)/MeCN; 80:20 to 30:70) afforded the title compound as a white solid (4.6 mg, 8%). MS ESI+ m/z 322 [M+H]$^+$.

Example 3

N-[2-(2-fluorophenyl)ethyl]-2,2,4,6,7-pentamethyl-2,3-dihydro-1-benzofuran-5-sulfonamide 2,2,4,6,7-Pentamethyl-3H-benzofuran-5-sulfonyl chloride (27 mg, 0.09 mmol) was dissolved in DCM (2 mL) and 2-(2-fluorophenyl)ethanamine (22 mg, 0.16 mmol) was added followed by triethylamine (50 µL, 0.35 mmol). The reaction mixture was stirred for 1 hour at room temperature. Water (1 mL) was added. The layers were separated and the organic phase was concentrated. Purification by preparative HPLC (XBridge C18 19×50 mm; 0.1% TFA(aq)/MeCN; 80:20 to 30:70) afforded the title compound as a white solid (36.6 mg, 22%). MS ESI+ m/z 392 [M+H]$^+$.

Example 4

4-bromo-2,6-dichloro-N-[2-(2-methoxyphenyl)ethyl]benzene-1-sulfonamide 4-Bromo-2,6-dichloro-benzenesulfonyl chloride (25 mg, 0.08 mmol) was dissolved in DCM (2 mL) and 2-(2-methoxyphenyl)ethanamine (20 mg, 0.13 mmol) was added followed by triethylamine (50 µL, 0.46 mmol). The reaction mixture was stirred for 1 hour at room temperature. Water (1 mL) was added. The layers were separated and the organic phase was concentrated. Purification by preparative HPLC (XBridge C18 19×50 mm; 0.1% TFA(aq)/MeCN; 80:20 to 30:70) afforded the title compound as a white solid (34 mg, 20%). MS ESI+ m/z 440 [M+H]$^+$.

Example 5

4-bromo-2,6-dichloro-N-[2-(2-fluorophenyl)ethyl]benzene-1-sulfonamide

4-Bromo-2,6-dichloro-benzenesulfonyl chloride (500 mg, 1.54 mmol) was dissolved in DCM (2 mL) and 2-(2-fluorophenyl)ethanamine (0.34 mL, 2.62 mmol) was added followed by triethylamine (0.43 mL, 3.08 mmol). The reaction mixture was stirred for 1 hour at room temperature. DCM (10 mL) and brine (10 mL) were added to the mixture. The layers were separated and the organic phase was dried over magnesium sulfate, filtered and the solvent was evaporated. Purification by column chromatography on silica gel with PE/DCM (60:40 to 40:60) afforded the title compound as pale yellow solid (484 mg, 73%). $^1$H NMR (400 MHz, CDCl$_3$) δ 2.88 (t, J=6.8 Hz, 2H), 3.30-3.41 (m, 2H), 5.25 (t, J=5.8 Hz, 1H), 6.95-7.01 (m, 1H), 7.04 (td, J=7.5, 0.9 Hz, 1H), 7.13 (td, J=7.5, 1.5 Hz, 1H), 7.17-7.25 (m, 1H), 7.58 (s, 2H). MS ESI+ m/z 428 [M+H]$^+$.

Example 6

N-[2-(2-chlorophenyl)ethyl]-2,4,6-trimethylbenzene-1-sulfonamide 2,4,6-Trimethylbenzenesulfonyl chloride (38 mg, 0.17 mmol) was dissolved in DCM (2 mL) and 2-(2-chlorophenyl)ethanamine (46 mg, 0.3 mmol) was added followed by triethylamine (50 µL, 0.35 mmol). The reaction mixture was stirred for 1 hour at room temperature. Water (1 mL) was added. The layers were separated and the organic phase was concentrated. Purification by preparative HPLC (XBridge C18 19×50 mm; 0.1% TFA(aq)/MeCN; 80:20 to 30:70) afforded the title compound as a white solid (7.9 mg, 13%). MS ESI+ m/z 338 [M+H]$^+$.

Example 7

N-[2-(2-bromophenyl)ethyl]-2,4,6-trimethylbenzene-1-sulfonamide 2,4,6-Trimethylbenzenesulfonyl chloride (38 mg, 0.17 mmol) was dissolved in DCM (2 mL) and 2-(2-bromophenyl)ethanamine (59 mg, 0.3 mmol) was added followed by triethylamine (50 μL, 0.35 mmol). The reaction mixture was stirred for 1 hour at room temperature. Water (1 mL) was added. The layers were separated and the organic phase was concentrated. Purification by preparative HPLC (XBridge C18 19×50 mm; 0.1% TFA(aq)/MeCN; 80:20 to 30:70) afforded the title compound as a white solid (7.9 mg, 13%). MS ESI+ m/z 384 [M+H]+.

Example 8

4-bromo-2-chloro-N-[2-(2-chlorophenyl)ethyl]benzene-1-sulfonamide

4-Bromo-2-chloro-benzenesulfonyl chloride (38 mg, 0.13 mmol) was dissolved in DCM (1 mL) and 2-(2-chlorophenyl)ethanamine (35 mg, 0.22 mmol) was added followed by triethylamine (38 μL, 0.27 mmol). The reaction mixture was stirred for 1 hour at room temperature. Water (1 mL) was added. The layers were separated and the organic phase was concentrated. Purification by preparative HPLC (XBridge C18 19×50 mm; 0.1% TFA(aq)/MeCN; 80:20 to 30:70) afforded the title compound as a white solid (7.8 mg, 15%). MS ESI+ m/z 410 [M+H]+.

Example 9

N-[2-(2-chlorophenyl)ethyl]-2,2,4,6,7-pentamethyl-2,3-dihydro-1-benzofuran-5-sulfonamide 2,2,4,6,7-Pentamethyl-3H-benzofuran-5-sulfonyl chloride (38 mg, 0.13 mmol) was dissolved in DCM (2 mL) and 2-(2-chlorophenyl)ethanamine (46 mg, 0.3 mmol) was added followed by triethylamine (50 μL, 0.35 mmol). The reaction mixture was stirred for 1 hour at room temperature. Water (1 mL) was added. The layers were separated and the organic phase was concentrated. Purification by preparative HPLC (XBridge C18 19×50 mm; 0.1% TFA(aq)/MeCN; 80:20 to 30:70) afforded the title compound as a white solid (6.9 mg, 10%). MS ESI+ m/z 408 [M+H]+.

Example 10

2,4,6-trimethyl-N-{2-[2-(trifluoromethyl)phenyl]ethyl}benzene-1-sulfonamide 2,4,6-Trimethylbenzenesulfonyl chloride (38 mg, 0.17 mmol) was dissolved in DCM (2 mL) and 2-[2-(trifluoromethyl)phenyl]ethanamine (56 mg, 0.3 mmol) was added followed by triethylamine (50 μL, 0.35 mmol). The reaction mixture was stirred for 1 hour at room temperature. Water (1 mL) was added. The layers were separated and the organic phase was concentrated. Purification by preparative HPLC (XBridge C18 19×50 mm; 0.1% TFA(aq)/MeCN; 80:20 to 30:70) afforded the title compound as a white solid (8.0 mg, 12%). MS ESI+ m/z 372 [M+H]+.

Example 11

2-chloro-6-methyl-N-[2-(2-methylphenyl)ethyl]benzene-1-sulfonamide

2-Chloro-6-methyl-benzenesulfonyl chloride (38 mg, 0.17 mmol) was dissolved in DCM (2 mL) and 2-(o-tolyl)ethanamine (40 mg, 0.30 mmol) was added followed by triethylamine (50 μL, 0.35 mmol). The reaction mixture was stirred for 1 hour at room temperature. Water (1 mL) was added. The layers were separated and the organic phase was concentrated. Purification by preparative HPLC (XBridge C18 19×50 mm; 0.1% TFA(aq)/MeCN; 80:20 to 30:70) afforded the title compound as a white solid (5.6 mg, 14%). MS ESI+ m/z 324 [M+H]+.

Example 12

2-chloro-N-[2-(2-chlorophenyl)ethyl]-6-methylbenzene-1-sulfonamide

2-Chloro-6-methyl-benzenesulfonyl chloride (38 mg, 0.17 mmol) was dissolved in DCM (2 mL) and 2-(2-chlorophenyl)ethanamine (46 mg, 0.3 mmol) was added followed by triethylamine (50 μL, 0.35 mmol). The reaction mixture was stirred for 1 hour at room temperature. Water (1 mL) was added. The layers were separated and the organic phase was concentrated. Purification by preparative HPLC (XBridge C18 19×50 mm; 0.1% TFA(aq)/MeCN; 80:20 to 30:70) afforded the title compound as a white solid (8.0 mg, 13%). MS ESI+ m/z 344 [M+H]+.

Example 13

2-chloro-N-[2-(2-chlorophenyl)ethyl]benzene-1-sulfonamide

2-Chlorobenzenesulfonyl chloride (38 mg, 0.18 mmol) was dissolved in DCM (2 mL) and 2-(2-chlorophenyl)ethanamine (46 mg, 0.3 mmol) was added followed by triethylamine (50 μL, 0.35 mmol). The reaction mixture was stirred for 1 hour at room temperature. Water (1 mL) was added. The layers were separated and the organic phase was concentrated. Purification by preparative HPLC (XBridge C18 19×50 mm; 0.1% TFA(aq)/MeCN; 80:20 to 30:70) afforded the title compound as a white solid (6.2 mg, 11%). MS ESI+ m/z 330 [M+H]+.

Example 14

2,4,6-trimethyl-N-[2-(2-methylphenyl)ethyl]benzene-1-sulfonamide 2,4,6-Trimethylbenzenesulfonyl chloride (38 mg, 0.17 mmol) was dissolved in DCM (2 mL) and 2-(o-tolyl)ethanamine (40 mg, 0.3 mmol) was added followed by triethylamine (50 μL, 0.35 mmol). The reaction mixture was stirred for 1 hour at room temperature. Water (1 mL) was added. The layers were separated and the organic phase was concentrated. Purification by preparative HPLC (XBridge C18 19×50 mm; 0.1% TFA(aq)/MeCN; 80:20 to 30:70) afforded the title compound as a white solid (1.1 mg, 2%). MS ESI+ m/z 318 [M+H]+.

Example 15

2,4,6-trimethyl-N-{2-[2-(trifluoromethoxy)phenyl]ethyl}benzene-1-sulfonamide 2,4,6-Trimethylbenzenesulfonyl chloride (38 mg, 0.17 mmol) was dissolved in DCM (2 mL) and 2-[2-(trifluoromethoxy)phenyl]ethanamine (61 mg, 0.3 mmol) was added followed by triethylamine (50 μL, 0.35 mmol). The reaction mixture was stirred for 1 hour at room temperature. Water (1 mL) was added. The layers were separated and the organic phase was concentrated. Purification by preparative HPLC (XBridge C18 19×50 mm; 0.1% TFA(aq)/MeCN;

80:20 to 30:70) afforded the title compound as a white solid (3.7 mg, 6%). MS ESI+ m/z 388 [M+H]+.

Example 16

2-chloro-6-methyl-N-{2-[2-(trifluoromethyl)phenyl]ethyl}benzene-1-sulfonamide

2-Chloro-6-methyl-benzenesulfonyl chloride (38 mg, 0.17 mmol) was dissolved in DCM (2 mL) and 2-[2-(trifluoromethyl)phenyl]ethanamine (56 mg, 0.3 mmol) was added followed by triethylamine (50 μL, 0.35 mmol). The reaction mixture was stirred for 1 hour at room temperature. Water (1 mL) was added. The layers were separated and the organic phase was concentrated. Purification by preparative HPLC (XBridge C18 19×50 mm; 0.1% TFA(aq)/MeCN; 80:20 to 30:70) afforded the title compound as a white solid (6.8 mg, 10%). MS ESI+ m/z 378 [M+H]+.

Example 17

4-bromo-2,6-dichloro-N-[2-(2-methylphenyl)ethyl]benzene-1-sulfonamide

4-Bromo-2,6-dichloro-benzenesulfonyl chloride (38 mg, 0.12 mmol) was dissolved in DCM (2 mL) and 2-(o-tolyl)ethanamine (40 mg, 0.3 mmol) was added followed by triethylamine (50 μL, 0.35 mmol). The reaction mixture was stirred for 1 hour at room temperature. Water (1 mL) was added. The layers were separated and the organic phase was concentrated. Purification by preparative HPLC (XBridge C18 19×50 mm; 0.1% TFA(aq)/MeCN; 80:20 to 30:70) afforded the title compound as a white solid (24 mg, 33%). MS ESI+ m/z 424 [M+H]+.

Example 18

2,4-dichloro-N-[2-(2-methylphenyl)ethyl]benzene-1-sulfonamide 2,4-Dichlorobenzenesulfonyl chloride (43 mg, 0.18 mmol) was dissolved in DCM (2 mL) and 2-(o-tolyl)ethanamine (40 mg, 0.3 mmol) was added followed by triethylamine (50 μL, 0.35 mmol). The reaction mixture was stirred for 1 hour at room temperature. Water (1 mL) was added. The layers were separated and the organic phase was concentrated. Purification by preparative HPLC (XBridge C18 19×50 mm; 0.1% TFA(aq)/MeCN; 80:20 to 30:70) afforded the title compound as a white solid (27 mg, 45%). MS ESI+ m/z 344 [M+H]+.

Example 19

4-bromo-2,6-dichloro-N-{2-[2-(trifluoromethyl)phenyl]ethyl}benzene-1-sulfonamide 4-Bromo-2,6-dichloro-benzenesulfonyl chloride (200 mg, 0.62 mmol) was dissolved in DCM (0.7 mL) and triethylamine (0.17 mL, 1.23 mmol) was added followed by 2-[2-(trifluoromethyl)phenyl]ethanamine (0.17 mL, 1.05 mmol). The reaction mixture was stirred for 1.5 hour at room temperature. DCM (10 mL) and brine (10 mL) were added to the mixture. The layers were separated and the organic phase was dried over magnesium sulfate, filtered and the solvent was evaporated. Purification by column chromatography on silica gel with petroleum ether/DCM (60:40 to 40:60) afforded the title compound as pale yellow solid (189 mg, 64%). MS ESI– m/z 476 [M–H]–.

Example 20

4-bromo-2,6-dichloro-N-[2-(2-chlorophenyl)ethyl]benzene-1-sulfonamide

4-Bromo-2,6-dichloro-benzenesulfonyl chloride (200 mg, 0.62 mmol) was dissolved in DCM (0.7 mL) and 2-(2-chlorophenyl)ethanamine (0.15 mL, 1.05 mmol) was added followed by triethylamine (0.17 mL, 1.23 mmol). The reaction mixture was stirred for 1.5 hour at room temperature. DCM (10 mL) and brine (10 mL) were added to the mixture. The layers were separated and the organic phase was dried over magnesium sulfate, filtered and the solvent was evaporated. Purification by column chromatography on silica gel with petroleum ether/DCM (60:40 to 40:60) afforded the title compound as white solid (231 mg, 84%). $^1$H NMR (400 MHz, CDCl$_3$) δ 2.97 (t, J=7.0 Hz, 2H), 3.31-3.43 (m, 2H), 5.25 (t, J=6.0 Hz, 1H), 7.15-7.21 (m, 3H), 7.29-7.34 (m, 1H), 7.58 (s, 2H). MS ESI– m/z 442 [M–H]–.

Example 21

2,6-dichloro-N-[2-(2-fluorophenyl)ethyl]benzene-1-sulfonamide 2,6-Dichlorobenzenesulfonyl chloride (100 mg, 0.41 mmol) was dissolved in DCM (0.5 mL) and triethylamine (0.11 mL, 0.81 mmol) was added followed by 2-(2-fluorophenyl)ethanamine (0.09 mL, 0.69 mmol). The reaction mixture was stirred for 1.5 hour at room temperature. DCM (10 mL) and brine (10 mL) were added to the mixture. The layers were separated and the organic phase was dried over magnesium sulfate, filtered and the solvent was evaporated. Purification by column chromatography on silica gel with petroleum ether/DCM (60:40 to 40:60) afforded the title compound as white solid (74 mg, 52%). $^1$H NMR (400 MHz, CDCl$_3$) δ 2.88 (t, J=6.9 Hz, 2H), 3.36-3.46 (m, 2H), 5.31 (t, J=5.7 Hz, 1H), 6.95-7.02 (m, 1H), 7.05 (td, J=7.5, 1.0 Hz, 1H), 7.14 (td, J=7.5, 1.6 Hz, 1H), 7.17-7.24 (m, 1H), 7.32 (dd, J=8.7, 7.3 Hz, 1H), 7.43 (s, 1H), 7.45 (d, J=0.7 Hz, 1H). MS ESI+ m/z 348 [M+H]+.

Example 22

2,6-dichloro-N-{2-[2-(trifluoromethyl)phenyl]ethyl}benzene-1-sulfonamide 2,6-Dichlorobenzenesulfonyl chloride (100 mg, 0.41 mmol) was dissolved in DCM (0.5 mL) and triethylamine (0.11 mL, 0.81 mmol) was added followed by 2-[2-(trifluoromethyl)phenyl]ethanamine (0.11 mL, 0.69 mmol). The reaction mixture was stirred for 2 hours at room temperature. DCM (10 mL) and brine (10 mL) were added to the mixture. The layers were separated and the organic phase was dried over magnesium sulfate, filtered and the solvent was evaporated. Purification by column chromatography on silica gel with petroleum ether/DCM (60:40 to 40:60) afforded the title compound as white solid (131 mg, 80%). MS ESI+ m/z 398 [M+H]+.

Example 23

2,6-dichloro-N-[2-(2-chlorophenyl)ethyl]benzene-1-sulfonamide 2,6-Dichlorobenzenesulfonyl chloride (100 mg, 0.41 mmol) was dissolved in DCM (0.5 mL) and triethylamine (0.11 mL, 0.81 mmol) was added followed by 2-(2-chlorophenyl)ethanamine (0.10 mL, 0.69 mmol). The reaction mixture was stirred for 2 hours at room temperature. DCM (10 mL) and brine (10 mL) were added to the mixture. The layers were separated and the organic phase was dried over magnesium sulfate, filtered and the solvent was evaporated. Purification by column chromatography on silica gel with petroleum ether/DCM (60:40 to 40:60) afforded the title compound as white solid (110 mg, 73%). MS ESI+ m/z 366 $[M+H]^+$.

Example 24

2,6-dichloro-N-[2-(2-fluorophenyl)ethyl]-4-(pyridin-3-yl)benzene-1-sulfonamide

4-Bromo-2,6-dichloro-N-[2-(2-fluorophenyl)ethyl]benzene-1-sulfonamide (50 mg, 0.12 mmol) and 3-pyridylboronic acid (17 mg, 0.14 mmol) were dissolved in DME (3 mL) and 2 M aqueous solution of $K_2CO_3$ (0.18 mL, 0.35 mmol) was added followed by $PdCl_2(dppf)$ (9.56 mg, 0.010 mmol). The reaction mixture was stirred for 16 hours at 80° C. under nitrogen atmosphere. DCM (10 mL) and brine (10 mL) were added to the mixture. The layers were separated and the organic phase was dried over magnesium sulfate, filtered and the solvent was evaporated. Purification by column chromatography on silica gel with petroleum ether/DCM (60:40 to 0:100) then with PE/EtOAc (60:40 to 30:70) afforded the title compound as pale yellow solid (38 mg, 74%). $^1$H NMR (400 MHz, $CDCl_3$) δ 2.91 (t, J=6.7 Hz, 2H), 3.36-3.46 (m, 2H), 5.44 (t, J=5.8 Hz, 1H), 6.99 (dd, J=11.6, 6.6 Hz, 1H), 7.05 (t, J=7.3 Hz, 1H), 7.19 (dt, J=15.1, 7.5 Hz, 2H), 7.68 (s, 2H), 7.81 (s, 1H), 8.28 (d, J=4.8 Hz, 1H), 8.81 (s, 1H), 8.98 (s, 1H). MS ESI+ m/z 425 $[M+H]^+$.

Example 25

2,6-dichloro-4-cyclopropyl-N-[2-(2-fluorophenyl)ethyl]benzene-1-sulfonamide

4-Bromo-2,6-dichloro-N-[2-(2-fluorophenyl)ethyl]benzene-1-sulfonamide (50 mg, 0.12 mmol) and potassium cyclopropyltrifluoroborate (21 mg, 0.14 mmol) were dissolved in DME (3 mL) and 2 M aqueous solution of $K_2CO_3$ (0.18 mL, 0.35 mmol) was added followed by $PdCl_2(dppf)$ (9.56 mg, 0.010 mmol). The reaction mixture was stirred for 16 hours at 80° C. under nitrogen atmosphere. DCM (10 mL) and brine (10 mL) were added to the mixture. The layers were separated and the organic phase was dried over magnesium sulfate, filtered and the solvent was evaporated. Purification by column chromatography on silica gel with petroleum ether/DCM (60:40 to 40:60) afforded the title compound as white solid (24 mg, purity 70%). MS ESI+ m/z 388 $[M+H]^+$.

Example 26

2,6-dichloro-N-[2-(2-chlorophenyl)ethyl]-4-cyclopropylbenzene-1-sulfonamide

4-Bromo-2,6-dichloro-N-[2-(2-chlorophenyl)ethyl]benzene-1-sulfonamide (50 mg, 0.12 mmol) and potassium cyclopropyltrifluoroborate (21 mg, 0.14 mmol) were dissolved in DME (3 mL) and 2 M aqueous solution of $K_2CO_3$ (0.18 mL, 0.35 mmol) was added followed by $PdCl_2(dppf)$ (9.6 mg, 0.010 mmol). The reaction mixture was stirred for 16 hours at 80° C. under nitrogen atmosphere. DCM (10 mL) and brine (10 mL) were added to the mixture. The layers were separated and the organic phase was dried over magnesium sulfate, filtered and the solvent was evaporated. Purification by column chromatography on silica gel with petroleum ether/DCM (60:40 to 40:60) afforded the title compound as white solid (24 mg, 46%). MS ESI+ m/z 406 $[M+H]^+$.

Example 27

2,6-dichloro-N-[2-(2-chlorophenyl)ethyl]-4-(trifluoromethyl)benzene-1-sulfonamide 2,6-Dichloro-4-(trifluoromethyl)benzenesulfonyl chloride (60 mg, 0.19 mmol) was dissolved in DCM (0.4 mL) and triethylamine (0.05 mL, 0.35 mmol) was added followed by 2-(2-chlorophenyl)ethanamine (0.05 mL, 0.33 mmol). The reaction mixture was stirred for 2 hours at room temperature. DCM (10 mL) and brine (10 mL) were added to the mixture. The layers were separated and the organic phase was dried over magnesium sulfate, filtered and the solvent was evaporated. Purification by column chromatography on silica gel with petroleum ether/DCM (60:40 to 40:60) afforded the title compound as white solid (51 mg, 60%). MS ESI– m/z 430 $[M-H]^-$.

Example 28

N-[2,2-difluoro-2-(2-methylphenyl)ethyl]-2,4,6-trimethylbenzene-1-sulfonamide 2,4,6-trimethylbenzenesulfonyl chloride (30 mg, 0.14 mmol) and 2,2-difluoro-2-(2methyl-phenyl)-ethan-1-amine hydrochloride (48 mg, 0.23 mmol) were dissolved in DCM (0.5 mL) and triethylamine (0.6 mL, 0.46 mmol) was added. The reaction mixture was stirred for 2 hours at room temperature. DCM (10 mL) and brine (10 mL) were added to the mixture. The layers were separated and the organic phase was dried over magnesium sulfate, filtered and the solvent was evaporated. Purification by column chromatography on silica gel with petroleum ether/DCM (60:40 to 40:60) afforded the title compound as white solid (34 mg, 69%). $^1$H NMR (400 MHz, $CDCl_3$) δ 2.29 (t, J=2.2 Hz, 3H), 2.30 (s, 3H), 2.57 (s, 6H), 3.63 (td, J=14.2, 6.7 Hz, 2H), 4.81 (t, J=6.5 Hz, 1H), 6.91 (s, 2H), 7.15 (dd, J=15.6, 7.8 Hz, 2H), 7.27-7.33 (m, 2H). MS ESI+ m/z 354 $[M+H]^+$.

Example 29

4-bromo-2,6-dichloro-N-[2,2-difluoro-2-(2-methylphenyl)ethyl]benzene-1-sulfonamide 4-Bromo-2,6-dichlorobenzenesulfonyl chloride (45 mg, 0.14 mmol) and 2,2-difluoro-2-(2methyl-phenyl)-ethan-1-amine hydrochloride (49 mg, 0.24 mmol) were dissolved in DCM (0.5 mL) and triethylamine (0.06 mL, 0.46 mmol) was added. The reaction mixture was stirred for 3 hours at room temperature and then DCM (10 mL) and brine (10 mL) were added. The layers were separated and the organic phase was dried over magnesium sulfate, filtered and the solvent was evaporated. Purification by column chromatography on silica gel with petroleum ether/DCM (100:0 to 95:5)

afforded the title compound as white solid (32 mg, 50%). $^1$H NMR (400 MHz, CDCl$_3$) δ 2.39 (t, J=2.1 Hz, 2H), 3.88 (td, J=14.5, 6.4 Hz, 1H), 5.76 (t, J=6.4 Hz, 1H), 7.08-7.18 (m, 2H), 7.27-7.36 (m, 2H), 7.56 (s, 2H). MS ESI– 458 [M–H]$^-$. Hr.

Example 30

N-[2-(2-chlorophenyl)-2,2-difluoroethyl]-2,4,6-trimethylbenzene-1-sulfonamide 2,4,6-Trimethylbenzene-1-sulfonyl chloride (50 mg, 0.23 mmol) was dissolved in DCM (1 mL) and 2-(2-chlorophenyl)-2,2-difluoroethan-1-amine (66 mg, 0.34 mmol) was added followed by triethylamine (0.1 mL, 0.69 mmol). The reaction mixture was stirred for 2 hours at room temperature. DCM (10 mL) and brine (10 mL) were added to the mixture. The layers were separated and the organic phase was dried over magnesium sulfate, filtered and the solvent was evaporated. Purification by column chromatography on silica gel with DCM/MeOH (100:0 to 99:1) afforded the title compound as colorless oil (63 mg, 74%). $^1$H NMR (400 MHz, CDCl$_3$) δ 2.29 (s, 3H), 2.53 (s, 6H), 3.88 (td, J=13.7, 7.0 Hz, 2H), 4.80 (t, J=7.0 Hz, 1H), 6.86 (s, 2H), 7.21-7.26 (m, 1H), 7.27-7.36 (m, 2H), 7.43 (dd, J=7.7, 1.6 Hz, 1H). MS ESI– 372 [M–H]$^-$.

Example 31

4-bromo-2,6-dichloro-N-[2-(2-chlorophenyl)-2,2-difluoroethyl]benzene-1-sulfonamide 4-Bromo-2,6-dichlorobenzenesulfonyl chloride (50 mg, 0.15 mmol) was dissolved in DCM (1 mL) and 2-(2-chlorophenyl)-2,2-difluoroethan-1-amine (50 mg, 0.26 mmol) was added followed by triethylamine (0.06 mL, 0.46 mmol). The reaction mixture was stirred for 2 hours at room temperature. DCM (10 mL) and brine (10 mL) were added to the mixture. The layers were separated and the organic phase was dried over magnesium sulfate, filtered and the solvent was evaporated. Purification by column chromatography on silica gel with DCM/MeOH (100:0 to 99:1) afforded the title compound as colorless oil (45 mg, 66%). $^1$H NMR (400 MHz, CDCl$_3$) δ, 4.11 (td, J=14.3, 6.5 Hz, 2H), 5.71 (t, J=6.5 Hz, 1H) 7.17-7.26 (m, 1H), 7.31-7.39 (m, 2H), 7.43-7.51 (m, 1H), 7.55 (s, 2H). MS ESI– 478 [M–H]$^-$.

Example 32

N-[2-(2-chlorophenyl)ethyl]-2,6-dimethyl-4-(propan-2-yl)benzene-1-sulfonamide

4-Isopropyl-2,6-dimethyl-benzenesulfonylchloride (50 mg, 0.20 mmol) was dissolved in DCM (0.5 mL) and 2-(2-chlorophenyl)ethylamine (48 μL, 0.34 mmol) was added followed by triethylamine (0.08 mL, 0.61 mmol). The reaction mixture was stirred for 2 hours at room temperature. DCM (10 mL) and brine (10 mL) were added to the mixture. The layers were separated and the organic phase was dried over magnesium sulfate, filtered and the solvent was evaporated. Purification by column chromatography on silica gel with petroleum ether/DCM (65:35 to 40:60) afforded the title compound as colorless oil (56 mg, 75%). MS ESI– m/z 364 [M–H]$^-$.

Example 33

2,6-dimethyl-N-[2-(2-methylphenyl)ethyl]-4-(propan-2-yl)benzene-1-sulfonamide

4-Isopropyl-2,6-dimethyl-benzenesulfonylchloride (50 mg, 0.20 mmol) was dissolved in DCM (0.5 mL) and 2-(2-methylphenyl)ethylamine (50 μL, 0.34 mmol) was added followed by triethylamine (0.08 mL, 0.58 mmol) The reaction mixture was stirred for 2 hours at room temperature. DCM (10 mL) and brine (10 mL) were added to the mixture. The layers were separated and the organic phase was dried over magnesium sulfate, filtered and the solvent was evaporated. Purification by column chromatography on silica gel with petroleum ether/DCM (65:35 to 40:60) afforded the title compound as colorless oil (43 mg, 60%). $^1$H NMR (400 MHz, CDCl$_3$) δ 1.23 (s, 3H), 1.24 (s, 3H), 2.17 (s, 3H), 2.56 (s, 6H), 2.79 (t, J=7.1 Hz, 2H), 2.84 (hept, J=9.7 Hz, 1H), 3.07-3.18 (m, 2H), 4.41 (t, J=6.2 Hz, 1H), 6.96 (s, 2H), 6.99-7.03 (m, 1H), 7.07-7.16 (m, 3H). MS ESI– m/z 344 [M–H]$^-$.

Example 34

N-[2-fluoro-2-(2-methylphenyl)ethyl]-2,4,6-trimethylbenzene-1-sulfonamide 2,4,6-Trimethylbenzene-1-sulfonyl chloride (50 mg, 0.23 mmol) was dissolved in DCM (1 mL) and 2-fluoro-2-(2-methylphenyl)ethan-1-amine (52 mg, 0.34 mmol) was added followed by triethylamine (0.1 mL, 0.69 mmol). The reaction mixture was stirred for 2 hours at room temperature. DCM (10 mL) and brine (10 mL) were added to the mixture. The layers were separated and the organic phase was dried over magnesium sulfate, filtered and the solvent was evaporated. Purification by column chromatography on silica gel with DCM/MeOH (100:0 to 99:1) afforded the title compound as colorless oil (45 mg, 59%). $^1$H NMR (400 MHz, CDCl$_3$) δ 2.18 (s, 3H), 2.30 (s, 3H), 2.64 (s, 6H), 3.13 (dddd, J=16.3, 14.5, 8.9, 3.5, 1H), 3.26 (dddd, J=32.5, 14.5, 9.1, 2.9, 1H), 5.02 (dd, J=9.1, 3.5 Hz, 1H), 5.61 (ddd, J=47.9, 8.9, 2.9 Hz, 1H), 6.96 (s, 2H), 7.09-7.14 (m, 1H), 7.17-7.30 (m, 4H). $^{19}$F NMR (376 MHz, CDCl$_3$) δ –185.14 (ddd, J=47.9, 32.5, 16.3 Hz). MS ESI+ m/z 336 [M+H]$^+$.

Example 35

4-bromo-2,6-dichloro-N-[2-fluoro-2-(2-methylphenyl)ethyl]benzene-1-sulfonamide

4-Bromo-2,6-dichlorobenzenesulfonyl chloride (50 mg, 0.15 mmol) was dissolved in DCM (1 mL) and 2-fluoro-2-(2-methylphenyl)ethan-1-amine (35 mg, 0.23 mmol) was added followed by triethylamine (60 μL, 0.45 mmol). The reaction mixture was stirred for 2 hours at room temperature. DCM (10 mL) and brine (10 mL) were added to the mixture. The layers were separated and the organic phase was dried over magnesium sulfate, filtered and the solvent was evaporated. Purification by column chromatography on silica gel with DCM/MeOH (100:0 to 99:1) afforded the title compound as white solid (45 mg, 66%). $^1$H NMR (400 MHz, CDCl$_3$) δ 2.22 (s, 3H), 3.28 (dddd, J=17.2, 14.7, 8.5, 4.4 Hz, 1H), 3.49 (dddd, J=31.4, 14.7, 8.2, 2.8 Hz, 1H), 5.63 (ddd, J=47.8, 8.5, 2.8 Hz, 1H), 5.69-5.73 (m, 1H), 7.04-7.18 (m, 3H), 7.20-7.25 (m, 1H), 7.56 (s, 2H). $^{19}$F NMR (376 MHz, CDCl$_3$) δ –185.14 (ddd, J=47.8, 31.4, 17.2 Hz). MS ESI– m/z 440 [M–H]$^-$.

The compound of Example 35 exists as 2 optical isomers (enantiomers). The two isomers were separated using Supercritical Fluid Chromatography (SFC), as follows: The racemate (65 mg) was dissolved in 1.2 mL of methanol (MeOH) and the preparative chromatography was performed by stacked injections of 100 μL of this solution on an SFC system connected to a photodiode array (PDA) detector. The column used was a 5 μm, YMC Chiral Cellulose-SC, 10 mm×250 mm (diameter×length) column and the column temperature was set to 45° C. An isocratic condition of 20% MeOH in $CO_2$ was applied at a flow rate of 15 mL/min. The back pressure was set to 120 Bar. The PDA scanned from 220 to 400 and the enantiomers were collected in separate fractions (with the aid of up to 2 mL/min of MeOH as make up solvent for the collection) and pooled from each injection. In this system, the retention time of enantiomer 1 (isomer 1) was 2.43 min (2.26-2.57 min) and that of enantiomer 2 (isomer 2) was 2.72 min (2.59-2.97 min). An amount of 20 mg of each enantiomer was obtained. The enantiomeric ratio was >99% for each of the two isolated isomers.

Example 36

N-[2-fluoro-2-(2-methylphenyl)ethyl]-2,6-dimethyl-4-(propan-2-yl)benzene-1-sulfonamide 4-Isopropyl-2,6-dimethylbenzenesulfonyl chloride (50 mg, 0.20 mmol) was dissolved in DCM (1 mL) and 2-fluoro-2-(2-methylphenyl)ethan-1-amine (47 mg, 0.30 mmol) was added followed by triethylamine (0.09 mL, 0.60 mmol). The reaction mixture was stirred for 2 hours at room temperature. DCM (10 mL) and brine (10 mL) were added to the mixture. The layers were separated and the organic phase was dried over magnesium sulfate, filtered and the solvent was evaporated. Purification by column chromatography on silica gel with DCM/MeOH (100:0 to 99:1) afforded the title compound as white solid (52 mg, 71%). $^1$H NMR (400 MHz, $CDCl_3$) δ 1.24 (d, J=6.9 Hz, 6H), 2.15 (s, 3H), 2.66 (s, 6H), 2.85 (hept, J=6.9 Hz, 1H), 3.22 (dddd, J=16.5, 14.7, 8.8, 3.6 Hz, 1H), 3.33 (dddd, J=32.4, 14.7, 9.2, 2.9 Hz, 1H), 5.03 (dd, J=9.2, 3.6 Hz, 1H), 5.60 (ddd, J=48.0, 8.8, 2.9 Hz, 1H), 6.99 (s, 2H), 7.08-7.15 (m, J=6.9 Hz, 1H), 7.16-7.30 (m, 3H). $^{19}$F NMR (376 MHz, $CDCl_3$) δ −185.14 (ddd, J=48.0, 32.4, 16.5 Hz). MS ESI+ m/z 364 $[M+H]^+$.

Example 37

N-[2-(2-hydroxyphenyl)ethyl]-2,4,6-trimethylbenzene-1-sulfonamide 2-(2-Aminoethyl)phenol (53 mg, 0.39 mmol) was dissolved in DCM (2 mL) and TMS-Cl (49 μL, 0.39 mmol) was added followed by triethylamine (0.1 mL, 0.69 mmol). The reaction mixture was stirred for 30 minutes at room temperature then 2,4,6-trimethylbenzenesulfonyl chloride (50 mg, 0.23 mmol) was added. The reaction mixture was stirred for 1 hour. Acidic water (1 mL) was added and the mixture was stirred for few minutes, the phases were separated and the organic phase was evaporated. Purification by column chromatography on silica gel with DCM/MeOH (100:0 to 97:3) afforded the title compound as yellow solid (45 mg, 61%). MS ESI+ m/z 320 $[M+H]^+$.

Example 38

4-bromo-2,6-dichloro-N-[2-(2-hydroxyphenyl)ethyl]benzenesulfonamide 2-(2-aminoethyl)phenol (53 mg, 0.39 mmol) was dissolved in DCM (2 mL) and TMS-Cl (50 μL, 0.40 mmol) was added followed by triethylamine (100 μL, 0.73 mmol). The reaction mixture became clear and was stirred for 20 minutes before 4-bromo-2,6-dichloro-benzenesulfonyl chloride (74 mg, 0.23 mmol) was added. The reaction mixture was stirred for 1 h before water (2 mL) was added. The reaction mixture was stirred for 5 minutes and the organic phase was collected. The aqueous phase was extracted with DCM (2 mL) and the combined organics were dried ($MgSO_4$) and concentrated. The mixture was dissolved in acetonitrile (1 mL) and 1 drop of 2N HCl was added and the reaction mixture was allowed to stir for 10 minutes. The reaction mixture was concentrated and purified by column chromatography on silica gel with DCM/MeOH (95:5) as eluent. Yield 40 mg (41%). MS ESI$^+$ m/z 426 $[M+H]^+$. 1H NMR (CDCl3) 2.85 (t, J=6.6 Hz, 2H), 3.35 (t, J=6.6 Hz, 2H), 4.84 (s, br, 1H), 5.44 (s, br, 1H), 6.67-6.73 (m, 1H), 6.77-6.86 (m, 1H), 6.98-7.04 (m, 1H), 7.05-7.13 (m, 1H), 7.55 (s, 2H).

Example 39

2,6-dichloro-N-[2-(2-hydroxyphenyl)ethyl]-4-(trifluoromethyl)benzenesulfonamide 2-(2-aminoethyl)phenol (53 mg, 0.39 mmol) was dissolved in DCM (2 mL) and TMS-Cl (50 μL, 0.40 mmol) was added followed by triethylamine (100 μL, 0.73 mmol). The reaction mixture became clear and was stirred for 20 minutes before 2,6-dichloro-4-(trifluoromethyl)benzenesulfonyl chloride (72 mg, 0.23 mmol) was added. The reaction mixture was stirred for 2 hours and 1 drop of water was added and the reaction mixture was concentrated. DCM (2 mL) was added to the residue followed by 3 drops of 3N HCl followed by addition of water (1 mL). The mixture was stirred for 5 minutes and then was extracted with DCM (2×1 mL). The combined organics were dried ($MgSO_4$) and concentrated. The crude product was purified by column chromatography on silica gel with DCM/MeOH (100:0 to 95:5) as the eluent. Yield 20.5 mg (21%). MS ESI$^+$ m/z 431 $[M+17]^+$. 1H NMR ($CDCl_3$) ppm 2.85 (t, J=6.64, 2H), 3.41 (t, J=6.64, 2H), 6.64-6.69 (m, 1H), 6.76-6.82 (m, 1H), 6.98-7.02 (m, 1H), 7.03-7.09 (m, 1H), 7.61 (s, 2H).

Example 40

2,6-dichloro-N-[2-(2-hydroxyphenyl)ethyl]benzenesulfonamide 2-(2-aminoethyl)phenol (53 mg, 0.39 mmol) was dissolved in DCM (2 mL) and TMS-Cl (50 μL, 0.40 mmol) was added followed by triethylamine (100 μL, 0.73 mmol). The reaction mixture became clear and was stirred for 20 minutes before 2,6-dichlorobenzenesulfonyl chloride (56 mg, 0.23 mmol) was added. The reaction mixture was stirred for 2 hours before 1 drop of water was added and the reaction mixture was concentrated. DCM (2 mL) was added to the residue followed by 3 drops of 3N HCl followed by addition of water (1 mL). The mixture was stirred for 5 minutes and then was extracted with DCM (2×1 mL). The combined organics were dried ($MgSO_4$) and concentrated. The crude product was purified by column chromatography on silica gel with petroleum ether/Ethylacetate (100:0 to 50:50) as the eluent. Yield 12 mg (15%). MS ESI$^+$ m/z 346 $[M+H]^+$.

Example 41

2,4-dichloro-6-hydroxy-N-[2-(2-hydroxyphenyl)ethyl]benzenesulfonamide 2-(2-Aminoethyl)phenol (90 mg, 0.66 mmol) was dissolved in dry DCM (3 mL) and TMS-Cl (83 μL, 0.66 mmol)

was added followed by triethylamine (136 µL, 1.16 mmol). The reaction mixture was stirred for 30 minutes at room temperature before 2,4-dichloro-6-hydroxy-benzenesulfonyl chloride (101 mg, 0.386 mmol was added. The reaction mixture was stirred for 1 hour before 2N HCl(aq) was added. The reaction mixture was concentrated and purified by preparative HPLC (XBridge C18 column, 10-60% acetonitrile in $NH_4CO_3/NH_3$ buffer) to give 72 mg, (51%) of a light yellow solid. MS ESI$^+$ m/z 362 [M+H]$^+$ $^1$H NMR (CDCl$_3$) 2.86 (t, 2H), 3.27 (q, 2H), 5.00 (br s, 1H), 5.53 (br t, 1H), 6.71 (d, 1H), 6.86 (dt, 1H), 6.94 (d, 1H), 6.98 (d, 1H), 7.04 (dd, 1H), 7.12 (dt, 1H), 10.08 (s, 1H)

Example 42

2,4-dichloro-6-hydroxy-N-[2-(o-tolyl)ethyl]benzenesulfonamide 2-(o-tolyl)ethanamine (31 mg, 0.23 mmol) was dissolved in dry DCM (2 mL) followed by addition of triethylamine (45 µL, 0.38 mmol) and 2,4-dichloro-6-hydroxy-benzenesulfonyl chloride. The reaction mixture was stirred for 30 minutes at room temperature before 2,4-dichloro-6-hydroxy-benzenesulfonyl chloride (50 mg, 0.19 mmol was added. The reaction mixture was stirred for 1 hour and concentrated. The residue was dissolved in acetonitrile and purified by preparative HPLC (XBridge C18 column, 10-70% acetonitrile in $NH_4CO_3$ $NH_3$ buffer). The product obtained was dissolved in dichloromethane and filtered to remove the residual $NH_4CO_3$ from the buffer before it was concentrated. The colorless oil was dissolved in water and freeze dried to give a white solid. Yield 24 mg (35%). MS ESI$^+$ m/z 360 [M+H]$^+$ $^1$H NMR (CDCl$_3$) 2.25 (s, 3H), 2.86 (t, 2H), 3.20 (q, 2H), 6.99 (q, 2H), 7.06 (m, 1H), 7.15 (m, 3H), 10.07 (s, 1H)

Example 43

4-chloro-3-hydroxy-N-[2-(2-hydroxyphenyl)ethyl]benzenesulfonamide 2-(2-Aminoethyl)phenol (51.4 mg, 0.37 mmol) was dissolved in dry DCM (2 mL) and TMS-Cl (48 µL, 0.37 mmol) was added followed by triethylamine (78 µL, 0.66 mmol). The reaction mixture was stirred for 30 minutes at room temperature before 4-chloro-3-hydroxy-benzenesulfonyl chloride (50 mg, 0.22 mmol was added. The reaction mixture was stirred for 1 hour before 2N HCl (aq) was added and the reaction mixture was concentrated. The residue was dissolved in acetonitrile-water and purified by preparative HPLC (XBridge C18 column, 10-60% acetonitrile in $NH_4CO_3/NH_3$ buffer) to give 22 mg (31%) of the product. MS ESI$^+$ m/z 328 [M+H]$^+$ $^1$H NMR (CDCl$_3$) 2.80 (t, 2H), 3.25 (q, 2H), 5.11 (br s, 1H), 6.19 (br s, 1H), 6.73 (dd, 1H), 6.81 (dt, 1H), 6.97 (dd, 1H), 7.08 (dt, 1H), 7.25 (dd, 1H), 7.36 (d, 1H), 7.40 (d, 1H).

Example 44

6-chloro-3-hydroxy-N-[2-(2-hydroxyphenyl)ethyl]-2,4-dimethyl-benzenesulfonamide 2-(2-Aminoethyl)phenol (47 mg, 0.34 mmol) was dissolved in dry DCM (2 mL) and TMS-Cl (43 µL, 0.34 mmol) was added followed by triethylamine (71 µL, 0.60 mmol) The reaction mixture was stirred for 30 minutes at room temperature before 6-chloro-3-hydroxy-2,4-dimethyl-benzenesulfonyl chloride (51.0 mg, 0.20 mmol) was added and the mixture was stirred for an additional 1 h. After the reaction was complete, 4N HCl in dioxane was added and the mixture was stirred for 15 minutes. The reaction mixture was concentrated, and the residue was dissolved in acetonitrile-water and purified by preparative HPLC (XBridge C18 column, 10-70% acetonitrile in $NH_4CO_3/NH_3$ buffer) to obtain 29 mg (41%) of the title product as a white solid. MS ESI$^+$ m/z 356 [M+H]$^+$ $^1$H NMR (CDCl$_3$) 2.25 (s, 3H), 2.60 (s, 3H), 2.83 (t, 2H), 3.19 (q, 2H), 5.05 (br s, 1H), 5.56 (t, 1H), 6.74 (dd, 1H), 6.83 (dt, 1H), 7.02 (dd, 1H), 7.10 (m, 2H).

Example 45

3,5-dichloro-2-[2-(o-tolyl)ethylsulfamoyl]benzoic acid 2-(o-tolyl)ethanamine (26.5 mg, 0.196 mmol) was dissolved in dry DCM (2 mL) followed by addition of triethylamine (39 µL, 0.34 mmol) and methyl 3,5-dichloro-2-chlorosulfonyl-benzoate (51.0 mg, 0.168 mol). The reaction mixture was stirred for 2.5 hours at room temperature and concentrated. The residue was dissolved in acetonitrile and purified by preparative HPLC (XBridge C18 column, 20-80% acetonitrile in $NH_4CO_3/NH_3$ buffer). The product obtained was dissolved in dichloromethane, filtered to remove residual $NH_4CO_3$ from the buffer and concentrated. The residue was dissolved in water and freeze dried to obtain the product as a white solid (26 mg, 40% yield). MS ESI$^+$ m/z 388 [M+H]$^+$ $^1$H NMR (CDCl$_3$) 2.44 (s, 3H), 3.15 (t, 2H), 3.92 (t, 2H), 7.18 (m, 4H), 7.77 (d, 1H), 7.90 (d, 1H).

Example 46

N-[2-(2-chlorophenyl)ethyl]-4-methoxy-2,6-dimethyl-benzenesulfonamide 4-methoxy-2,6-dimethyl-benzenesulfonyl chloride (100 mg, 0.426 mmol) was dissolved in DCM (2 mL) and 2-(2-chlorophenyl)ethanamine (66.3 mg, 0.426 mol) was added followed by triethylamine (131 µL, 0.94 mmol). The reaction mixture was stirred for 3 hours, diluted with water and extracted with DCM (2×10 mL). The combined organics were dried over (MgSO$_4$) and concentrated. The crude product was purified by column chromatography on silica gel with DCM/MeOH (100:0 to 97.5:2.5) to afford the title compound as a colorless oil. Yield 95 mg (63%). MS m/z 354 [M+H]$^+$. HPLC purity 95%. 1H-NMR (400 MHz, CDCl$_3$): ppm 2.58 (s, 6H), 2.89 (t, J=7.0 Hz, 2H), 3.16-3.21 (m, 2H), 3.81 (s, 3H), 4.40-4.46 (m, 1H), 6.61 (s, 2H), 7.10-7.19 (m, 3H), 7.26-7.33 (m, 1H).

Example 47

N-[2-(2-hydroxyphenyl)ethyl]-4-methoxy-2,6-dimethyl-benzenesulfonamide 4-methoxy-2,6-dimethyl-benzenesulfonyl chloride (100 mg, 0.426 mmol) was dissolved in DCM (4 mL) and TMS-Cl (0.0919 mL, 0.724 mmol) was added followed by triethylamine (150 µL g, 0.128 mol). The reaction was stirred for 10 minutes before 4-methoxy-2,6-dimethyl-benzenesulfonyl chloride (100 mg, 0.426 mol) was added. The reaction mixture was stirred for 1 hour before 0.25N HCl (4 mL) was added and the mixture was stirred for 10 minutes. The reaction mixture was extracted with DCM (2×10 mL)

and the combined organics were dried (MgSO$_4$) and concentrated to give a colorless oil. The crude product was purified by column chromatography on silica gel with DCM/MeOH (100:0 to 97.5:2.5) to afford the title compound. Yield 40 mg (28%). MS m/z 336 [M+H]$^+$. 1H NMR (400 MHz, CDCl$_3$) ppm 2.56 (s, 6H), 2.79 (t, J=6.44 Hz, 2H), 3.12-3.17 (m, 2H), 3.80 (s, 3H), 4.84-4.90 (m, 1H), 5.70 (bs, 1H), 6.60 (s, 2H), 6.74-6.80 (m, 2H), 6.95-7.00 (m, 1H), 7.06-7.10 (m, 1H).

Example 48

4-hydroxy-N-[2-(2-hydroxyphenyl)ethyl]-2,6-dimethyl-benzenesulfonamide

N-[2-(2-hydroxyphenyl)ethyl]-4-methoxy-2,6-dimethyl-benzenesulfonamide (35.0 mg, 0.104 mmol) was dissolved in DCM (300 μL) and a 1N solution of BBr$_3$ (300 μL, 0.3 mmol) was added. The reaction mixture was stirred for 3 hours before water was added. An emulsion formed. The mixture was diluted with DCM and water. The aqueous phase was extracted with DCM (11×). The combined organics were dried (MgSO$_4$) and concentrated. The crude product was purified by preparative HPLC (ACE C18 19×50 mm); 0.1% TFA in water/MeCN; 90:10 to 30:70 to give 2.0 mg (6%) of a white solid. MS ESI$^+$ m/z 322 [M+H]$^+$. HPLC purity>95%.

The structural formulas of Examples 1-48 are shown in Table 1.

TABLE 1

| Example | Structural formula | Chemical name |
|---|---|---|
| 1 | | N-[2-(2-methoxyphenyl)ethyl]-2,4,6-trimethylbenzene-1-sulfonamide |
| 2 | | N-[2-(2-fluorophenyl)ethyl]-2,4,6-trimethylbenzene-1-sulfonamide |
| 3 | | N-[2-(2-fluorophenyl)ethyl]-2,2,4,6,7-pentamethyl-2,3-dihydro-1-benzofuran-5-sulfonamide |
| 4 | | 4-bromo-2,6-dichloro-N-[2-(2-methoxyphenyl)ethyl]benzene-1-sulfonamide |
| 5 | | 4-bromo-2,6-dichloro-N-[2-(2-fluorophenyl)ethyl]benzene-1-sulfonamide |
| 6 | | N-[2-(2-chlorophenyl)ethyl]-2,4,6-trimethylbenzene-1-sulfonamide |

TABLE 1-continued

| Example | Structural formula | Chemical name |
|---|---|---|
| 7 | 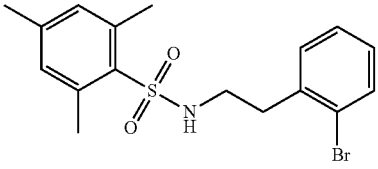 [SMILES: Cc1cc(C)c(S(=O)(=O)NCCc2ccccc2Br)c(C)c1] | N-[2-(2-bromophenyl)ethyl]-2,4,6-trimethylbenzene-1-sulfonamide |
| 8 | 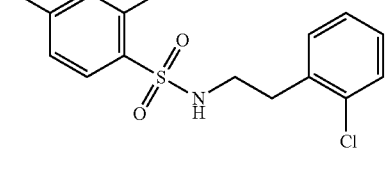 | 4-bromo-2-chloro-N-[2-(2-chlorophenyl)ethyl]benzene-1-sulfonamide |
| 9 | 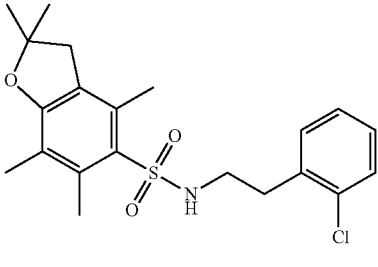 [SMILES: Cc1c(C)c(S(=O)(=O)NCCc2ccccc2Cl)c(C)c2c1OC(C)(C)C2] | N-[2-(2-chlorophenyl)ethyl]-2,2,4,6,7-pentamethyl-2,3-dihydro-1-benzofuran-5-sulfonamide |
| 10 | 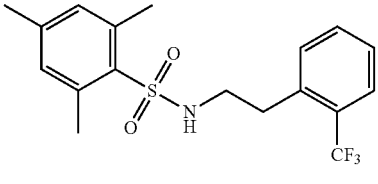 [SMILES: Cc1cc(C)c(S(=O)(=O)NCCc2ccccc2C(F)(F)F)c(C)c1] | 2,4,6-trimethyl-N-{2-[2-(trifluoromethyl)phenyl]ethyl}benzene-1-sulfonamide |
| 11 | 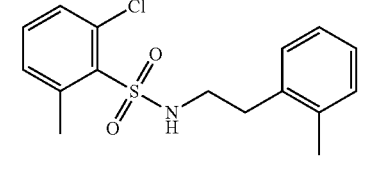 [SMILES: Cc1ccccc1CCNS(=O)(=O)c1c(C)cccc1Cl] | 2-chloro-6-methyl-N-[2-(2-methylphenyl)ethyl]benzene-1-sulfonamide |
| 12 | 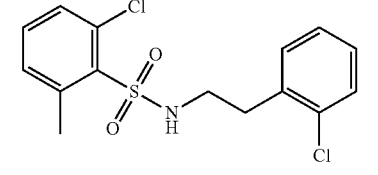 [SMILES: Cc1cccc(Cl)c1S(=O)(=O)NCCc1ccccc1Cl] | 2-chloro-N-[2-(2-chlorophenyl)ethyl]-6-methylbenzene-1-sulfonamide |
| 13 | 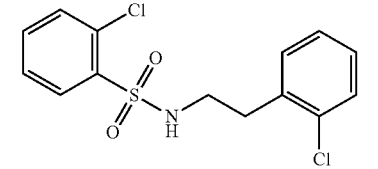 [SMILES: O=S(=O)(NCCc1ccccc1Cl)c1ccccc1Cl] | 2-chloro-N-[2-(2-chlorophenyl)ethyl]benzene-1-sulfonamide |
| 14 | 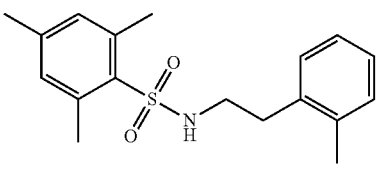 [SMILES: Cc1cc(C)c(S(=O)(=O)NCCc2ccccc2C)c(C)c1] | 2,4,6-trimethyl-N-[2-(2-methylphenyl)ethyl]benzene-1-sulfonamide |

TABLE 1-continued

| Example | Structural formula | Chemical name |
|---|---|---|
| 15 | | 2,4,6-trimethyl-N-{2-[2-(trifluoromethoxy)phenyl]ethyl}benzene-1-sulfonamide |
| 16 | | 2-chloro-6-methyl-N-{2-[2-(trifluoromethyl)phenyl]ethyl}benzene-1-sulfonamide |
| 17 | | 4-bromo-2,6-dichloro-N-[2-(2-methylphenyl)ethyl]benzene-1-sulfonamide |
| 18 | | 2,4-dichloro-N-[2-(2-methylphenyl)ethyl]benzene-1-sulfonamide |
| 19 | | 4-bromo-2,6-dichloro-N-{2-[2-(trifluoromethyl)phenyl]ethyl}benzene-1-sulfonamide |
| 20 | | 4-bromo-2,6-dichloro-N-[2-(2-chlorophenyl)ethyl]benzene-1-sulfonamide |
| 21 | | 2,6-dichloro-N-[2-(2-fluorophenyl)ethyl]benzene-1-sulfonamide |
| 22 | | 2,6-dichloro-N-{2-[2-(trifluoromethyl)phenyl]ethyl}benzene-1-sulfonamide |

TABLE 1-continued

| Example | Structural formula | Chemical name |
|---|---|---|
| 23 | | 2,6-dichloro-N-[2-(2-chlorophenyl)ethyl]benzene-1-sulfonamide |
| 24 | | 2,6-dichloro-N-[2-(2-fluorophenyl)ethyl]-4-(pyridin-3-yl)benzene-1-sulfonamide |
| 25 | | 2,6-dichloro-4-cyclopropyl-N-[2-(2-fluorophenyl)ethyl]benzene-1-sulfonamide |
| 26 | | 2,6-dichloro-N-[2-(2-chlorophenyl)ethyl]-4-cyclopropylbenzene-1-sulfonamide |
| 27 | | 2,6-dichloro-N-[2-(2-chlorophenyl)ethyl]-4-(trifluoromethyl)benzene-1-sulfonamide |
| 28 | | N-[2,2-difluoro-2-(2-methylphenyl)ethyl]-2,4,6-trimethylbenzene-1-sulfonamide |
| 29 | | 4-bromo-2,6-dichloro-N-[2,2-difluoro-2-(2-methylphenyl)ethyl]benzene-1-sulfonamide |
| 30 | | N-[2-(2-chlorophenyl)-2,2-difluoroethyl]-2,4,6-trimethylbenzene-1-sulfonamide |

TABLE 1-continued

| Example | Structural formula | Chemical name |
|---|---|---|
| 31 | | 4-bromo-2,6-dichloro-N-[2-(2-chlorophenyl)-2,2-difluoroethyl]benzene-1-sulfonamide |
| 32 | | N-[2-(2-chlorophenyl)ethyl]-2,6-dimethyl-4-(propan-2-yl)benzene-1-sulfonamide |
| 33 | | 2,6-dimethyl-N-[2-(2-methylphenyl)ethyl]-4-(propan-2-yl)benzene-1-sulfonamide |
| 34 | | N-[2-fluoro-2-(2-methylphenyl)ethyl]-2,4,6-trimethylbenzene-1-sulfonamide |
| 35 | | 4-bromo-2,6-dichloro-N-[2-fluoro-2-(2-methylphenyl)ethyl]benzene-1-sulfonamide |
| 36 | | N-[2-fluoro-2-(2-methylphenyl)ethyl]-2,6-dimethyl-4-(propan-2-yl)benzene-1-sulfonamide |
| 37 | | N-[2-(2-hydroxyphenyl)ethyl]-2,4,6-trimethylbenzene-1-sulfonamide |
| 38 | | 4-bromo-2,6-dichloro-N-[2-(2-hydroxyphenyl)ethyl]benzenesulfonamide |

TABLE 1-continued

| Example | Structural formula | Chemical name |
|---|---|---|
| 39 | | 2,6-dichloro-N-[2-(2-hydroxyphenyl)ethyl]-4-(trifluoromethyl)benzenesulfonamide |
| 40 | | 2,6-dichloro-N-[2-(2-hydroxyphenyl)ethyl]benzenesulfonamide |
| 41 | | 2,4-dichloro-6-hydroxy-N-[2-(2-hydroxyphenyl)ethyl]benzenesulfonamide |
| 42 | | 2,4-dichloro-6-hydroxy-N-[2-(o-tolyl)ethyl]benzenesulfonamide |
| 43 | | 4-chloro-3-hydroxy-N-[2-(2-hydroxyphenyl)ethyl]benzenesulfonamide |
| 44 | | 6-chloro-3-hydroxy-N-[2-(2-hydroxyphenyl)ethyl]-2,4-dimethyl-benzenesulfonamide |
| 45 | | 3,5-dichloro-2-[2-(o-tolyl)ethylsulfamoyl]benzoic acid |
| 46 | | N-[2-(2-chlorophenyl)ethyl]-4-methoxy-2,6-dimethyl-benzenesulfonamide |

TABLE 1-continued

| Example | Structural formula | Chemical name |
|---|---|---|
| 47 | | N-[2-(2-hydroxyphenyl)ethyl]-4-methoxy-2,6-dimethyl-benzenesulfonamide |
| 48 | | 4-hydroxy-N-[2-(2-hydroxyphenyl)ethyl]-2,6-dimethyl-benzenesulfonamide |

Biological Assays

In Vitro Assays of Nox Inhibiting Activity

Materials

RPMI 1640 with Glutamax, DMEM/F12 (1:1), Hanks' buffered salt solution (HBSS), fetal bovine serum (FBS), and Amplex Red were purchased from Invitrogen, Paisley, UK. Pest (penicillin, streptomycin), neomycin, blasticidine, ionomycin, phorbol myristate acetate (PMA), diphenyleneiodonium chloride (DPI), dapsone, ML-171, Phox-I2, xanthine, hypoxanthine, xanthine oxidase, DMSO, DPPH (2,2-diphenyl-1-picrylhydrazyl), Tween® 20, sucrose, flavin adenine dinucleotide (FAD), phosphatidic acid, ethylene glycol-bis(β-aminoethyl ether)-N,N,N',N'-tetraacetic acid (EGTA), horseradish peroxidase (HRP) and NADPH were purchased from Sigma-Aldrich. Ficoll Paque Plus (GE Healthcare) GKT136901 (chemical name: 2-(2-Chlorophenyl)-4-methyl-5-(pyridin-2-ylmethyl)-1H-pyrazolo[4,3-c]pyridine-3,6-dione), a Nox1/Nox4 selective inhibitor, was a kind gift from prof. Harald H H Schmidt (Maastricht University, Netherlands).

Cell Culture

HEK293 overexpressing Nox4 (CJ Nox4) cells were purchased from Redoxis, Lund, Sweden. HEK 293 cells expressing Nox5, Nox3 (HEK TRex) and CHO cells expressing Nox1, were a kind gift from Vincent Jaque Center Medical Universitaire, Geneva, Switzerland. Nox2 expressed in isolated neutrophils were isolated from whole blood (human), as previously described (Anvari E, et al., Free Radic Res 2015; 49:1308-1318).

HEK293 cells (CJ Nox4) were cultured in RPMI 1640 with Glutamax supplemented with FBS (10%), penicillin (100 U/ml) and streptomycin (100 mg/ml) at 37° C. in air with 5% $CO_2$. Every third passage 200 □g/ml neomycin were supplied in growth medium as selective agent.

HEK293T cells expressing tetracycline-inducible human (Nox3 or Nox4) and HEK293 cells stably expressing human Nox5 were generated as described previously (Serrander et al., 2007a,b). HEK cells were cultured in Dulbecco's modified Eagle medium (DMEM) with 4.5 g/l glucose, supplemented with FBS (10%), penicillin (100 U/ml) and streptomycin (100 mg/ml) at 37° C. in air with 5% $CO_2$.

CHO cells expressing Nox1 were cultured in DMEM 12 medium (DMEM/F12) supplemented with FBS (10%), penicillin (100 U/ml) and streptomycin (100 µg/ml) at 37° C. in air with 5% $CO_2$.

ROS Measurement in Assays

Reactive oxygen produced in whole cells or in membrane preparation of Nox1, Nox3, Nox4, Nox5 and xanthine oxidase and glucose oxidase were determined using Amplex Red as detection probe of formed $H_2O_2$. Amplex Red (10-acetyl-3,7-dihydroxyphenoxazine) in combination with HRP and co-factors reacts with $H_2O_2$ in a 1:1 stoichiometry to form a highly fluorescent resorufin excitated at 544 nm producing emission at 590 nm.

DPPH Redox Assay

DPPH, a well-known sensitive chemical of monitoring reactions involving radicals described by Xiong Q, et al., Biol Pharm Bull 1996; 19:1580-1585, was used as control to exclude any redox active compound. DPPH was incubated with decreasing concentrations (200-0.003 µM) of compounds of the invention or prior art compound GKT136901 (as a positive control). The plate was kept in the dark for 60 min, after which the absorbance of the solution was measured at 518 nm.

Fluorescence Based Amplex Red Assays of Intact Nox Expressing HEK and CHO Cells

Adherent cells (CHO, HEK) were collected by trypsinization, centrifuged, washed with HBSS, counted, and resuspended in HBSS. Cells were seeded in 96-well black flat bottom plates at a density of 50,000-100,000 cells/well. All compounds were dissolved in DMSO and concentrations ranging from 0.003 to 200 µM were tested in Nox cellular assays with a final concentration of DMSO of 1%. Cells were incubated at 37° C. with the compounds for 30 minutes before measurement. Cells expressing Nox1 and Nox2 were activated with the PKC activator PMA (0.1 µM). Nox5 was activated with the Ca2+ ionophore ionomycin (1 µM) and further enforced with PMA. The CJ HEK 293 cells overexpressed Nox4 constitutively. In the HTS screen HEK 293 TRex was used and tetracycline (1 mg/ml) was added 18 h before measurement to induce Nox4 expression. Production of hydrogen peroxide by Nox in intact cells was measured using Amplex Red fluorescence as described by Jaquet V, et al., Br J Pharmacol 2011; 164:507-520. Assay reagents including HRP (0.1 mM) and Amplex Red (50 µM) were added to initiate production of hydrogen peroxide. Fluorescence was read in a fluorescence plate reader at 37° C. every minute between 30-60 minutes.

Membrane Preparation

Membranes from transfected cells overexpressing Nox1 (CHO), Nox2 (PLB), Nox3 (HEK), Nox4 (HEK) or Nox5 (HEK) were prepared as described in Pailcz et al., 2001, J. Biol. Chem, 76, 3090-3097. Cells were suspended and homogenized in sonication buffer containing PBS, sucrose (11%), NaCl (120 mM) and EGTA (1 mM) supplemented with protease inhibitors and further processed and then broken by sonication cooled with an ice bath. Then the sample was centrifuged at 200×g for 10 min. Supernatant was carefully added on top of a 17/40% discontinuous sucrose gradient and centrifuged at 150 000×g for 60 min. Membranes containing Nox isoforms were collected at the 17/40% sucrose interface as described by Jaquet V, et al., Br J Pharmacol 2011; 164:507-520. For the Nox isoforms Nox1, Nox2, Nox3 a subunit-specific cell-free, membrane-based system has been developed and recombinant proteins of the subunits were added to receive activation of the Nox-iso forms in the cell-free assay. The Amplex Red assay was performed in black 96-well flat bottom plates. Assay reagents including HRP (0.1 mM), FAD (6 µM), phosphatidic acid (15 µM) and Amplex Red (50 µM) were added followed by NADPH (30 µM) to initiate production of hydrogen peroxide. The production of hydrogen peroxide was followed by use of a fluorescence plate reader, read at 37° C. every minute between 30-60 minutes.

Determination of $IC_{50}$ for Nox2 Inhibition in Human Neutrophils Using Isoluminol-Dependent Chemiluminescence Compounds of the invention were tested for selectivity against Nox2 in isolated neutrophils from whole blood (human), as previously described (Anvari E, et al., vide supra). Levels of ROS from PMA stimulated primary human neutrophils were measured using isoluminol-dependent chemiluminescence. Isoluminol is a hydrophobic dye unable to pass biological membranes, hence extracellular ROS can be determined. The dye is excited by ROS and the light emitted when the excited molecules return to the ground state, relative to the amount of released ROS, is measured. This reaction is catalyzed and amplified by peroxidases. Naturally occurring peroxidase can achieve this, however secretion of endogenous peroxidases is limited and hence additional peroxidase in the form of HRP needs to be added. Compounds of the invention and GKT136901 were diluted at 4× working concentration and titrated from 100 µM to 0.006 µM in 1:4 steps as final concentrations. DPI was diluted in isoluminol buffer at 4× working concentration titrated from 10 µM to 0.0006 µM as final concentrations. PMA was diluted in isoluminol buffer at 4× working concentration for a final concentration of 30 ng/ml. Compounds and DPI had a final DMSO concentration of 1% in the wells and DMSO of 1% also in the control. Luminescence was detected using FluoStar Optima (BMG, Labtech). The isoluminol buffer was prepared immediately prior to addition to test plate. The buffer contained HRP fraction with or without PMA (30 ng/ml). Stock solutions at 6 µg/ml (PMA in HBSS), 3 µg/ml (PMA in DMSO) and 24 mM (DPI) were used and further diluted at the day of analysis to 4× working concentrations in HBSS with or without DMSO.

Amplex Red Xanthine Oxidase (XO) Assay

The assay was designed for Amplex Red analysis of production of hydrogen peroxide. Test compounds were incubated with 5 mU/ml bovine derived xanthine oxidase for 15 min at room temperature followed by the addition of substrate and detection mix (final concentrations of 0.2 U/ml HRP, 5 µM hypoxanthine, and 50 µM Amplex Red). As described by Hirano K et al., Antioxid Redox Signal 2015 10; 23:358-374, production of hydrogen peroxide was followed by fluorescence detection during 30 min at 37° C. in a plate reader that use excitation at 544 nm producing emission at 590 nm.

Amplex Red and Glucose Oxidase (GO) Assay

The assay was performed using a modified form of Invitrogen Amplex™ Red Glucose/Glucose Oxidase Assay Kit Cat no: A22189. Test compounds were incubated with 5 mU/ml glucose oxidase for 30 min at room temperature, followed by the addition of substrate and detection mix (final concentrations of 0.1 U/ml HRP, 10 mM glucose, 50 µM Amplex Red in phosphate buffer pH 7.4) and then fluorescence detection of hydrogen peroxide production was performed during 30 min at 37° C. in a plate reader that use excitation at 544 nm producing emission at 590 nm.

Results of above described biological assays are shown in Tables 2 and 3.

TABLE 2

| Biological effect | Ex. 11 | Ex. 17 | Ex. 26 |
|---|---|---|---|
| $IC_{50}$ on hNox4 in recombinant cells | 2.4 µM | 0.27 µM | 0.36 µM |
| Ki on hNox4 in membrane assay | 4.4 µM | 0.56 µM | 2.2 µM |
| Activity on Nox1, Nox2, Nox3 and Nox5 | inactive | inactive | inactive |
| Inhibition of oxygen consumption in Nox4 expressing HEK293 cells | yes | yes | yes |
| Inhibition of oxygen consumption in Nox1 expressing CHO cells | No | No | No |

TABLE 3

$IC_{50}$ (µM) of compounds of the invention and of prior art compound GKT136901

| Ex. | Nox4 | Nox1 | Nox2 | Nox3 | Nox5 | XO | DPPH | GO |
|---|---|---|---|---|---|---|---|---|
| 2 | 2.2 | — | — | n.a. | — | — | — | n.a. |
| 6 | 0.27 | — | — | n.a. | — | — | — | n.a. |
| 7 | 0.27 | — | — | n.a. | — | — | — | n.a. |
| 9 | 1.6 | — | — | n.a. | — | — | — | n.a. |
| 11 | 2.4 | — | — | — | — | — | — | — |
| 14 | 0.09 | — | — | n.a. | — | — | — | n.a. |
| 17 | 0.27 | — | — | — | — | — | — | — |
| 20 | 0.9 | — | — | n.a. | — | — | — | n.a. |
| 25 | 1.1 | — | n.a. | n.a. | — | — | — | n.a. |
| 26 | 0.36 | — | — | — | — | — | — | — |
| 27 | 1.6 | — | n.a. | n.a. | — | — | — | n.a. |
| 35 | 1.7 | — | — | n.a. | — | — | — | n.a. |
| 35 (isomer 1) | 1.7 | — | — | n.a. | — | — | — | n.a. |
| 35 (isomer 2) | 4.9 | — | — | n.a. | — | — | — | n.a. |
| 37 | 0.8 | — | 0.9 | n.a. | — | — | — | n.a. |
| 38 | 0.3 | — | 1.5 | n.a. | — | — | — | n.a. |
| 44 | 2.4 | — | 0.9 | n.a. | — | — | — | n.a. |
| 46 | 0.3 | — | — | n.a. | — | — | — | n.a. |
| 47 | 1.6 | — | 1.0 | n.a. | — | — | — | n.a. |
| 48 | 22 | — | 0.87 | n.a. | — | — | — | n.a. |
| GKT136901 | 1.6 | 0.5 | 9 | n.a. | 66-22 | n.a. | active | n.a. |

The sign "—" stands for "inactive"; "n.a." stands for "not analyzed".

Ischemic Stroke and Nox4—In Vitro Model

Compounds of the invention (Examples 11, 17 and 44) have demonstrated neuroprotective effect, using two different in vitro stroke models. Hippocampal brain slices and human brain micro-vascular endothelial cells were subjected to hypoxia and glucose deprivation (starvation) for 5 hours and were tested for viability after 24 hours of culture in the presence of Example 11 or Example 17 at different concentrations. Additionally, human brain micro-vascular endothelial cells were subjected to hypoxia and glucose deprivation (starvation) for 6 hours and were tested for viability after 24 hours of culture in the presence of Example 44 at various concentrations. The results are shown in FIGS. 1-5.

In Vivo Model of Acute Ischemic Stroke

A mouse model of acute ischemic stroke by transient middle cerebral artery occlusion (tMCAO) was used. The model has been described by Kleinschnitz C, et al. 2010, J Exp Med 203(3):513-518. C57B16/J mice were anesthetized with isoflurane (0.8% in oxygen). The animal was placed on a heating-pad, and rectal temperature was maintained at 37.0° C. using a servo-controlled rectal probe-heating pad (Cibertec, Spain). Transient cerebral ischemia was induced using an intraluminal filament technique. Using a surgical microscope (Tecnoscopio OPMI pico, Carl Zeiss, Meditec Iberia SA, Spain), a midline neck incision was made and the right common and external carotid arteries were isolated and permanently ligated. A microvascular temporary ligature was placed on the internal carotid artery to non-permanently cut the blood flow. A silicon rubber-coated monofilament (6023910PK10, Doccol Corporation, Sharon, Mass., USA) was inserted through a small incision into the common carotid artery and advanced into the internal carotid artery until a resistance was felt. The tip of the monofilament was precisely located at the origin of the right middle cerebral artery so as to interrupt blood flow. The filament was held in place by a tourniquet suture in the common carotid artery to prevent filament relocation during the ischemia period. Animals were maintained under anaesthesia during 1 h occlusion followed by the reperfusion period that started when the mono filament was removed. After the surgery, wounds were carefully sutured and animals were allowed to recover from surgery in a temperature-controlled cupboard. Operation time per animal did not exceed 15 minutes. Animals were excluded from the stroke analysis, if they died within the first 24 h period, or if an intracerebral haemorrhage occurred.

Example 17 was dissolved in a mixture of DMSO/Cremophor/saline. Either Example 17 (2.56 mg/kg), or vehicle (DMSO/Cremophor/saline) was administered by intraperitoneal (ip) injection either 1 hour after reperfusion or 30 min before the removal of the filament. Injection was performed in total 6 times, once per hour, and the mice were sacrificed after 24 h.

Figure 6:
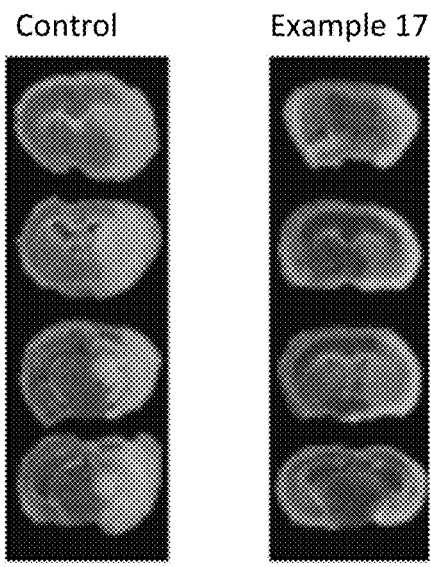
FIG. 6 shows coronal brain section slices from C57Bl6/J mice that had been exposed to middle cerebral artery occlusion for 1 h. The slices have been stained with 2,3,5-triphenyl tetrazolium chloride (TTC) to visualize the ischemic lesions. Control=mice having received vehicle only, and sacrificed after 24 hours; Example 17=mice having received Example 17 at a dosage of 2.56 mg/kg body weight, administered by one ip injection per hour, from 1 hour after reperfusion until 6 hours after reperfusion, and sacrificed after 24 hours.
Figure 7:
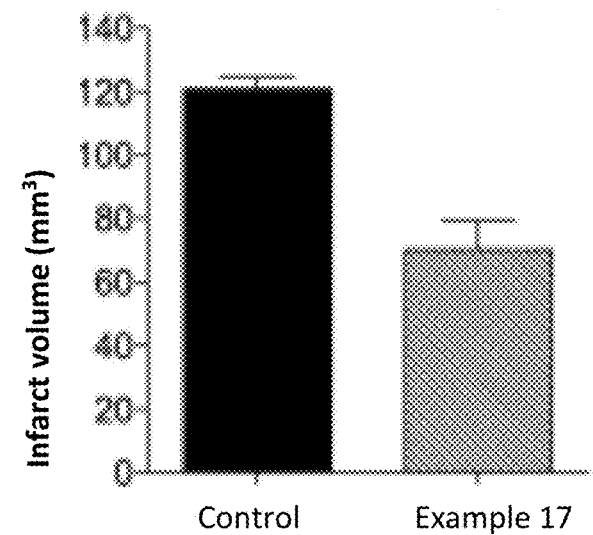
FIG. 7 is a bar chart showing the mean infarct volume (in $mm^3$) in mice in a model of acute stroke. Control=mice having received vehicle only. Example 17=mice having received Example 17 at a dosage of 2.56 mg/kg body weight, administered by one ip injection per hour, from 1 hour after reperfusion until 6 hours after reperfusion. The mice were sacrificed after 24 hours.
Figure 8:
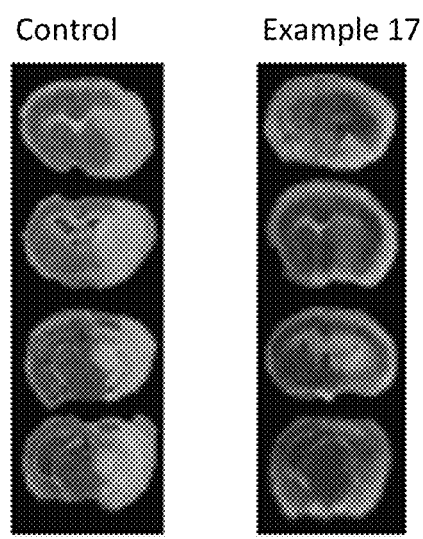
FIG. 8 shows coronal brain section slices from C57Bl6/J mice that had been exposed to middle cerebral artery occlusion for 1 h. Control=mice having received vehicle only, and sacrificed after 24 hours; Example 17=mice having received Example 17 at a dosage of 2.56 mg/kg body weight, administered by one ip injection per hour, from 30 minutes before reperfusion until 4.5 hours, and sacrificed after 24 hours.
Figure 9:
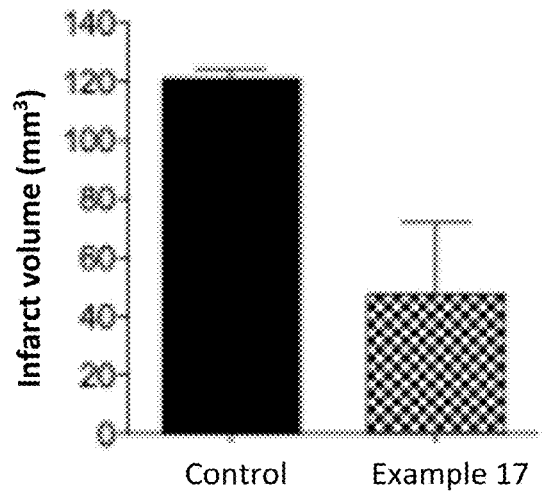
FIG. 9 is a bar chart showing the mean infarct volume (in $mm^3$) in mice in a model of acute ischemic stroke. Control=mice having received only vehicle. Example 17=mice having received Example 17 at a dosage of 2.56 mg/kg body weight, administered by one ip injection per hour, from 30 minutes before reperfusion until 4.5 hours after reperfusion. The mice were sacrificed after 24 hours.

After sacrificing the mice (24 h reperfusion), brains were quickly removed and cut in four 2-mm thick coronal sections using a mouse brain slice matrix (Harvard Apparatus, Spain). The slices were stained for 15 min at room temperature with 2% 2,3,5-triphenyltetrazolium chloride (TTC; Sigma-Aldrich, The Netherlands) in PBS to visualize the infarctions (FIGS. 6 and 8). Indirect infarct volumes were calculated by volumetry (ImageJ software, National Institutes of Health, USA) according to the following equation: $V_{indirect}$ (mm$^3$)=$V_{infarct}\times(1-(V_{ih}-V_{ch})/V_{ch})$, where the term ($V_{ih}-V_{ch}$) represents the volume difference between the ischemic hemisphere and the control hemisphere and ($V_{ih}-V_{ch}$)/$V_{ch}$ expresses this difference as a percentage of the control hemisphere (FIGS. 7 and 9).

As may be seen from FIGS. 6 and 8, the control animals suffer from large areas of neuronal cell death, shown by the white areas in the images. The mice that were treated by Example 17 had significant reduction in brain damage, as shown by the significantly reduced area of white, demonstrating the protective effect of the highly selective Nox4 inhibitor. FIGS. 7 and 9 show a substantial reduction of infarct volume in animals treated by Example 17, compared to control animals.

In Vitro Models of Alzheimer (Tauopathy)

Figure 10:
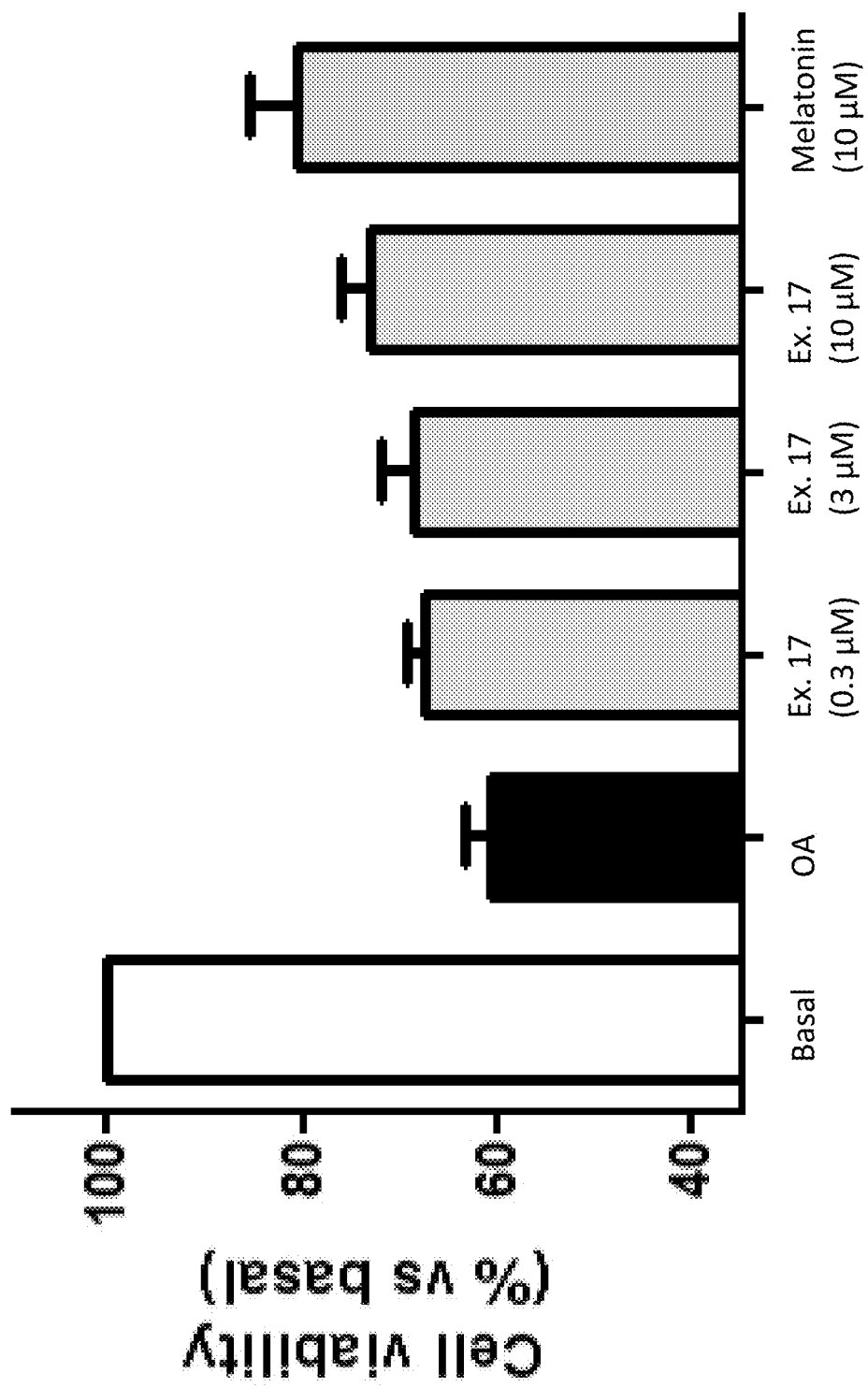
FIG. 10 is a bar chart showing cell viability (in % of basal cell viability) of cultured human neuroblastoma SHSY-5Y cells exposed to okadaic acid, in the absence or presence of different concentrations of Example 17 or melatonin as a positive control. Basal=Cells cultivated in the presence of culture medium only; OA=cells cultured in the presence of okadaic acid at a concentration of 15 nM; Ex. 17 (0.3 µM)=cells cultured in the presence of okadaic acid (15 nM) and Ex. 17 at a concentration of 0.3 µM; Ex. 17 (3 µM)=cells cultured in the presence of okadaic acid (15 nM) and Ex. 17 at a concentration of 3 µM; Ex. 17 (10 µM)=cells cultured in the presence of okadaic acid (15 nM) and Ex. 17 at a concentration of 10 µM; Melatonin (10 µM)=cells cultured in the presence of okadaic acid (15 nM) and melatonin at a concentration of 10 µM.

Tauopathy belongs to a class of neurodegenerative diseases associated with the pathological aggregation of tau protein in neurofibrillary or gliofibrillary tangles in the human brain. Tangles are formed of a microtubule-associated protein known as tau, causing it to aggregate in an insoluble form. In an in vitro model cultured human neuroblastoma SHSY-5Y cells were exposed to okadaic acid (15 nM), in the absence or presence of different concentrations (0.3 µM, 3 µM, or 10 µM) of Example 17, or in the presence of melatonin (10 µM) as a positive control (FIG. 10).

Figure 11:
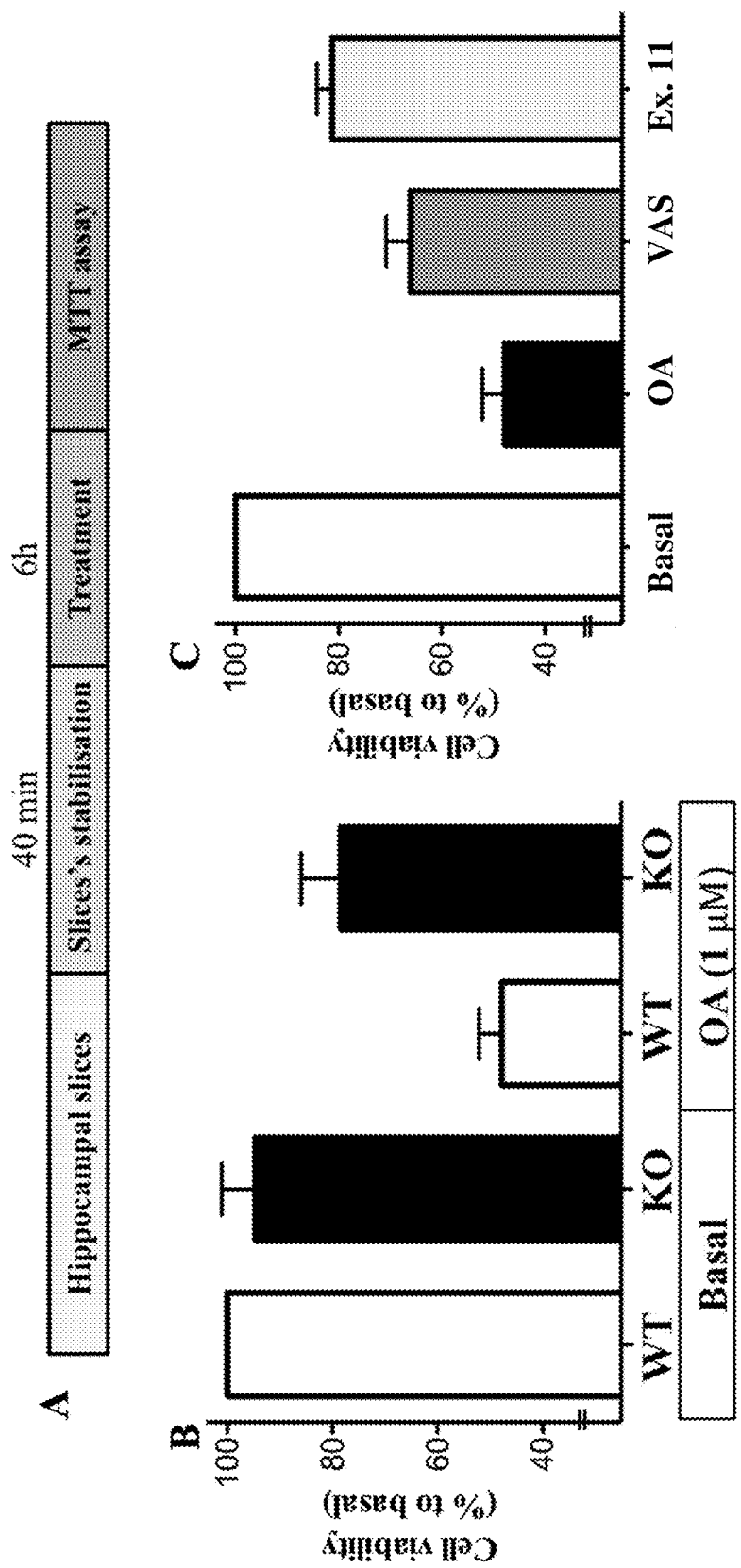
FIG. 11A represents time schedule for the treatment of hippocampal slices (Nox4 knockout or wildtype), including 40 minutes of stabilization, followed by 6 hours of treatment with okadaic acid (1 µM), or with okadaic acid (1 µM) in the presence of either the Nox inhibitor VAS2870 (3-benzyl-7-(2-benzoxazolyl)thio-1,2,3-triazolo[4,5-d]pyrimidine) (10 µM) or Example 11 (10 µM).
FIG. 11B is a bar chart representing cell viability (in % of the viability of hippocampal slices cultured only in culture medium) of Nox4 knockout (KO) or wildtype (WT) hippocampal cells, respectively. Basal=hippocampal slices cultured only in culture medium; OA1 (1 µM)=hippocampal slices cultured in the presence of okadaic acid (1 µM).
FIG. 11C is a bar chart representing cell viability (in % of the viability of hippocampal slices cultured only in culture medium) of wildtype hippocampal cells cultured in only culture medium (Basal); in the presence of okadaic acid at a concentration of 1 µM (OA); in the presence of okadaic acid (1 µM) and VAS2870 at a concentration of 10 µM (VAS) and in the presence of okadaic acid (1 µM) and Example 11 at a concentration of 10 µM (Ex. 11).

In a further experiment, mice hippocampal slices treated were treated with okadaic acid. The animals were either wildtype (WT) or Nox4 knockout (KO) mice. The slices were stabilized for 40 minutes in culture medium and treated for 6 hours with okadaic acid (1 µM), in the absence or presence of Example 11 (10 µM). The Nox inhibitor VAS2870 (3-benzyl-7-(2-benzoxazolyl)thio-1,2,3-triazolo[4,5-d]pyrimidine) was used as a positive control. Cell viability was determined by MTT assay. The results are illustrated in FIG. 11.

Effects on Human Islet Cell Viability

Human islet cells were incubated at control condition, with the cytokines IL-1β (20 ng/ml)+IFN-γ (20 ng/ml), or with palmitate (1.5 mM+2% BSA)+high glucose (20 mM) (PH) for 2 days with or without Nox1 inhibitor ML-171 (2 µM), Nox2 inhibitor Phos-I2 (2 µM) or Example 17 (1 µM). Islets were photographed in an inverted fluorescence microscope and the intensities of red (PI) and blue (Bisbenzimide) signals were quantified using Image J software. Results are indicated as mean±S.E.M for 7 human islet donors.

Figure 12:
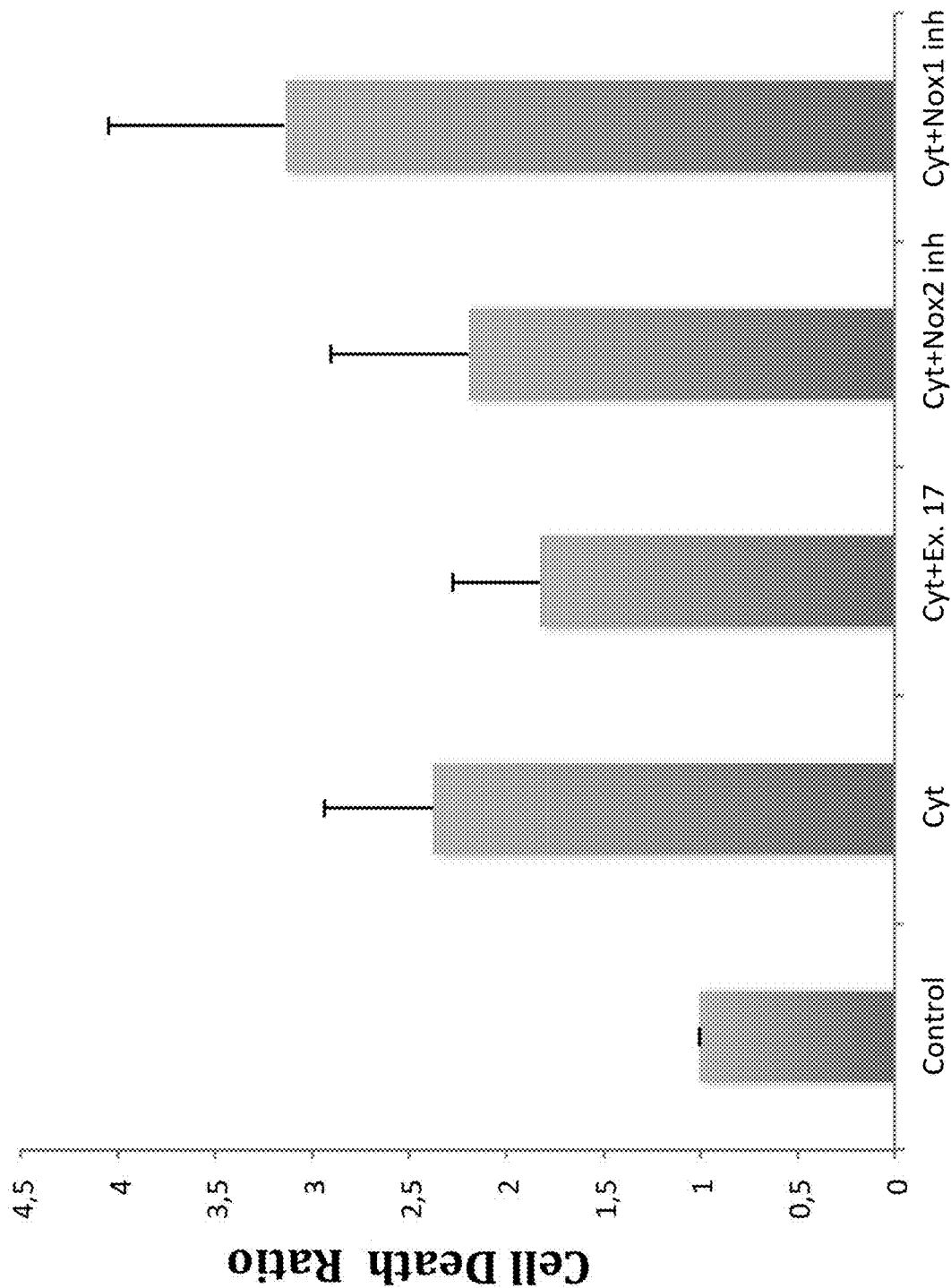
FIG. 12 is a bar chart representing the effect of the cytokines IL-10 (20 ng/ml) and IFN-γ (20 ng/ml) on human islet cells (Cyt); on human islet cells in the presence of Example 17 (1 µM) (Cyt+Ex. 17); on human islet cells in the presence of Phos-I2 (2 µM) (Cyt+Nox2 inh); and on human islet cells in the presence of ML-171 (2 µM) (Cyt+Nox1 inh), respectively. The effect is shown as a cell death ratio compared to human islet cells cultured in the absence of any cytokines (Control).
Figure 13:
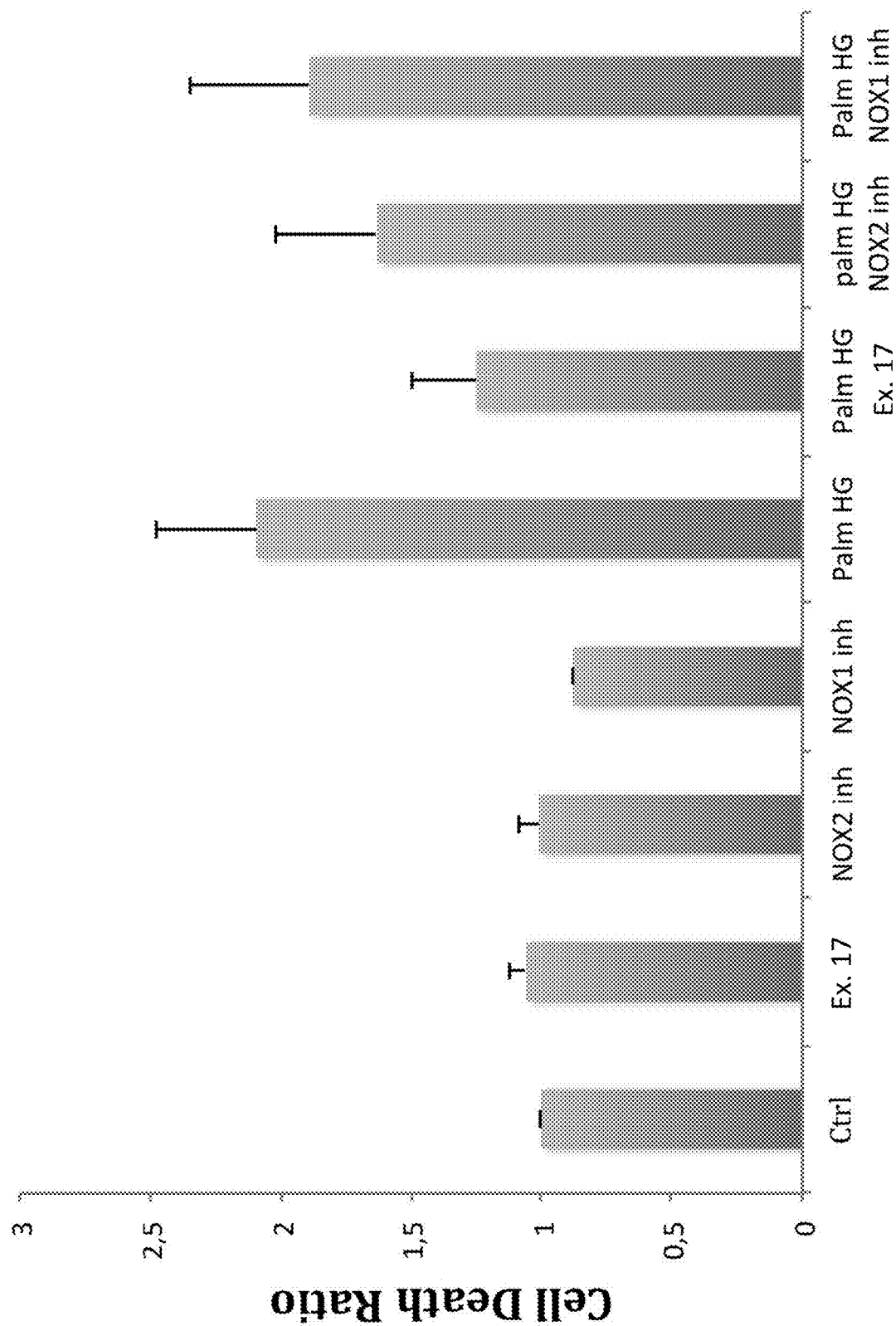
FIG. 13 is a bar chart representing the effect of palmitate (1.5 mM) and high glucose (20 mM) on human islet cells (Palm HG); on human islet cells in the presence of Example 17 (1 µM) (Palm HG Ex. 17); on human islet cells in the presence of Phos-I2 (2 µM) (Palm HG NOX2 inh); and on human islet cells in the presence of ML-171 (2 µM) (Palm HG NOX1 inh), respectively. The effect is shown as a cell death ratio compared to human islet cells cultured in culture medium only (Control). Also shown are the cell death ratios for human islet cells cultured in the presence of Example 17 at 1 µM (Ex. 17), Phos-I2 at 2 µM (NOX2 inh) and ML-171 at 2 µM (NOX1 inh).

As illustrated in FIGS. 12 and 13, the Nox1 selective inhibitor ML171 (Gianni D, et al., ACS Chem Biol. 2010 Oct. 15; 5(10): 981-93), at a concentration of 2 µM, failed to reduce human islet cell death during a 48 h culture period with cytokines or high glucose+palmitate. The Rac1/Nox2 selective inhibitor Phox-I2 (Bosco E E, et al., Chem Biol. 2012 Feb. 24; 19(2): 228-42), at a concentration of 2 µM, also failed to protect human islets against cytokines but partially protected against high glucose+palmitate. On the other hand, Example 17, at a concentration of only 1 µM, protected both against cytokines and high glucose+palmitate.

Modulation of TGFβ-Induced Lens Epithelial to Mesenchymal Transition (EMT)

Ocular tissues were collected from postnatal-day-21 albino Wistar rats (Rattus norvegicus) that were sacrificed by asphyxiation and subsequent cervical dislocation.

Lens epithelial explants were prepared as previously described (Wang Q, et al., Investigative ophthalmology & visual science. 2010; 51(7):3599-610) and cultured in Medium 199 (M199) with Earle's salts (Life Technologies, USA), supplemented with 50 µg/mL L-glutamine, 50 IU/mL penicillin/50 µg/mL streptomycin (Thermo Scientific, USA), 2.5 µg/mL Amphostat B (Thermo Scientific, USA) and 0.1% bovine serum albumin (BSA) (Sigma, USA). M199 was equilibrated at 37° C., 5% CO$_2$. To induce EMT, recombinant TGF-β2 was added to media in each culture dish at a working concentration of 200 µg/ml (R&D Systems, USA). Prior to the addition of TGF-β2, some explants were pre-treated for 30 minutes with Example 11 or Example 17, at working concentrations of 2.4 µM and 0.3 µM, respectively. The progression of EMT in live cells was observed and captured using phase-contrast microscopy (Olympus CK2, Japan) and a digital camera (Leica DFC-280, Germany). Percentage cell loss quantification was performed using the thresholding function of ImageJ (NIH), such that cells could be distinguished from bare lens capsule.

For immunofluorescence analyses, at the end of the culture period, explants were fixed in absolute methanol for 45 seconds, followed by 3 consecutive 15 second rinses in phosphate buffered saline (PBS). Explants were blocked in 10% normal goat serum (NGS) for 1 hour at room temperature. Excess NGS was removed and primary antibody was applied, diluted in 0.15% NGS/PBS supplemented with 1% bovine serum albumin (BSA). Dishes were left to incubate overnight at 4° C. in a humidified chamber. α-smooth muscle actin was labelled with a specific monoclonal mouse antibody (Sigma, USA), diluted 1:100. Nox4 was labelled with a specific polyclonal rabbit antibody (Santa Cruz Biotechnology, USA), diluted 1:50. The following day, dishes were equilibrated at room temperature and subject to 3×5 minute washes in PBS/BSA. An appropriate secondary antibody was diluted in PBS/BSA and applied to each explant for 2 hours in dark conditions. α-smooth muscle actin was detected using goat anti-mouse Alexa-Fluor 488 (Cell Signaling, USA). Nox4 was detected using an anti-rabbit whole IgG conjugated to Alexfluor 594 (Sigma). A dilution of 1:1000 was used for all secondary antibodies. Dishes were subsequently rinsed in PBS/BSA and a 1:2000 solution of bisbenzimide (Hoechst dye) diluted in PBS/BSA was applied for 3 minutes to visualize cell nuclei. Immunofluorescent labelling was viewed and captured using epifluorescence microscopy (Leica-DMLB, Germany), and a digital camera (Q-Imaging MicroPublisher 3.3 RTV, Canada).

Figure 14:
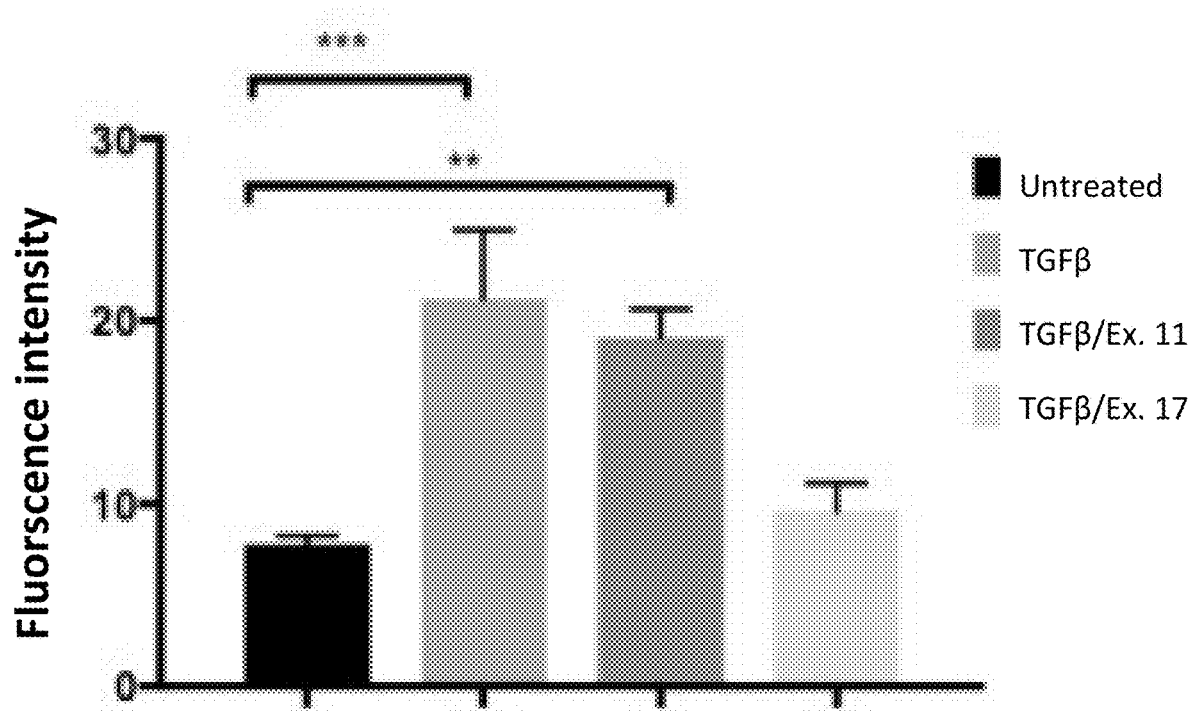
FIG. 14 is a bar chart showing total fluorescence from epithelial cells of rat lens explants (untreated), from epithelial cells of rat lens explants treated with TGFβ for 8 hours (TGFβ), from epithelial cells of rat lens explants treated with TGFβ and Example 11 for 8 hours (TGFβ/Ex. 11), and from epithelial cells of rat lens explants treated with TGFβ and Example 17 for 8 hours (TGFβ/Ex. 17), and stained for superoxide with DHE. Means and SEM were calculated using Graph Pad Prism v7.0. Statistical significance was determined using one-way ANOVA, using Tukey post-hoc estimation ($p<0.01$, $*p<0.001$, n=3 individual independent experiments). Error bars: SEM.

At a determined treatment period, 1 μL of 30 mM DHE (dihydroethidium, Life Technologies, USA) (reconstituted in DMSO according to manufacturer's instructions) was added to each dish containing 1 mL of Hank's Balanced Salt Solution (Life Technologies) to yield a working concentration of 3004. Dishes were returned to the incubator for 30 minutes. Explants were then rinsed in cold phosphate-buffered saline (PBS) (3×15 seconds), before being mounted in 40 μl of 10% glycerol/PBS. In its reduced form, DHE typically fluoresces blue; however, it undergoes oxidation in the presence of the superoxide anion, enabling it to intercalate with the cell's DNA and emit red fluorescence; staining nuclei of cells (Wang X, et al. Imaging ROS signaling in cells and animals. J Mol Med (Berl). 2013; 91(8):917-27). DHE staining was viewed with an epifluorescence microscope (Leica-DMLB, Germany) and digital camera (Q-Imaging MicroPublisher 3.3 RTV, Canada). Total fluorescence was calculated using ImageJ (NIH, USA). (FIG. 14).

Figure 15:
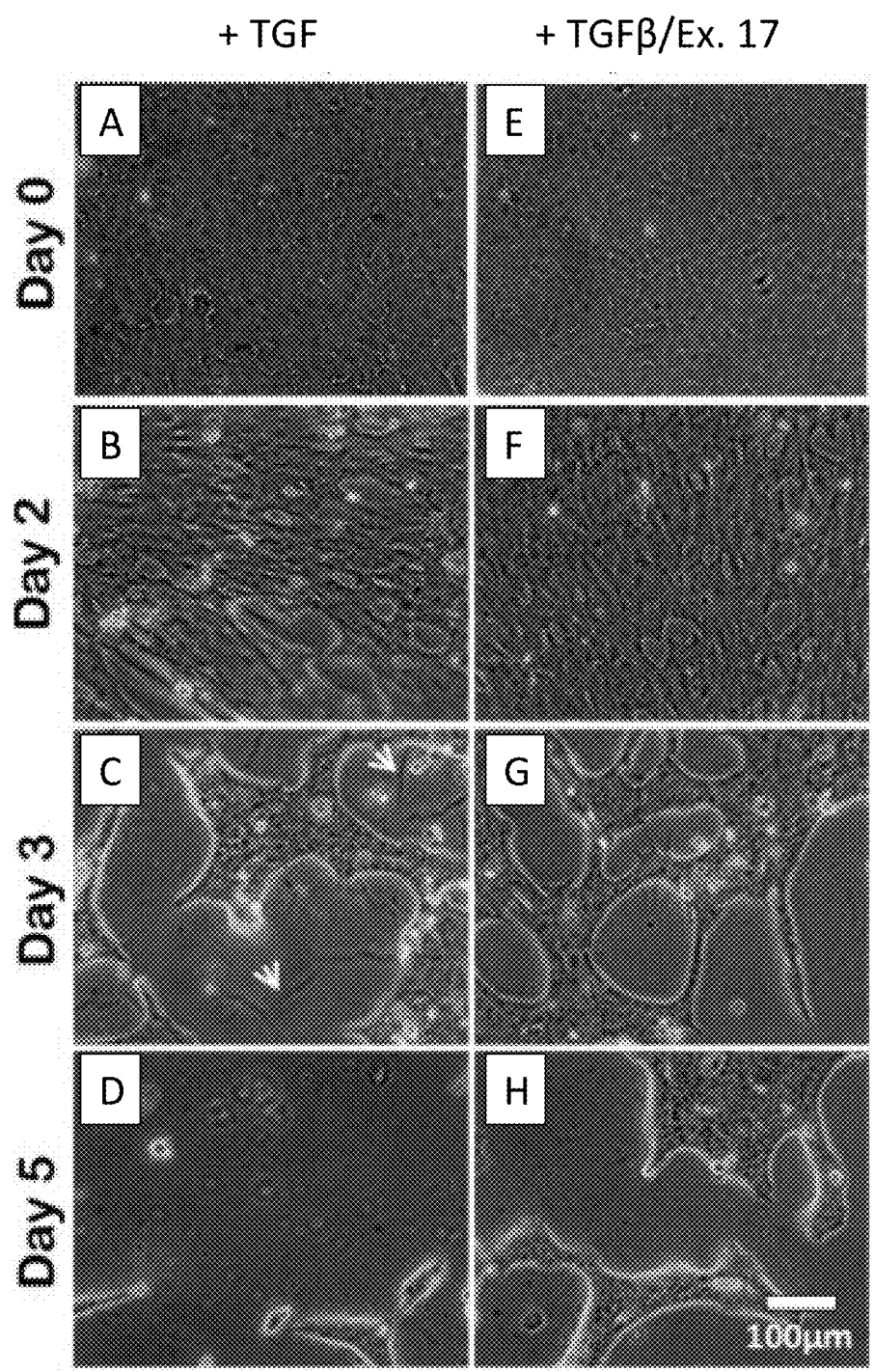
FIG. 15(A-H) shows micrographs, taken on days 0, 2, 3 and 5, of rat lens explants treated and cultured for 5 days with TGFβ (A-D), or with TGFβ and Example 17 (E-H).

It further was noted that explants treated with TGFβ alone underwent EMT that was marked by elongation of the lens epithelial cells (LECs) by 2 days of treatment (FIG. 15B), and progressive cell loss by day 3 and day 5 (FIGS. 15C and 15D, respectively), compared to untreated epithelial explants where cells remained cobblestone (data not shown), and to day 0 control explants (FIGS. 15A and 15E). Progressive cell loss revealed bare lens capsule that presented prominent lens capsular wrinkling (FIG. 15C, white arrowheads). This was in contrast to untreated explants where cells remained cuboidal over 5 days, comparable to explants at day 0 (FIGS. 15A and 15E). Co-treatment with TGFβ and Example 17 appeared to delay the progression of EMT (FIG. 15F); a similar effect was obtained when co-treating with TGFβ and Example 11. Although there was some bare capsule evident by 2 days of culture with both TGFβ and either inhibitor added (FIG. 15F), cells did not elongate as much compared to when treated with only TGFβ, and did not exhibit any lens capsular wrinkling by day 3 (FIG. 15G). By day 5, TGFβ-treated explants had some clusters of cells remaining (FIG. 15D), whereas in explants treated with TGFβ and either Example 11 or 17, some of the remaining cells appeared epithelial-like. Neither inhibitor significantly promoted cell survival on any of the culture days. The findings from the study suggest that Nox4 is not fundamentally required for all aspects of TGFβ induced lens EMT, and that lens epithelial cells may be capable of upregulating compensatory mechanisms. The study demonstrate that TGFβ-induced Nox4 activity is responsible for ROS production in early stages of lens EMT.

Gene Expression Analysis

Quantitative RT-PCR (qRT-PCR) gene expression analysis was performed as previously described (Shu D, et al., Investigative ophthalmology & visual science. 2017; 58(2): 781-96.).

The gene name abbreviations, gene names and NCBI identifiers of the studied genes are shown in Table 4 and the forward and reverse primers sequences used for the qRT-PCR expression are shown in Tables 5 and 6, respectively.

TABLE 4

| Gene abbreviation | Gene name | NCBI ID |
| --- | --- | --- |
| Smurf1 | SMAD Specific E3 Ubiquitin Protein Ligase 1 | NM_001109598.1 |
| Snail1 | Snail Family Transcriptional Repressor 1 | NM_053805.1 |
| GAPDH | Glyceraldehyde-3-Phosphate Dehydrogenase | NM_017008.4 |
| NCad | Neural Cadherin | NM_031333.1 |
| Fn | Fibronectin | NM_019143.2 |
| Col1A1 | Collagen Type I Alpha 1 Chain | NM_053304.1T |
| αSMA | actin, alpha 2, smooth muscle | NM_031004.2 |
| Ecad | Epithelial Cadherin | NM_031334.1 |
| MMP9 | Matrix metallopeptidase 9 | NM_031055.1 |
| CTGF | Connective Tissue Growth Factor | NM_022266.2 |

TABLE 5

| Gene abbreviation | Forward (5'-3') primer sequence | SEQ ID NO. |
| --- | --- | --- |
| Smurf1 | AAGGCTTCAAGGCTCTGCAA | 1 |
| Snail1 | CGTGTGTGGAGTTCACCTTCC | 2 |
| GAPDH | AGACAGCCGCATCTTCTTGT | 3 |
| NCad | CTGCCATGACCTTCTACGGA | 4 |
| Fn | CCATCACTGGTCTGGAGCC | 5 |
| Col1A1 | TGACTGGAAGAGCGGAGAGT | 6 |
| αSMA | CTATGCTCTGCCTCATGCCA | 7 |
| Ecad | CTGGACCGAGAGAGTTACCC | 8 |
| MMP9 | TGAGGCCCCTACAGAGTCTT | 9 |
| CTGF | GCGTGTGCACTGCCAAAGAT | 10 |

TABLE 6

| Gene abbreviation | Forward (5'-3') primer sequence | SEQ ID NO. |
|---|---|---|
| Smurf1 | AAGGCCCACACCTGCTTTAAT | 11 |
| Snail1 | TTTGCCACTGTCCTCATCGG | 12 |
| GAPDH | ATGACTCTACCCACGGCAAG | 13 |
| NCad | TTTGCCATCCTGACAGACCC | 14 |
| Fn | ACCAGTTGGGGAAGCTCATC | 15 |
| Col1A1 | GATAGCGACATCGGCAGGAT | 16 |
| αSMA | CTCACGCTCAGCAGTAGTCA | 17 |
| Ecad | GGCACCGACCTCATTCTCAA | 18 |
| MMP9 | TCCAATACCGACCGTCCTTG | 19 |
| CTGF | TGGCTCGCATCATAGTTGGG | 20 |

For data analysis, the $2^{-\Delta\Delta Ct}$ method was used to estimate the relative fold change in gene expression. Using the $2^{-\Delta\Delta Ct}$ method, the gene of interest was quantified relative to, firstly, the housekeeping gene, GAPDH and, secondly, to relative gene expression in untreated explants.

Figure 16:
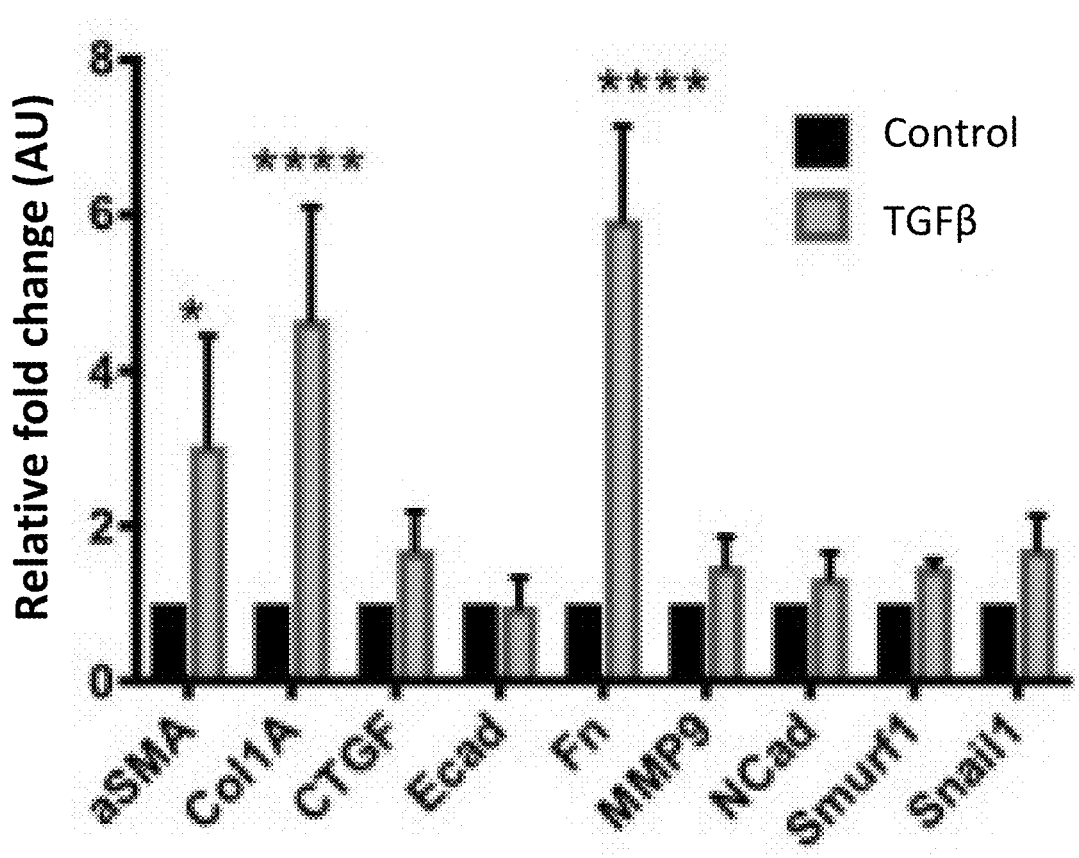
FIG. 16 is a bar chart showing the upregulation of genes, in P21 rat lens epithelial explants at 48 hours of culture with (TGFβ) or without (control) treatment with TGFβ. The upregulation is expressed as relative fold change (AU) compared to expression of the same genes in the control culture.
Figure 17:
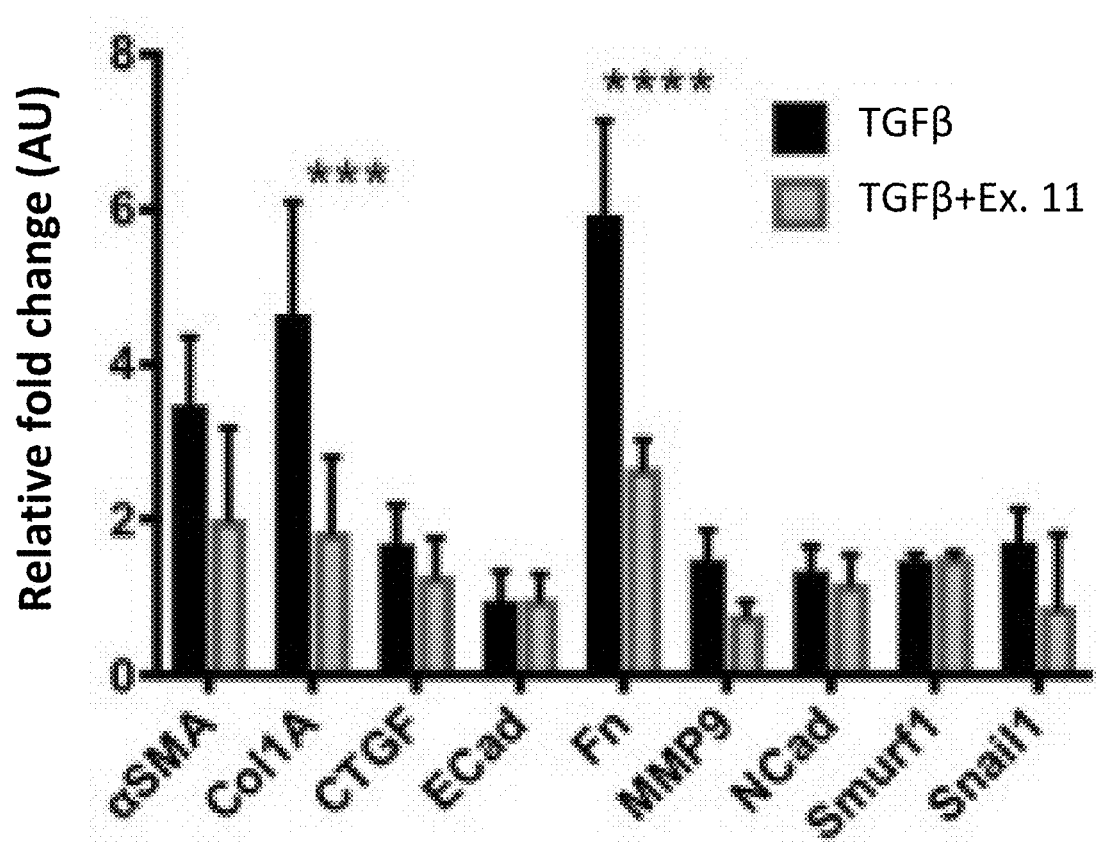
FIG. 17 is a bar chart showing the upregulation of genes, in P21 rat lens epithelial explants treated with TGFβ alone (TGFβ) or with TGFβ and Example 11 (TGFβ+Ex. 11) at 48 hours of culture treated. The upregulation is expressed as relative fold change (AU) compared to expression of the same genes in the presence of TGFβ alone.
Figure 18:
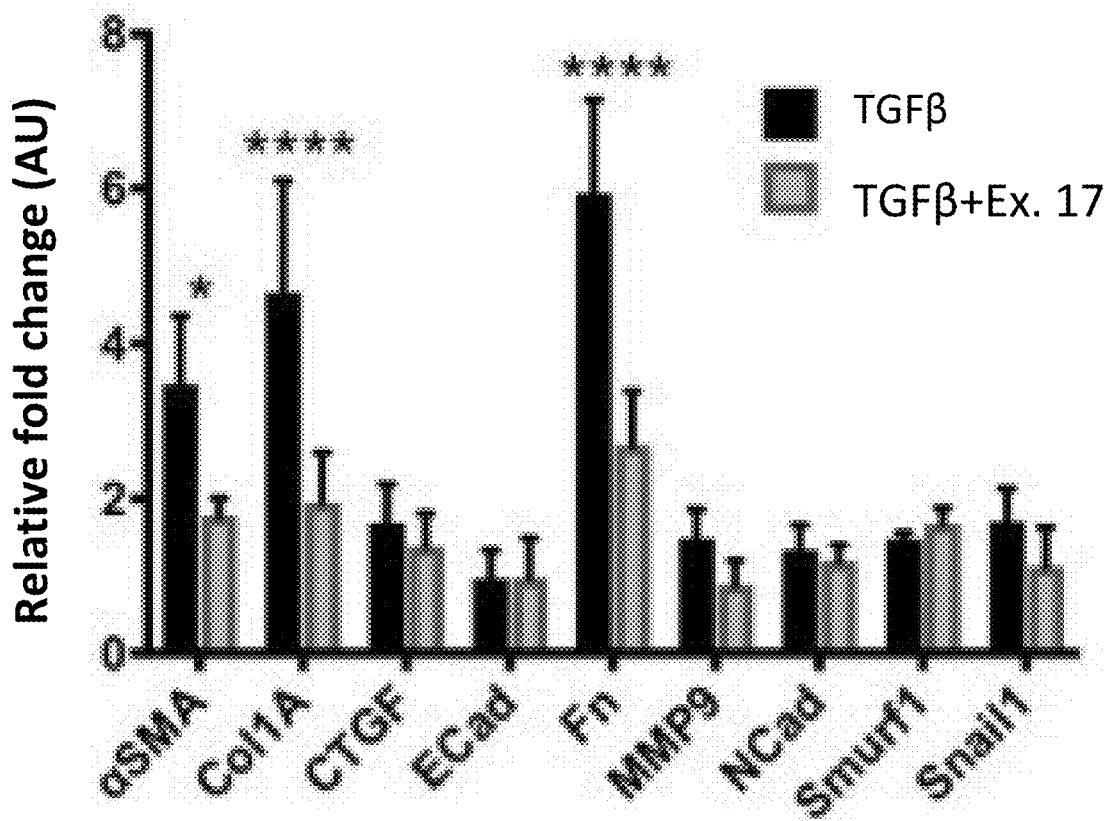
FIG. 18 is a bar chart showing the upregulation of genes, in P21 rat lens epithelial explants treated with TGFβ alone (TGFβ) or with TGFβ and Example 17 (TGFβ+Ex. 17) at 48 hours of culture treated. The upregulation is expressed as relative fold change (AU) compared to expression of the same genes in the presence of TGFβ alone. Means and SEM were calculated using GraphdPad Prism v7.0. Statistical significance was determined using one-way ANOVA, using Tukey post-hoc estimation ($*p<0.05$, $p<0.01$, $*p<0.001$, $****p<0.0001$ n=3 individual independent experiments). Error bars: SEM.

Gene expression analysis by qRT-PCR revealed significantly elevated mRNA transcripts for aSMA, Col1A and Fn upon TGFβ treatment (FIG. 16). Both of the compounds were able to downregulate the TGFβ-driven upregulation of Col1A and Fn, and both were able to downregulate aSMA expression (FIGS. 17 and 18), albeit Example 17 did so at a higher degree than Example 11. It therefore appears that a higher dose of Example 11 may be required to attenuate TGFβ-induced ROS. However, both compounds inhibited TGFβ-induced upregulation of mesenchymal genes, suggesting that both compounds were actively targeting Nox4-mediated regulation of these genes.

Streptozotocin Rat Model of Diabetic Retinopathy

Animals were maintained on a 12 h light-dark cycle, at 22-25° C. Food and water were available ad libitum. Diabetes was induced by a single dose of streptozotocin (STZ, 70 mg/kg, ip, Sigma-Aldrich, Germany) dissolved in sodium citrate (0.1M) buffer (diabetic group) after a fasting period of 8-12 hours. Animals with blood glucose levels>350 mg/dl, after 72 hours post-STZ injection were considered diabetic. Both male and female Sprague-Dawley rats were used in the study. Three experimental groups were employed, namely Control (n=6), Diabetic (n=7), and Diabetic-treated group (n=6). Example 17 (10 mg/ml) dissolved in DMSO was administered as eye drops, for two weeks, starting two (2) days after STZ administration. Animals were euthanized 24 hours after the last treatment, and their eyes were removed.

Immunohistochemical studies were performed according to Arias et al. (Diabetes, 67, 321-333, 2018). In short, the eyes removed from the euthanized animals were fixed by immersion in 4% paraformaldehyde in 0.1 M phosphate buffer for 45 min at 4° C. The eyecups were isolated and fixed in 4% paraformaldehyde in 0.1 M phosphate buffer for 1.5 h at 4° C. After fixation, tissues were embedded in optimal cutting temperature compound (OCT compound, Prolabo, Leuven, Belgium) and frozen in isopentane for 1 min. Serial transverse retinal sections (10 μm) were collected.

Figure 19:
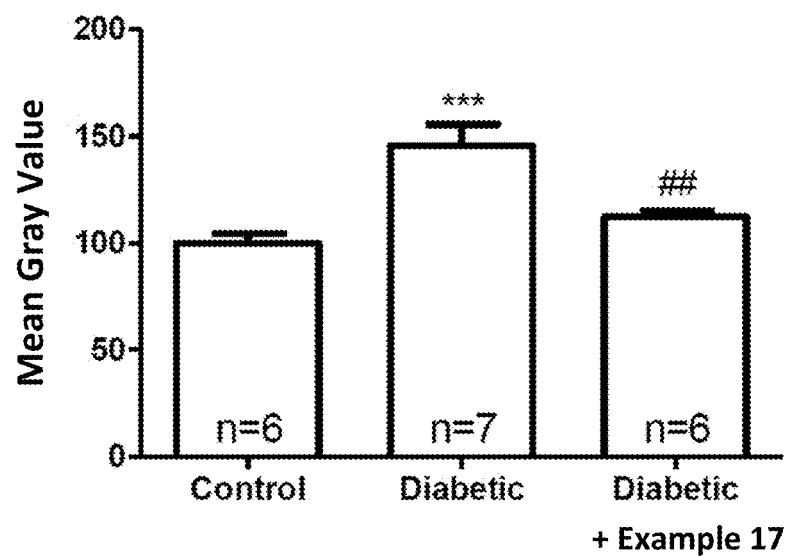
FIG. 19 is a bar chart showing the mean gray value for glial fibrillary acidic protein (GFAP) immunoreactivity measured in eye preparations obtained from healthy (Control) or diabetic rats (Diabetic), and from diabetic rats treated with Example 17 (Diabetic+Example 17), respectively. The immunoreactivity measured in eye preparations from healthy rats is set as 100%, and values obtained from diabetic rats with or without treatment with Example 17 are indicated versus the control values. $***p<0.001$, $\#\#p<0.01$.

Antibodies raised against the macroglia marker glial fibrillary acidic protein (GFAP) were employed. Quantification using the public domain ImageJ 1.43m software was employed for the mean gray value [integrated density (fluorescence density)/delineated area] calculated and expressed as a percentage of the mean gray value of the control. Statistical analysis of the data was performed using Graph-Pad Prism v5.0 (San Diego, Calif., USA) and differences between groups were evaluated by one-way analysis of variance (ANOVA) with Neuman-Keuls. Statistical significance was set at $p<0.05$. As shown in FIG. 19, Example 17 (10 mg/ml) administered as eye drops for two weeks attenuated the diabetes induced increase in GFAP immunoreactivity.

Solubility, Chemical and Metabolic Stability and Plasma Protein Binding Properties Solubility, chemical and metabolic stability and plasma protein binding properties of the inventive compounds have also been studied as described herein below.

Determination of Solubility

Two μl of test compound (from 10 mM DMSO stock) were diluted 100× in 10 mM potassium phosphate pH 7.4 in a HPLC glass vial, sealed and incubated for 24 h under rotation (900 rpm) at room temperature. After the incubation 150 μl were transferred to conical glass inserts and centrifuged for 20 min at 10,000×g. Two μl of the supernatant were transferred to a 96-well plate, diluted 100× with acetonitrile/$H_2O$ (60/40, vol/vol) and analyzed by LC-MS/MS.

Determination of Chemical Stability

Test compound was pipetted into an HPLC vial, from 10 mM DMSO, to yield 2 μM final concentration in three separate vials containing buffers with different pH. At reaction start the three different buffers were mixed with isopropanol (1:2, buffer:isopropanol). The buffers used were: pH 2 ($H_3PO_4$/$KH_2PO_4$ 10 mM), pH 7.4 ($KH_2PO_4$/$K_2HPO_4$ 10 mM) and pH 10 (Glycine/NaOH 10 mM). Immediately (<1 minute) after buffer or buffer/isopropanol addition, a 100 μl aliquot was added to a separate plate containing 100 μl acetonitrile:$H_2O$ (60:40) and Warfarin (internal standard, IS), sealed and frozen at −20° C. This test was made for 2 h and 20 h. Analysis was performed on a XEVO TQ mass spectrometer coupled to an Acquity UPLC system in ESI$^+$ MRM mode, separation on a BEH C18 2×50 mm column.

Determination of Metabolic Stability

The microsomal metabolic stability assay utilizes pooled human, or animal (mouse) species, liver microsomes with supplemented cofactor (NADPH) to primarily facilitate cytochrome P450 (CYP) reactivity against target compound. Test compound (1 μM incubation concentration) and microsomes (0.5 mg/ml incubation concentration) were diluted in 0.1 M phosphate buffer, pH 7.4, in a volume of 150 μl. The reaction was initiated with addition of NADPH (1 mM). The incubation times were 0, 5, 15, 40 min and the reaction was quenched, at each time point, by addition of 100 μl acetonitrile containing Warfarin as IS. The plate was then sealed, centrifuged and frozen at −20 C until LC-MS/MS analysis.

Determination of Plasma Protein Binding

Example compounds were incubated at 10 μM in plasma and then equilibrium dialysed for 4 h, using a rapid equilibrium device. Protein binding (fu %) was determined by LS/MS as previously described (Anvari E, et al., vide supra).

Results obtained for some compounds of the invention are shown in Table 7 herein below.

TABLE 7

| Ex. | Kinetic solub. μM | Chem. stab. pH 7.4 | Metab. stab, human $t_{1/2}$ min | Metab. stab, mouse $t_{1/2}$ min | fu % human plasma protein | fu % mouse plasma protein |
|---|---|---|---|---|---|---|
| 17 | 0.16 | stable | 3-4 | 2-3 | 0.02 | 0.04 |
| 35 | 4.5 | stable | 11-13 | 6-20 | 0.02 | 0.02 |
| 37 | >100 | stable | 6-10 | 2-4 | 1.1 | 0.56 |
| 38 | 77 | stable | 9-11 | 2-4 | 0.62 | 0.56 |
| 44 | 94 | stable | 36 | 7 | 1.5 | 2.5 |
| 46 | 16 | stable | 2 | 2 | 0.26 | 0.21 |
| 47 | >100 | stable | 14 | 1 | 3.0 | 1.7 |
| 48 | 97 | stable | 69 | 16 | 1.1 | 0.5 |

As may be seen from Table 7, some of the compounds of the invention have surprisingly favourable characteristics in terms of solubility, metabolic stability and plasma protein binding.

The invention claimed is:

1. A compound of formula (Ia)

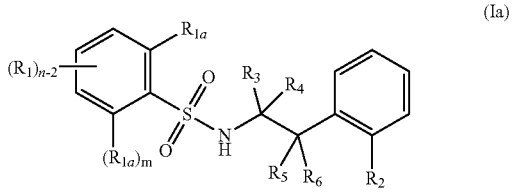

(Ia)

or a pharmaceutically acceptable salt thereof, wherein
m is 1;
n is an integer of from 3 to 5;
each $R_1$ is independently selected from C1-C6 alkyl, C3-C6 carbocyclyl, C3-C6 carbocyclyl-C1-C3 alkyl, C1-C6 alkoxy, C1-C6 alkoxy-C1-C3 alkyl, C3-C6 carbocyclyloxy, C3-C6 carbocyclyloxy-C1-C3 alkyl, 4- to 6-membered heterocyclyl, 4- to 6-membered heterocyclyl-C1-C3 alkyl, hydroxy, hydroxy-C1-C3 alkyl, Cl, and Br; and when n is at least 4, two $R_1$ attached to adjacent atoms of the phenyl ring, together with the phenyl ring atoms to which they are attached, may form a 4- to 6-membered non-aromatic ring optionally containing one or more heteroatoms and optionally substituted with one or more moieties independently selected from C1-C3 alkyl and halogen;
one $R_{1a}$ is halogen, and the other $R_{1a}$ is selected from C1-C6 alkyl, C1-C6 alkoxy, hydroxy, and halogen;
$R_2$ is selected from C1-C3 alkyl, halogen, hydroxy, and hydroxy-C1-C3 alkyl;
$R_3$, $R_4$, $R_5$, and $R_6$ are independently selected from H and F;
any alkyl is optionally substituted with one or more halogens; and
any carbocyclyl or heterocyclyl is optionally substituted with one or more moieties independently selected from halogen and C1-C3 alkyl.

2. The compound of claim 1, or a pharmaceutically acceptable salt thereof, wherein $R_2$ is selected from C1-C3 alkyl, halogen, and hydroxy.

3. The compound of claim 1, or a pharmaceutically acceptable salt thereof, wherein $R_2$ is selected from methyl, trifluoromethyl, F, Cl, and hydroxy.

4. The compound of claim 1, or a pharmaceutically acceptable salt thereof, wherein each $R_1$ is independently selected from C1-C6 alkyl, C3-C6 cyclolalkyl, C3-C6 cycloalkyl-C1-C3 alkyl, C1-C6 alkoxy, C1-C6 alkoxy-C1-C3 alkyl, hydroxy, hydroxy-C1-C3 alkyl, Cl, and Br; and when n is at least 4, two $R_1$ attached to adjacent atoms of the phenyl ring, together with the phenyl ring atoms to which they are attached, may form a 4- to 6-membered non-aromatic ring optionally containing one or more heteroatoms and optionally substituted with one or more moieties independently selected from C1-C3 alkyl and halogen.

5. The compound of claim 1, of formula (Ib)

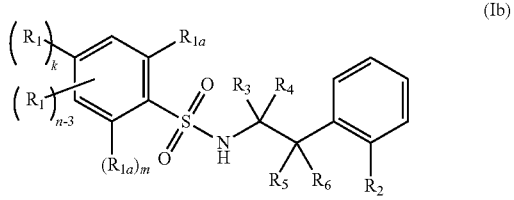

(Ib)

or a pharmaceutically acceptable salt thereof, wherein
k is 1;
and
m, n, and each $R_1$, $R_{1a}$, $R_2$, $R_3$, $R_4$, $R_5$, and $R_6$ are as defined in claim 1.

6. The compound of claim 1, or a pharmaceutically acceptable salt thereof, wherein one $R_{1a}$ is halogen, and the other $R_{1a}$ is independently selected from C1-C3 alkyl, hydroxy, and halogen.

7. The compound of claim 6, or a pharmaceutically acceptable salt thereof, wherein one $R_{1a}$ is chloro, and the other $R_{1a}$ is independently selected from methyl, hydroxy, and chloro.

8. The compound of claim 1, or a pharmaceutically acceptable salt thereof, wherein n is 3.

9. A compound according to claim 1, selected from
4-bromo-2,6-dichloro-N-[2-(2-fluorophenyl)ethyl]benzene-1-sulfonamide;
4-bromo-2,6-dichloro-N-[2-(2-methylphenyl)ethyl]benzene-1-sulfonamide;
4-bromo-2,6-dichloro-N-{2-[2-(trifluoromethyl)phenyl] ethyl}benzene-1-sulfonamide;

4-bromo-2,6-dichloro-N-[2-(2-chlorophenyl)ethyl]benzene-1-sulfonamide;

2,6-dichloro-N-[2-(2-fluorophenyl)ethyl]-4-(pyridin-3-yl) benzene-1-sulfonamide;

2,6-dichloro-4-cyclopropyl-N-[2-(2-fluorophenyl)ethyl] benzene-1-sulfonamide;

2,6-dichloro-N-[2-(2-chlorophenyl)ethyl]-4-cyclopropyl-benzene-1-sulfonamide;

2,6-dichloro-N-[2-(2-chlorophenyl)ethyl]-4-(trifluoromethyl) benzene-1-sulfonamide;

4-bromo-2,6-dichloro-N-[2,2-difluoro-2-(2-methylphenyl)ethyl]benzene-1-sulfonamide;

4-bromo-2,6-dichloro-N-[2-(2-chlorophenyl)-2,2-difluoroethyl]benzene-1-sulfonamide;

4-bromo-2,6-dichloro-N-[2-fluoro-2-(2-methylphenyl)ethyl]benzene-1-sulfonamide;

4-bromo-2,6-dichloro-N-[2-(2-hydroxyphenyl)ethyl]benzenesulfonamide;

2,6-dichloro-N-[2-(2-hydroxyphenyl)ethyl]-4-(trifluoromethyl) benzenesulfonamide;

2,4-dichloro-6-hydroxy-N-[2-(2-hydroxyphenyl)ethyl] benzenesulfonamide;

2,4-dichloro-6-hydroxy-N-[2-(o-tolyl)ethyl]benzenesulfonamide; and 6-chloro-3-hydroxy-N-[2-(2-hydroxyphenyl)ethyl]-2,4-dimethyl-benzenesulfonamide;

or a pharmaceutically acceptable salt thereof.

10. A pharmaceutical composition comprising a compound as defined in claim 1 or a pharmaceutically acceptable salt thereof, and optionally a pharmaceutically acceptable excipient.

11. The compound of claim 1, or a pharmaceutically acceptable salt thereof, wherein each $R_1$ is selected from C1-C6 alkyl, C3-C6 cyclolalkyl, C1-C6 alkoxy, hydroxy, Cl, and Br.

12. The compound of claim 1, or a pharmaceutically acceptable salt thereof, wherein each $R_1$ is selected from C1-C3 alkyl, Cl, and Br.

13. The compound of claim 8, or a pharmaceutically acceptable salt thereof, wherein $R_1$ is Cl or Br.

14. The compound of claim 1, or a pharmaceutically acceptable salt thereof, wherein each $R_{1a}$ is Cl.

15. The compound of claim 1, or a pharmaceutically acceptable salt thereof, wherein $R_2$ is selected from C1-C3 alkyl.

16. The compound of claim 1, or a pharmaceutically acceptable salt thereof, wherein $R_3$ and $R_4$ are H; and $R_5$, and $R_6$ are independently selected from H and F.

17. The compound of claim 1, or a pharmaceutically acceptable salt thereof, wherein each one of $R_3$, $R_4$, $R_5$, and $R_6$ is H.

18. The pharmaceutical composition of claim 10, wherein the compound is selected from 4-bromo-2,6-dichloro-N-[2-(2-fluorophenyl)ethyl]benzene-1-sulfonamide;

4-bromo-2,6-dichloro-N-[2-(2-methylphenyl)ethyl]benzene-1-sulfonamide;

4-bromo-2,6-dichloro-N-{2-[2-(trifluoromethyl)phenyl]ethyl}benzene-1-sulfonamide;

4-bromo-2,6-dichloro-N-[2-(2-chlorophenyl)ethyl]benzene-1-sulfonamide;

2,6-dichloro-N-[2-(2-fluorophenyl)ethyl]-4-(pyridin-3-yl) benzene-1-sulfonamide;

2,6-dichloro-4-cyclopropyl-N-[2-(2-fluorophenyl)ethyl] benzene-1-sulfonamide;

2,6-dichloro-N-[2-(2-chlorophenyl)ethyl]-4-cyclopropyl-benzene-1-sulfonamide;

2,6-dichloro-N-[2-(2-chlorophenyl)ethyl]-4-(trifluoromethyl) benzene-1-sulfonamide;

4-bromo-2,6-dichloro-N-[2,2-difluoro-2-(2-methylphenyl)ethyl]benzene-1-sulfonamide;

4-bromo-2,6-dichloro-N-[2-(2-chlorophenyl)-2,2-difluoroethyl]benzene-1-sulfonamide;

4-bromo-2,6-dichloro-N-[2-fluoro-2-(2-methylphenyl) ethyl]benzene-1-sulfonamide;

4-bromo-2,6-dichloro-N-[2-(2-hydroxyphenyl)ethyl]benzenesulfonamide;

2,6-dichloro-N-[2-(2-hydroxyphenyl)ethyl]-4-(trifluoromethyl) benzenesulfonamide;

2,4-dichloro-6-hydroxy-N-[2-(2-hydroxyphenyl)ethyl] benzenesulfonamide;

2,4-dichloro-6-hydroxy-N-[2-(o-tolyl)ethyl]benzenesulfonamide; and 6-chloro-3-hydroxy-N-[2-(2-hydroxyphenyl)ethyl]-2,4-dimethyl-benzenesulfonamide.

\* \* \* \* \*

SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Smurf1 Forward (5'-3') primer sequence

<400> SEQUENCE: 1
aaggcttcaa ggctctgcaa                                        20

<210> SEQ ID NO 2
<211> LENGTH: 21
<212> TYPE: DNA
<213> ORGANISM: Artificial Sequence
<220> FEATURE:
<223> OTHER INFORMATION: Snail1 Forward (5'-3') primer sequence

<400> SEQUENCE: 2
cgtgtgtgga gttcaccttc c                                      21

<210> SEQ ID NO 3
<211> LENGTH: 20
<212> TYPE: DNA
<213> ORGANISM: Artificial Sequence
<220> FEATURE:
<223> OTHER INFORMATION: GAPDH Forward (5'-3') primer sequence

<400> SEQUENCE: 3
agacagccgc atcttcttgt                                        20

<210> SEQ ID NO 4
<211> LENGTH: 20
<212> TYPE: DNA
<213> ORGANISM: Artificial Sequence
<220> FEATURE:
<223> OTHER INFORMATION: NCad Forward (5'-3') primer sequence

<400> SEQUENCE: 4
ctgccatgac cttctacgga                                        20

<210> SEQ ID NO 5
<211> LENGTH: 19
<212> TYPE: DNA
<213> ORGANISM: Artificial Sequence
<220> FEATURE:
<223> OTHER INFORMATION: Fn Forward (5'-3') primer sequence

<400> SEQUENCE: 5
ccatcactgg tctggagcc                                         19

```
<210> SEQ ID NO 6
<211> LENGTH: 20
<212> TYPE: DNA
<213> ORGANISM: Artificial Sequence
<220> FEATURE:
<223> OTHER INFORMATION: Col1A1 Forward (5'-3') primer sequence

<400> SEQUENCE: 6
tgactggaag agcggagagt                                           20

<210> SEQ ID NO 7
<211> LENGTH: 20
<212> TYPE: DNA
<213> ORGANISM: Artificial Sequence
<220> FEATURE:
<223> OTHER INFORMATION: alfaSMA Forward (5'-3') primer sequence

<400> SEQUENCE: 7
ctatgctctg cctcatgcca                                           20

<210> SEQ ID NO 8
<211> LENGTH: 20
<212> TYPE: DNA
<213> ORGANISM: Artificial Sequence
<220> FEATURE:
<223> OTHER INFORMATION: Ecad Forward (5'-3') primer sequence

<400> SEQUENCE: 8
ctggaccgag agagttaccc                                           20

<210> SEQ ID NO 9
<211> LENGTH: 20
<212> TYPE: DNA
<213> ORGANISM: Artificial Sequence
<220> FEATURE:
<223> OTHER INFORMATION: MMP9 Forward (5'-3') primer sequence

<400> SEQUENCE: 9
tgaggcccct acagagtctt                                           20

<210> SEQ ID NO 10
<211> LENGTH: 20
<212> TYPE: DNA
<213> ORGANISM: Artificial Sequence
<220> FEATURE:
<223> OTHER INFORMATION: CTGF Forward (5'-3') primer sequence

<400> SEQUENCE: 10
gcgtgtgcac tgccaaagat                                           20

<210> SEQ ID NO 11
<211> LENGTH: 21
<212> TYPE: DNA
<213> ORGANISM: Artificial Sequence
<220> FEATURE:
<223> OTHER INFORMATION: Smurf1 Reverse (5'-3') primer sequence

<400> SEQUENCE: 11
aaggcccaca cctgctttaa t                                         21

<210> SEQ ID NO 12
<211> LENGTH: 20
<212> TYPE: DNA
<213> ORGANISM: Artificial Sequence
<220> FEATURE:
<223> OTHER INFORMATION: Snail1 Reverse (5'-3') primer sequence
```

```
<400> SEQUENCE: 12
tttgccactg tcctcatcgg                                               20

<210> SEQ ID NO 13
<211> LENGTH: 20
<212> TYPE: DNA
<213> ORGANISM: Artificial Sequence
<220> FEATURE:
<223> OTHER INFORMATION: GAPDH Reverse (5'-3') primer sequence

<400> SEQUENCE: 13
atgactctac ccacggcaag                                               20

<210> SEQ ID NO 14
<211> LENGTH: 20
<212> TYPE: DNA
<213> ORGANISM: Artificial Sequence
<220> FEATURE:
<223> OTHER INFORMATION: NCad Reverse (5'-3') primer sequence

<400> SEQUENCE: 14
tttgccatcc tgacagaccc                                               20

<210> SEQ ID NO 15
<211> LENGTH: 20
<212> TYPE: DNA
<213> ORGANISM: Artificial Sequence
<220> FEATURE:
<223> OTHER INFORMATION: Fn Reverse (5'-3') primer sequence

<400> SEQUENCE: 15
accagttggg gaagctcatc                                               20

<210> SEQ ID NO 16
<211> LENGTH: 20
<212> TYPE: DNA
<213> ORGANISM: Artificial Sequence
<220> FEATURE:
<223> OTHER INFORMATION: Col1A1 Reverse (5'-3') primer sequence

<400> SEQUENCE: 16
gatagcgaca tcggcaggat                                               20

<210> SEQ ID NO 17
<211> LENGTH: 20
<212> TYPE: DNA
<213> ORGANISM: Artificial Sequence
<220> FEATURE:
<223> OTHER INFORMATION: alfaSMA Reverse (5'-3') primer sequence

<400> SEQUENCE: 17
ctcacgctca gcagtagtca                                               20

<210> SEQ ID NO 18
<211> LENGTH: 20
<212> TYPE: DNA
<213> ORGANISM: Artificial Sequence
<220> FEATURE:
<223> OTHER INFORMATION: Ecad Reverse (5'-3') primer sequence

<400> SEQUENCE: 18
ggcaccgacc tcattctcaa                                               20

<210> SEQ ID NO 19
```

```
<211> LENGTH: 20
<212> TYPE: DNA
<213> ORGANISM: Artificial Sequence
<220> FEATURE:
<223> OTHER INFORMATION: MMP9 Reverse (5'-3') primer sequence

<400> SEQUENCE: 19
tccaataccg accgtccttg                                              20

<210> SEQ ID NO 20
<211> LENGTH: 20
<212> TYPE: DNA
<213> ORGANISM: Artificial Sequence
<220> FEATURE:
<223> OTHER INFORMATION: CTGF Reverse (5'-3') primer sequence

<400> SEQUENCE: 20
tggctcgcat catagttggg                                              20
```